United States Patent
Woodley et al.

(10) Patent No.: US 12,123,033 B2
(45) Date of Patent: Oct. 22, 2024

(54) MODIFIED DOUBLE-STRANDED DONOR TEMPLATES

(71) Applicant: INTEGRATED DNA TECHNOLOGIES, INC., Coralville, IA (US)

(72) Inventors: Jessica Woodley, North Liberty, IA (US); Bernice Thommandru, Iowa City, IA (US); Joseph Dobosy, Coralville, IA (US); Mark Behlke, Coralville, IA (US); Adam Clore, Iowa City, IA (US); Garrett Rettig, Coralville, IA (US); Beimeng Sun, North Liberty, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 70 days.

(21) Appl. No.: 17/079,097

(22) Filed: Oct. 23, 2020

(65) Prior Publication Data

US 2021/0123035 A1    Apr. 29, 2021

Related U.S. Application Data

(60) Provisional application No. 62/925,366, filed on Oct. 24, 2019.

(51) Int. Cl.
| | | |
|---|---|---|
| C12N 15/66 | (2006.01) | |
| C12N 9/22 | (2006.01) | |
| C12N 15/113 | (2010.01) | |

(52) U.S. Cl.
CPC .............. *C12N 9/22* (2013.01); *C12N 15/113* (2013.01); *C12N 15/66* (2013.01); *C12N 2310/122* (2013.01); *C12N 2310/20* (2017.05); *C12N 2310/321* (2013.01); *C12N 2310/531* (2013.01); *C12N 2800/80* (2013.01)

(58) Field of Classification Search
None
See application file for complete search history.

(56) References Cited

U.S. PATENT DOCUMENTS

| | | |
|---|---|---|
| 9,822,407 B2 | 11/2017 | Joung et al. |
| 2012/0283110 A1 | 11/2012 | Shendure et al. |
| 2017/0053062 A1 | 2/2017 | Cradick et al. |
| 2017/0081679 A1 | 3/2017 | Xu et al. |
| 2017/0145486 A1 | 5/2017 | Chen et al. |
| 2017/0253925 A1 | 9/2017 | Dobosy et al. |
| 2018/0163265 A1 | 6/2018 | Zhang et al. |
| 2019/0062736 A1 | 2/2019 | Liu et al. |
| 2019/0119701 A1 | 4/2019 | Liang et al. |
| 2021/0002700 A1 | 1/2021 | Li et al. |

FOREIGN PATENT DOCUMENTS

| | | |
|---|---|---|
| WO | 2014093330 A1 | 6/2014 |
| WO | 2014143228 A1 | 9/2014 |
| WO | 2015013583 A2 | 1/2015 |
| WO | 2016030899 A1 | 3/2016 |
| WO | 2016081798 A1 | 5/2016 |
| WO | 2016138500 A1 | 9/2016 |
| WO | 2016205940 A1 | 12/2016 |
| WO | 2017040511 A1 | 3/2017 |
| WO | 2017066175 A1 | 4/2017 |
| WO | 2018119060 A1 | 6/2018 |
| WO | 2018232382 A1 | 12/2018 |
| WO | 2019051237 A1 | 3/2019 |
| WO | 2019/118949 A1 | 6/2019 |
| WO | 2019110067 A1 | 6/2019 |
| WO | 2019182037 A1 | 9/2019 |
| WO | 2019/246553 A1 | 12/2019 |
| WO | 2020178772 A1 | 9/2020 |

OTHER PUBLICATIONS

Deleavey et al. Designing Chemically Modified Oligonucleotides for Targeted Gene Silencing. Chemistry & Biology (2012) 19:937-954. (Year: 2012).*
Ostergaard et al. Biophysical and Biological Characterization of Hairpin and Molecular Beacon RNase H Active Antisense Oligonucleotides. ACS Chem. Biol. Feb. 5, 2015;10(5):1227-1233. (Year: 2015).*
Scoles et al. Antisense oligonucleotides: A primer. Neurol Genet. Apr. 1, 2019;5(2):e323. (Year: 2019).*
International Search Report and Written Opinion for Application No. PCT/US20/57105 dated Mar. 22, 2021 (14 pages).
International Searching Authority Invitation to Pay Additional Fees and Partial Search for Application No. PCT/US2021/042733 dated Nov. 3, 2021 (16 pages).
Amit et al., "Crispector provides accurate estimation of genome editing translocation and off-target activity from comparative NGS data", Nature Communications, May 2021, vol. 12, No. 1, pp. 1-16.
Lazzarotto et al., "Change-seq reveals genetic and epigenetic effects on CRISPR-Cas9 genome-wide activity", Nature Biotechnology, 2020, vol. 38, No. 111, pp. 1317-1327.
International Preliminary Report on Patentability for Application No. PCT/US2020/057105 dated May 5, 2022 (8 pages).
Bothmer et al., "Characterization of the interplay between DNA repair and CRISPR/Cas9-induced DNA lesions at an endogenous locus," Nature Communications, Jan. 2017, 8: 13905, 12 pages.

(Continued)

*Primary Examiner* — Allison M Fox
*Assistant Examiner* — Alyssa G Weston
(74) *Attorney, Agent, or Firm* — Michael Best & Friedrich LLP

(57) ABSTRACT

Described herein are compositions and methods for improving homology directed repair (HDR) efficiency and reducing homology-independent integration following introduction of double strand breaks with engineered nucleases. Additionally, modifications to double stranded DNA donors to improve the donor potency and efficiency of homology directed repair following introduction of double stranded breaks with programmable nucleases.

7 Claims, 16 Drawing Sheets

Specification includes a Sequence Listing.

(56) References Cited

OTHER PUBLICATIONS

Cameron et al., "Mapping the genomic landscape of CRISPR-Cas9 cleavage," Nat. Methods, Jun. 2017, 14(6): 600-606.
Chari et al., "Unraveling CRISPR-Cas9 genome engineering parameters via a library-on-library approach," Nat. Methods, Sep. 2015, 12(9): 823-826.
Clement et al., "Analysis and comparison of genome editing using CRISPResso2," bioRxiv, 2018, pp. 1-20.
Dai et al., "One-step generation of modular CAR-T cells with AAV-Cpf1," Nature Methods, Feb. 2019, 16(3): 247-254.
Dobosy et al., "RNase H-dependent PCR (rhPCR): Improved specificity and single nucleotide polymorphism detection using blocked cleavable primers," BMC Biotechnology, 2011, 11:80, 18 pages.
Eyquem et al., "Targeting a CAR to the TRAC locus with CRISPR/Cas9 enhances tumour rejection," Nature, Mar. 2017, 543: 113-117.
Giannoukos et al., "UDiTaS TM, a genome editing detection method for indels and genome rearrangements," BMC Genomics, 2018, 19:212, 10 pages.
Tamieh et al., "CAR T cell trogocytosis and cooperative killing regulate tumour antigen escape," Nature, Apr. 2019, 568(7750): 112-116.
Hendel et al., "Quantifying genome-editing outcomes at endogenous loci with SMRT sequencing," Cell Rep, Apr. 2014, 7(1): 293-305.
Iyer et al., "Precise therapeutic gene correction by a simple nuclease-induced double-stranded break," Nature, Apr. 2019, 568(7753): 561-565.
Labun et al., "Accurate analysis of genuine CRISPR editing events with ampliCan Kornel," bioRxiv, Sep. 2018, 15 pages.
Li, "Minimap2: Pairwise alignment for nucleotide sequences," Bioinformatics, 2018, 34: 3094-3100.
Lindsay et al., "CrispRVariants: precisely charting the mutation spectrum in genome engineering experiments," Nat. Biotechnol., 2015, 34: 701-703.
Liu et al., "CasX enzymes comprise a distinct family of RNA-guided genome editors," Nature, Feb. 2019, 566 (7743): 218-223.
Liu et al., "CRISPR-Cas9-mediated multiplex gene editing in CAR-T cells," Cell Research, Jan. 2017, 27: 154-157.
Nobles et al., "IGuide: An improved pipeline for analyzing CRISPR cleavage specificity," Genome Biol, Jan. 2019, 20:14, 6 pages.
Pinello et al., "Analyzing CRISPR genome-editing experiments with CRISPResso," Nat Biotech, 2016, 34: 695-697.
Rand et al., "Headloop suppression PCR and its application to selective amplification of methylated DNA sequences," Nucleic Acids Res, Aug. 2005, 33(14): e127, 11 pages.
Robinson et al., "Integrated genomics viewer," Nat. Biotechnol., Jan. 2011, 29: 24-26.
Shen et al., "Predictable and precise template-free CRISPR editing of pathogenic variants," Nature, Nov. 2018, 563(7733): 646-651.
Tsai et al., "Circle-seq: a highly sensitive in vitro screen for genome-wide CRISPR-Cas9 nuclease off-targets," Nat. Methods, Jun. 2017, 14(6): 607-614.
Tsai et al., "Guide-seq enables genome-wide profiling of off-target cleavage by CRISPR-Cas nucleases," Nat Biotechnol, Feb. 2015, 33(2): 187-197.
Vu et al., "Endogenous sequence patterns predispose the repair modes of CRISPR/Cas9-induced DNA double-stranded breaks in *Arabidopsis thaliana*," Plant J., Oct. 2017, 92(1): 57-67.
Wienert et al., "Unbiased detection of CRISPR off-targets in vivo using Discover-seq," Science, Apr. 2019, 364(6437): 286-289.
Yan et al., "Bliss is a versatile and quantitative method for genome-wide profiling of DNA double-strand breaks," Nat. Commun., May 2017, 8:15058, 9 pages.
Zetsche et al., "Cpf1 Is a Single RNA-Guide Endonuclease of a Class 2 CRISPR-Cas System," Cell, 2015, 163(3): 759-771.
International Search Report and Written Opinion for Application No. PCT/US2020/040621 dated Oct. 8, 2020 (14 pages).
Chang et al., "Non-homologous DNA end joining and alternative pathways to double-strand break repair", Nature Reviews Molecular Cell Biology, vol. 18, 2017, pp. 495-506.
Roth et al., "Reprogramming human T cell function and specificity with non-viral genome targeting", Nature, vol. 559, No. 7714, 2018, pp. 405-409.
Li et al., "Design and specificity of long ssDNA donrs for CRISPR-based knock-in", bioRxiv, 2017, 24 pages.
Gutierrez-Triann et al., "Efficient single-copy HDR by 5' modified long dsDNA donors", eLife, 2018, 15 pages.
Canaj et al., "Deep profiling reveals substantial heterogeneity of integration outcomes in CRISPR knock-in experiments", bioRxiv, 2019, 43 pages.
Ghanta et al., "5'Modifications Improve Potency and Efficacy of DNA Donors for Precision Genome Editing", bioRxiv, 2018, 31 pages.
International Search Report and Written Opinion for Application No. PCT/US2021/042733 dated Jan. 3, 2022 (23 pages).
International Preliminary Report on Patentability for Application No. PCT/US2020/040621 dated Dec. 28, 2021 (7 pages).
European Patent Office Extended European Search Report for application 20835024.9, mailed on Sep. 22, 2022 (10 pages).
Brinkman, E.K. et al. "Rapid quantitative evaluation of CRISPR genome editing by Tide and Tider." (Chapter 3 of Yonglun Luo, CRISPR Gene Editing: Methods and Protocols, Methods in Molecular Biology, vol. 1961), (Mar. 2019): 29-44.
International Preliminary Report on Patentability for Application No. PCT/US2021/0472733 dated Jan. 24, 2023 (12 pages).
Stojmirović, A., et al. "The effectiveness of position-and composition-specific gap costs for protein similarity searches." Bioinformatics 24.13 (2008): i15-i23.
Wang, Y., et al. "Systematic evaluation of CRISPR-Cas systems reveals design principles for genome editing in human cells." Genome biology 19 (2018): 1-16.
Wang Z et al. Biotechnol. Nov. 17, 2011;11:109 (Year: 2011).
Faircloth BC et al. PLoS One. 2012;7(8):e42543 (Year: 2012).
International Search Report and Written Opinion for Application No. PCT/US2023/066917 dated Aug. 10, 2023 (13 pages).
Karst, S. M., et al. "High-accuracy long-read amplicon sequences using unique molecular identifiers with Nanopore or PacBio sequencing." Nature methods 18.2 (2021): 165-169.
Clement, K., et al. "CRISPResso2 provides accurate and rapid genome editing sequence analysis." Nature biotechnology 37.3 (2019): 224-226.
Claudel-Renard, C., et al. "Enzyme-specific profiles for genome annotation: PRIAM." Nucleic acids research 31.22 (2003): 6633-6639.
China National Intellectual Property Administration Notification of First Office Action for application 202080074468.9, dated Aug. 31, 2023 (19 pages with translation).
NCBI Blast Search Results report conducted Nov. 8, 2023 showing zero identity resutls (Year: 2023) (1 page).
China National Intellectual Property Administration Notification of Second Office Action for application 202080074468.9, dated Jan. 25, 2024 (15 pages with translation).
NCBI Blast Search Result 2 (NCBI Blast database search, performed Mar. 28, 2024 (Year: 2024) (1 page).
Regier, J. C. et al. "Increased yield of PCR product from degenerate primers with nondegenerate, nonhomologous 5' tails." BioTechniques 38.1 (2005): 34-38.
Japanese Patent Office. Notice of Reasons for Rejection for Application No. 2022-523896, dated Jul. 2, 2024 (15 pages with translation).
European Patent Office Partial European Search Report for Application 20878470.2, dated Jul. 24, 2024 (15 pages).
Orlando, S. J., et al. "Zinc-finger nuclease-driven targeted integration into mammalian genomes using donors with limited chromosomal homology."Nucleic acids research 38.15 (2010): e152-e152.
International Search Report and Written Opinion for Application No. PCT/US2024/020080 dated Aug. 26, 2024 (18 pages).

* cited by examiner

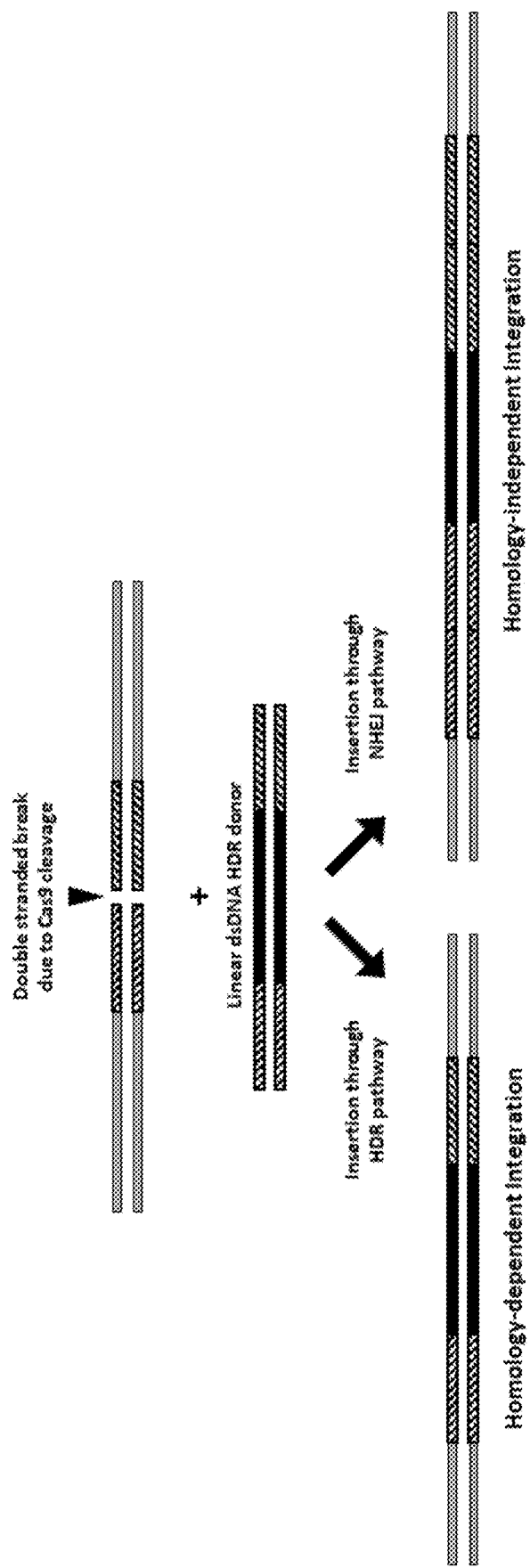

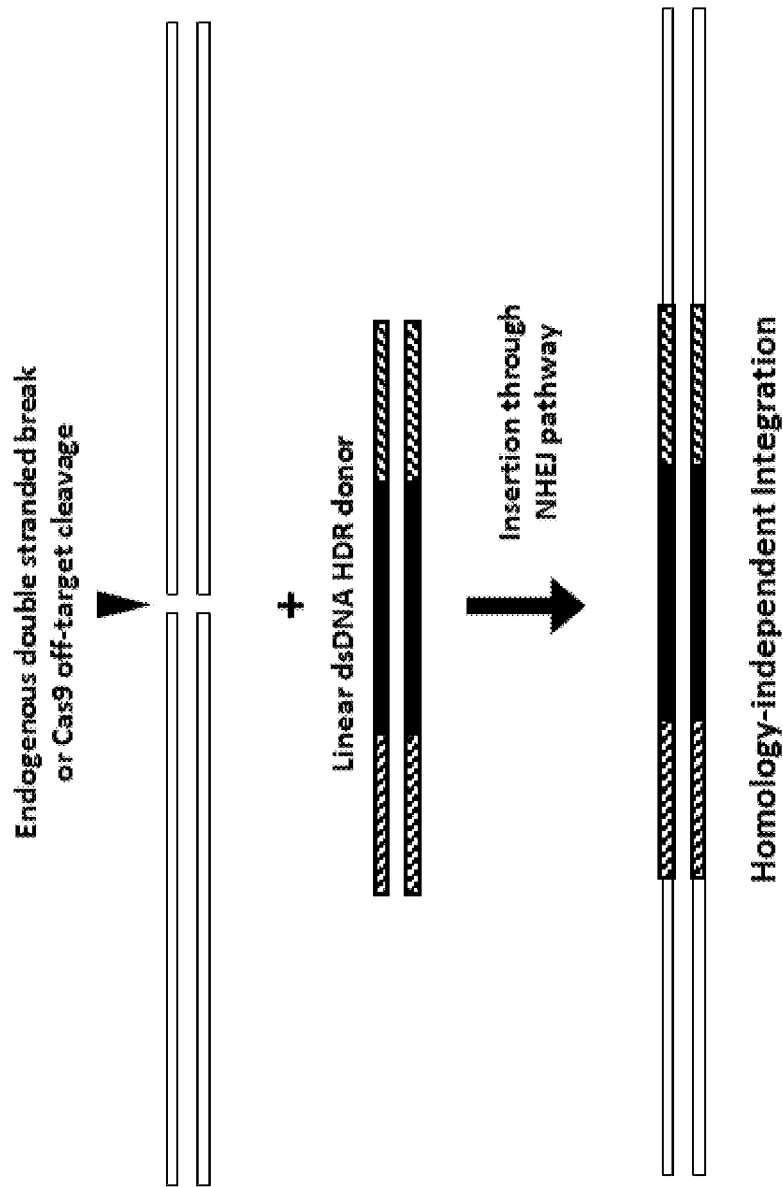

PCR round 1

Intermediate product

PCR round 2+

Final hairpin donor after PCR amplification

SEQUENCE LISTING

<160> NUMBER OF SEQ ID NOS: 235

<210> SEQ ID NO 1
<211> LENGTH: 1219
<212> TYPE: DNA
<213> ORGANISM: Artificial Sequence
<220> FEATURE:
<223> OTHER INFORMATION: Synthetic

<400> SEQUENCE: 1

```
gattgcctca gatcacacta tctccacttg cccagccctg tggaagatta gcggccatgt      60
attccaatgt gataggaact gtaacctctg gaaaaaggta cgaattcgag ggcagaggca     120
gtctgctgac atgcggtgac gtggaagaga atcccggccc ttctagaatg gttagcaagg     180
gcgaggagct gttcaccggg gtggtgccca tcctggtcga gctggacggc gacgtaaacg     240
gccacaagtt cagcgtgtcc ggcgagggcg agggcgatgc cacctacggc aagctgaccc     300
tgaagttcat ctgcaccacc ggcaagctgc ccgtgccctg gcccaccctc gtgaccaccc     360
tgacctacgg cgtgcagtgc ttcagccgct accccgacca catgaagcag cacgacttct     420
tcaagtccgc catgcccgaa ggctacgtcc aggagcgcac catcttcttc aaggacgacg     480
gcaactacaa gacccgcgcc gaggtgaagt tcgagggcga caccctggtg aaccgcatcg     540
agctgaaggg catcgacttc aaggaggacg gcaacatcct ggggcacaag cttgagtaca     600
actacaacag ccacaacgtc tatatcatgg ccgacaagca gaagaacggc atcaaggtga     660
acttcaagat ccgccacaac atcgaggacg gcagcgtgca gctcgccgac cactaccagc     720
agaacacccc catcggcgac ggccccgtgc tgctgcccga caaccactac ctgagcaccc     780
agtccgccct gagcaaagac cccaacgaga gcgcgatca catggtcctg ctggagttcg     840
tgaccgccgc cgggatcact ctcggcatgg acgagctgta caagtaactg tgccttctag     900
ttgccagcca tctgttgttt gcccctcccc cgtgccttcc ttgaccctgg aaggtgccac     960
tcccactgtc ctttcctaat aaaatgagga aattgcatcg cattgtctga gtaggtgtca    1020
ttctattctg gggggtgggg tggggcagga cagcaagggg gaggattggg aagacaatag    1080
caggcatgct ggggatgcgg tgggctctat ggcggtacca gaggggtgag ctttccctt     1140
gcctgcccct actgggtttt gtgacctcca aaggactcac aggaatgacc tccaacacct    1200
ttgagaagac caggccctc                                                 1219
```

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2

```
gattgcctca gatcacacta tctcc                                            25
```

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3

```
gagggcctgg tcttctcaaa g                                                21
```

```
<210> SEQ ID NO 4
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 4
gattgcctca gatcacacta tctcc                                              25

<210> SEQ ID NO 5
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 5
gagggcctgg tcttctcaaa g                                                  21

<210> SEQ ID NO 6
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 6
gattgcctca gatcacacta tctcc                                              25

<210> SEQ ID NO 7
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 7
gagggcctgg tcttctcaaa g                                                  21

<210> SEQ ID NO 8
<211> LENGTH: 25
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage

<400> SEQUENCE: 8
gattgcctca gatcacacta tctcc                                              25

<210> SEQ ID NO 9
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage

<400> SEQUENCE: 9
gagggcctgg tcttctcaaa g                                                  21

<210> SEQ ID NO 10
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage
<220> FEATURE:
<221> NAME/KEY: misc_feature
<222> LOCATION: (6)..(7)
<223> OTHER INFORMATION: Phosphorothioate 5'-3' linkage

<400> SEQUENCE: 10
gattgcctca gatcacacta tctcc                                              25

<210> SEQ ID NO 11
<211> LENGTH: 21
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage
<220> FEATURE:
<221> NAME/KEY: misc_feature
<222> LOCATION: (6)..(7)
<223> OTHER INFORMATION: Phosphorothioate 5'-3' linkage

<400> SEQUENCE: 11
gagggcctgg tcttctcaaa g                                    21

<210> SEQ ID NO 12
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-TEG (triethylene glycol)

<400> SEQUENCE: 12
gattgcctca gatcacacta tctcc                                25

<210> SEQ ID NO 13
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-TEG (triethylene glycol)

<400> SEQUENCE: 13
gagggcctgg tcttctcaaa g                                    21

<210> SEQ ID NO 14
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-locked (2'-oxygen-4'-carbon methylene
      linkage)

<400> SEQUENCE: 14
```

```
gattgcctca gatcacacta tctcc                                              25

<210> SEQ ID NO 15
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-locked (2'-oxygen-4'-carbon methylene
      linkage)

<400> SEQUENCE: 15
gagggcctgg tcttctcaaa g                                                  21

<210> SEQ ID NO 16
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-Sp18 (hexaethylene glycol)

<400> SEQUENCE: 16
gattgcctca gatcacacta tctcc                                              25

<210> SEQ ID NO 17
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-Sp18 (hexaethylene glycol)

<400> SEQUENCE: 17
gagggcctgg tcttctcaaa g                                                  21

<210> SEQ ID NO 18
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-SpC3 (1,3-propanediol)

<400> SEQUENCE: 18
gattgcctca gatcacacta tctcc                                              25

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
gagggcctgg tcttctcaaa g                                                  21
```

```
<210> SEQ ID NO 20
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 20
gattgcctca gatcacacta tctcc                                              25

<210> SEQ ID NO 21
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 21
gagggcctgg tcttctcaaa g                                                  21

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
acctctggaa aaaggtaaga                                                    20

<210> SEQ ID NO 23
<211> LENGTH: 19
<212> TYPE: DNA
<213> ORGANISM: Artificial Sequence
<220> FEATURE:
<223> OTHER INFORMATION: Synthetic

<400> SEQUENCE: 23
agaaccagtt ttcaggcgg                                                     19

<210> SEQ ID NO 24
<211> LENGTH: 17
<212> TYPE: DNA
<213> ORGANISM: Artificial Sequence
<220> FEATURE:
<223> OTHER INFORMATION: Synthetic

<400> SEQUENCE: 24
accgcatgtc agcagac                                                       17

<210> SEQ ID NO 25
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

```
<223> OTHER INFORMATION: 5'-FAM (5,6 fluorescein dye)
<220> FEATURE:
<221> NAME/KEY: misc_feature
<222> LOCATION: (9)..(10)
<223> OTHER INFORMATION: ZEN fluorescent quencher is located between G9
      and G10
<220> FEATURE:
<221> NAME/KEY: misc_feature
<222> LOCATION: (27)..(27)
<223> OTHER INFORMATION: 3'-FQ (Iowa Black FQ fluorescent quencher)

<400> SEQUENCE: 25
tggaaaaagg tacgaattcg agggca                                          26

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
cgctaatctt ccacaggg                                                   18

<210> SEQ ID NO 27
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-FAM (5,6 fluorescein dye)
<220> FEATURE:
<221> NAME/KEY: misc_feature
<222> LOCATION: (9)..(10)
<223> OTHER INFORMATION: ZEN fluorescent quencher is located between A9
      and A10
<220> FEATURE:
<221> NAME/KEY: misc_feature
<222> LOCATION: (30)..(30)
<223> OTHER INFORMATION: 3'-FQ (Iowa Black FQ fluorescent quencher)

<400> SEQUENCE: 27
tctggaaaaa ggtagattgc ctcagatca                                       29

<210> SEQ ID NO 28
<211> LENGTH: 122
<212> TYPE: DNA
<213> ORGANISM: Artificial Sequence
<220> FEATURE:
<223> OTHER INFORMATION: Synthetic

<400> SEQUENCE: 28
attccaatgt gataggaact gtaacctctg gaaaaggta gaattcttag ctctgtttac      60
gtcccagcgg gcatgagagt aaagaggggt gagctttccc cttgcctgcc cctactgggt    120
tt                                                                   122

<210> SEQ ID NO 29
<211> LENGTH: 26
<212> TYPE: DNA
<213> ORGANISM: Artificial Sequence
<220> FEATURE:
<223> OTHER INFORMATION: Synthetic

<400> SEQUENCE: 29
attccaatgt gataggaact gtaacc                                          26
```

```
<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
aaacccagta ggggcaggc                                               19

<210> SEQ ID NO 31
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 31
attccaatgt gataggaact gtaacc                                       26

<210> SEQ ID NO 32
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 32
aaacccagta ggggcaggc                                               19

<210> SEQ ID NO 33
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified 5-methyluridine
      (ribothymidine)
<220> FEATURE:
<221> NAME/KEY: misc_feature
<222> LOCATION: (3)..(3)
<223> OTHER INFORMATION: 2'-O-methoxyethyl modified 5-methyluridine
      (ribothymidine)

<400> SEQUENCE: 33
attccaatgt gataggaact gtaacc                                       26

<210> SEQ ID NO 34
<211> LENGTH: 19
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboadenosine
<220> FEATURE:
<221> NAME/KEY: misc_feature
<222> LOCATION: (3)..(3)
<223> OTHER INFORMATION: 2'-O-methoxyethyl modified riboadenosine

<400> SEQUENCE: 34
aaacccagta ggggcaggc                                                19

<210> SEQ ID NO 35
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage
<220> FEATURE:
<221> NAME/KEY: misc_feature
<222> LOCATION: (6)..(7)
<223> OTHER INFORMATION: Phosphorothioate 5'-3' linkage

<400> SEQUENCE: 35
attccaatgt gataggaact gtaacctctg                                    30

<210> SEQ ID NO 36
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

```
<220> FEATURE:
<221> NAME/KEY: misc_feature
<222> LOCATION: (6)..(7)
<223> OTHER INFORMATION: Phosphorothioate 5'-3' linkage

<400> SEQUENCE: 36
aaacccagta ggggcaggc                                                        19

<210> SEQ ID NO 37
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 37
attccaatgt gataggaact gtaacc                                                26

<210> SEQ ID NO 38
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 38
aaacccagta ggggcaggc                                                        19

<210> SEQ ID NO 39
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-Sp18 (hexaethylene glycol)

<400> SEQUENCE: 39
attccaatgt gataggaact gtaacc                                                26

<210> SEQ ID NO 40
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-Sp18 (hexaethylene glycol)

<400> SEQUENCE: 40
aaacccagta ggggcaggc                                                        19

<210> SEQ ID NO 41
<211> LENGTH: 30
<212> TYPE: DNA
<213> ORGANISM: Artificial Sequence
<220> FEATURE:
```

<223> OTHER INFORMATION: Synthetic
<220> FEATURE:
<221> NAME/KEY: misc_feature
<222> LOCATION: (3)..(3)
<223> OTHER INFORMATION: 2'-O-methoxyethyl modified 5-methyluridine
      (ribothymidine)

<400> SEQUENCE: 41
attccaatgt gataggaact gtaacctctg                                      30

<210> SEQ ID NO 42
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 2'-O-methoxyethyl modified riboadenosine

<400> SEQUENCE: 42
aaacccagta ggggcaggc                                                  19

<210> SEQ ID NO 43
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 2'-O-methoxyethyl modified ribocytidine

<400> SEQUENCE: 43
attccaatgt gataggaact gtaacctctg                                      30

<210> SEQ ID NO 44
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: 2'-O-methoxyethyl modified ribocytidine

<400> SEQUENCE: 44
aaacccagta ggggcaggc                                                  19

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
cttgtccctc tttgccttct ct                                              22

<210> SEQ ID NO 46
<211> LENGTH: 22
<212> TYPE: DNA
<213> ORGANISM: Artificial Sequence
<220> FEATURE:
<223> OTHER INFORMATION: Synthetic

```
<400> SEQUENCE: 46
gggtggatct gagtggaaga aa                                              22

<210> SEQ ID NO 47
<211> LENGTH: 142
<212> TYPE: DNA
<213> ORGANISM: Artificial Sequence
<220> FEATURE:
<223> OTHER INFORMATION: Synthetic

<400> SEQUENCE: 47
gcggccatgt attccaatgt gataggaact gtaacctctg gaaaaggta gaattcttag      60 ctctgtttac gtcccagcgg gcatgagagt aaagagggt gagctttccc cttgcctgcc    120
cctactgggt tttgtgacct cc                                             142

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
gcggccatgt attccaatgt g                                               21

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
ggaggtcaca aaacccagta gg                                              22

<210> SEQ ID NO 50
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 50
gcggccatgt attccaatgt g                                               21

<210> SEQ ID NO 51
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 51
ggaggtcaca aaacccagta gg                                              22

<210> SEQ ID NO 52
<211> LENGTH: 21
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage
<220> FEATURE:
<221> NAME/KEY: misc_feature
<222> LOCATION: (6)..(7)
<223> OTHER INFORMATION: Phosphorothioate 5'-3' linkage

<400> SEQUENCE: 52
gcggccatgt attccaatgt g                                         21

<210> SEQ ID NO 53
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage
<220> FEATURE:
<221> NAME/KEY: misc_feature
<222> LOCATION: (6)..(7)
<223> OTHER INFORMATION: Phosphorothioate 5'-3' linkage

<400> SEQUENCE: 53
ggaggtcaca aaacccagta gg                                        22

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
```
cctctaaggt ttgcttacga                                                  20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
aattatgggg attactagga                                                  20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gccaaggact caaacccaga                                                  20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
ccccgttctc ctgtggattc                                                  20

<210> SEQ ID NO 58
<211> LENGTH: 27
<212> TYPE: DNA
<213> ORGANISM: Artificial Sequence
<220> FEATURE:
<223> OTHER INFORMATION: Synthetic

<400> SEQUENCE: 58
aagaatgttg tgataaaagg tgatgct                                          27

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
acacatccat gggacttctg cctc                                             24

<210> SEQ ID NO 60
<211> LENGTH: 66
<212> TYPE: DNA
<213> ORGANISM: Artificial Sequence
<220> FEATURE:
<223> OTHER INFORMATION: Synthetic

<400> SEQUENCE: 60
gataggaact gtaacctctg gaaaaggta gaattcagag gggtgagctt tccccttgcc      60
tgcccc                                                                 66

<210> SEQ ID NO 61
<211> LENGTH: 66

```
<212> TYPE: DNA
<213> ORGANISM: Artificial Sequence
<220> FEATURE:
<223> OTHER INFORMATION: Synthetic

<400> SEQUENCE: 61
ggggcaggca aggggaaagc tcacccctct gaattctacc tttttccaga ggttacagtt     60
cctatc                                                               66

<210> SEQ ID NO 62
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (1)..(10)
<223> OTHER INFORMATION: Hairpin Region

<400> SEQUENCE: 62
tcgttttcga dataggaact gtaacctctg gaaaaaggta gaattcagag gggtgagctt     60
tccccttgcc tgcccc                                                    76

<210> SEQ ID NO 63
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (1)..(10)
<223> OTHER INFORMATION: Hairpin Region

<400> SEQUENCE: 63
tcgttttcga ggggcaggca aggggaaagc tcacccctct gaattctacc tttttccaga     60
ggttacagtt cctatc                                                    76

<210> SEQ ID NO 64
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)
<220> FEATURE:
<221> NAME/KEY: misc_feature
<222> LOCATION: (1)..(10)
<223> OTHER INFORMATION: Hairpin Region
<220> FEATURE:
<221> NAME/KEY: misc_feature
<222> LOCATION: (2)..(2)
<223> OTHER INFORMATION: 2'-O-methoxyethyl modified ribocytidine
```

-continued

```
<220> FEATURE:
<221> NAME/KEY: misc_feature
<222> LOCATION: (3)..(3)
<223> OTHER INFORMATION: 2'-O-methoxyethyl modified riboguanosine
<220> FEATURE:
<221> NAME/KEY: misc_feature
<222> LOCATION: (4)..(4)
<223> OTHER INFORMATION: 2'-O-methoxyethyl modified 5-methyluridine
      (ribothymidine)
<220> FEATURE:
<221> NAME/KEY: misc_feature
<222> LOCATION: (5)..(5)
<223> OTHER INFORMATION: 2'-O-methoxyethyl modified 5-methyluridine
      (ribothymidine)
<220> FEATURE:
<221> NAME/KEY: misc_feature
<222> LOCATION: (6)..(6)
<223> OTHER INFORMATION: 2'-O-methoxyethyl modified 5-methyluridine
      (ribothymidine)
<220> FEATURE:
<221> NAME/KEY: misc_feature
<222> LOCATION: (7)..(7)
<223> OTHER INFORMATION: 2'-O-methoxyethyl modified 5-methyluridine
      (ribothymidine)
<220> FEATURE:
<221> NAME/KEY: misc_feature
<222> LOCATION: (8)..(8)
<223> OTHER INFORMATION: 2'-O-methoxyethyl modified ribocytidine
<220> FEATURE:
<221> NAME/KEY: misc_feature
<222> LOCATION: (9)..(9)
<223> OTHER INFORMATION: 2'-O-methoxyethyl modified riboguanosine
<220> FEATURE:
<221> NAME/KEY: misc_feature
<222> LOCATION: (10)..(10)
<223> OTHER INFORMATION: 2'-O-methoxyethyl modified riboadenosine

<400> SEQUENCE: 64
tcgttttcga gataggaact gtaacctctg gaaaaaggta gaattcagag gggtgagctt     60
tccccttgcc tgcccc                                                    76

<210> SEQ ID NO 65
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-phosphate modification
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)
<220> FEATURE:
<221> NAME/KEY: misc_feature
<222> LOCATION: (1)..(10)
<223> OTHER INFORMATION: Hairpin Region
<220> FEATURE:
<221> NAME/KEY: misc_feature
<222> LOCATION: (2)..(2)
<223> OTHER INFORMATION: 2'-O-methoxyethyl modified ribocytidine
<220> FEATURE:
<221> NAME/KEY: misc_feature
<222> LOCATION: (3)..(3)
<223> OTHER INFORMATION: 2'-O-methoxyethyl modified riboguanosine
<220> FEATURE:
<221> NAME/KEY: misc_feature
<222> LOCATION: (4)..(4)
<223> OTHER INFORMATION: 2'-O-methoxyethyl modified 5-methyluridine
      (ribothymidine)
<220> FEATURE:
<221> NAME/KEY: misc_feature
<222> LOCATION: (5)..(5)
```

```
<223> OTHER INFORMATION: 2'-O-methoxyethyl modified 5-methyluridine
      (ribothymidine)
<220> FEATURE:
<221> NAME/KEY: misc_feature
<222> LOCATION: (6)..(6)
<223> OTHER INFORMATION: 2'-O-methoxyethyl modified 5-methyluridine
      (ribothymidine)
<220> FEATURE:
<221> NAME/KEY: misc_feature
<222> LOCATION: (7)..(7)
<223> OTHER INFORMATION: 2'-O-methoxyethyl modified 5-methyluridine
      (ribothymidine)
<220> FEATURE:
<221> NAME/KEY: misc_feature
<222> LOCATION: (8)..(8)
<223> OTHER INFORMATION: 2'-O-methoxyethyl modified ribocytidine
<220> FEATURE:
<221> NAME/KEY: misc_feature
<222> LOCATION: (9)..(9)
<223> OTHER INFORMATION: 2'-O-methoxyethyl modified riboguanosine
<220> FEATURE:
<221> NAME/KEY: misc_feature
<222> LOCATION: (10)..(10)
<223> OTHER INFORMATION: 2'-O-methoxyethyl modified riboadenosine

<400> SEQUENCE: 65
tcgttttcga ggggcaggca aggggaaagc tcacccctct gaattctacc tttttccaga    60
ggttacagtt cctatc                                                   76

<210> SEQ ID NO 66
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Non-template 2'-O-methoxyethyl modified
      riboadenosine

<400> SEQUENCE: 66
agataggaac tgtaacctct ggaaaaaggt agaattcaga ggggtgagct ttccccttgc    60
ctgcccc                                                             67

<210> SEQ ID NO 67
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Non-template 2'-O-methoxyethyl modified
      riboadenosine

<400> SEQUENCE: 67
aggggcaggc aaggggaaag ctcacccctc tgaattctac cttttttccag aggttacagt    60 tcctatc                                                             67

<210> SEQ ID NO 68
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 68
attccaatgt gataggaact gtaacc                                          26

<210> SEQ ID NO 69
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 69
aaacccagta ggggcaggc                                                  19

<210> SEQ ID NO 70
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-riboadenosine

<400> SEQUENCE: 70
attccaatgt gataggaact gtaacc                                          26

<210> SEQ ID NO 71
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-riboadenosine

<400> SEQUENCE: 71
aaacccagta ggggcaggc                                                  19

<210> SEQ ID NO 72
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature

```
<222> LOCATION: (1)..(1)
<223> OTHER INFORMATION: 5'-locked (2'-oxygen-4'-carbon methylene
      linkage)

<400> SEQUENCE: 72
attccaatgt gataggaact gtaacc                                           26

<210> SEQ ID NO 73
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-locked (2'-oxygen-4'-carbon methylene
      linkage)

<400> SEQUENCE: 73
aaacccagta ggggcaggc                                                  19

<210> SEQ ID NO 74
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl modified riboadenosine

<400> SEQUENCE: 74
attccaatgt gataggaact gtaacc                                           26

<210> SEQ ID NO 75
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2'-O-methyl modified riboadenosine

<400> SEQUENCE: 75
aaacccagta ggggcaggc                                                  19

<210> SEQ ID NO 76
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-fluoro modified riboadenosine

<400> SEQUENCE: 76
attccaatgt gataggaact gtaacc                                           26

<210> SEQ ID NO 77
<211> LENGTH: 19
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: 2'-fluoro modified riboadenosine

<400> SEQUENCE: 77
aaacccagta ggggcaggc                                                 19

<210> SEQ ID NO 78
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Non-template 2'-O-methoxyethyl modified
      riboguanosine

<400> SEQUENCE: 78
gattccaatg tgataggaac tgtaacc                                        27

<210> SEQ ID NO 79
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Non-template 2'-O-methoxyethyl modified
      riboguanosine

<400> SEQUENCE: 79
gaaacccagt aggggcaggc                                                20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
tgccctggta acggccaaag                                                20

<210> SEQ ID NO 81
<211> LENGTH: 21
<212> TYPE: DNA
<213> ORGANISM: Artificial Sequence
<220> FEATURE:
<223> OTHER INFORMATION: Synthetic

<400> SEQUENCE: 81
tcggacagaa aggcattcac a                                              21

<210> SEQ ID NO 82
<211> LENGTH: 24
<212> TYPE: DNA
<213> ORGANISM: Artificial Sequence
<220> FEATURE:
<223> OTHER INFORMATION: Synthetic

<400> SEQUENCE: 82
caacggcaaa gggagaactt aaac                                           24
```

<210> SEQ ID NO 83
<211> LENGTH: 122
<212> TYPE: DNA
<213> ORGANISM: Artificial Sequence
<220> FEATURE:
<223> OTHER INFORMATION: Synthetic

<400> SEQUENCE: 83
agtgccttgt ctgtagtgtc aactcattgc tgccccttcc gaattcttag ctctgtttac     60
gtcccagcgg gcatgagagt aatagtaatc cccataattt agctctccat ttcatagtct    120
tt                                                                   122

<210> SEQ ID NO 84
<211> LENGTH: 122
<212> TYPE: DNA
<213> ORGANISM: Artificial Sequence
<220> FEATURE:
<223> OTHER INFORMATION: Synthetic

<400> SEQUENCE: 84
aaggaggagg cctaaggatg gggcttttct gtcaccaatc gaattcttag ctctgtttac     60
gtcccagcgg gcatgagagt aactgtccct agtggcccca ctgtggggtg gaggggacag    120
at                                                                   122

<210> SEQ ID NO 85
<211> LENGTH: 122
<212> TYPE: DNA
<213> ORGANISM: Artificial Sequence
<220> FEATURE:
<223> OTHER INFORMATION: Synthetic

<400> SEQUENCE: 85
tgccaagctc tccctcccag gatcctctct ggctccatcg gaattcttag ctctgtttac     60
gtcccagcgg gcatgagagt aataagcaaa ccttagaggt tctggcaagg agagagatgg    120
ct                                                                   122

<210> SEQ ID NO 86
<211> LENGTH: 122
<212> TYPE: DNA
<213> ORGANISM: Artificial Sequence
<220> FEATURE:
<223> OTHER INFORMATION: Synthetic

<400> SEQUENCE: 86
aggccaatgg ggaggacatc gatgtcacct ccaatgacta gaattcttag ctctgtttac     60
gtcccagcgg gcatgagagt aagggtgggc aaccacaaac ccacgagggc agagtgctgc    120
tt                                                                   122

<210> SEQ ID NO 87
<211> LENGTH: 21
<212> TYPE: DNA
<213> ORGANISM: Artificial Sequence
<220> FEATURE:
<223> OTHER INFORMATION: Synthetic

<400> SEQUENCE: 87
agtgccttgt ctgtagtgtc a                                               21

<210> SEQ ID NO 88
<211> LENGTH: 30

```
<212> TYPE: DNA
<213> ORGANISM: Artificial Sequence
<220> FEATURE:
<223> OTHER INFORMATION: Synthetic

<400> SEQUENCE: 88
aaagactatg aaatggagag ctaaattatg                                    30

<210> SEQ ID NO 89
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 89
agtgccttgt ctgtagtgtc a                                             21

<210> SEQ ID NO 90
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 90
aaagactatg aaatggagag ctaaattatg                                    30

<210> SEQ ID NO 91
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 91
agtgccttgt ctgtagtgtc a                                             21

<210> SEQ ID NO 92
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 92
```
aaagactatg aaatggagag ctaaattatg                                30

<210> SEQ ID NO 93
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 93
agtgccttgt ctgtagtgtc a                                         21

<210> SEQ ID NO 94
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 94
aaagactatg aaatggagag ctaaattatg                                30

<210> SEQ ID NO 95
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 95
agtgccttgt ctgtagtgtc a                                         21

<210> SEQ ID NO 96
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 96
aaagactatg aaatggagag ctaaattatg                                30

<210> SEQ ID NO 97
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified 5-methyluridine
      (ribothymidine)

<400> SEQUENCE: 97
agtgccttgt ctgtagtgtc a                                         21

<210> SEQ ID NO 98
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboadenosine
<220> FEATURE:
<221> NAME/KEY: misc_feature
<222> LOCATION: (3)..(3)
<223> OTHER INFORMATION: 2'-O-methoxyethyl modified riboadenosine

<400> SEQUENCE: 98
aaagactatg aaatggagag ctaaattatg                                30

<210> SEQ ID NO 99
<211> LENGTH: 21
<212> TYPE: DNA
<213> ORGANISM: Artificial Sequence
<220> FEATURE:
<223> OTHER INFORMATION: Synthetic

<400> SEQUENCE: 99
aaggaggagg cctaaggatg g                                         21

<210> SEQ ID NO 100
<211> LENGTH: 18
<212> TYPE: DNA
<213> ORGANISM: Artificial Sequence
<220> FEATURE:
<223> OTHER INFORMATION: Synthetic

<400> SEQUENCE: 100
atctgtcccc tccacccc                                             18

<210> SEQ ID NO 101
<211> LENGTH: 21

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 101
aaggaggagg cctaaggatg g                                              21

<210> SEQ ID NO 102
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 102
atctgtcccc tccacccc                                                  18

<210> SEQ ID NO 103
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 103
aaggaggagg cctaaggatg g                                              21

<210> SEQ ID NO 104
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 104
atctgtcccc tccacccc                                                  18

<210> SEQ ID NO 105
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

```
<223> OTHER INFORMATION: 2'-O-methoxyethyl modified riboadenosine

<400> SEQUENCE: 105
aaggaggagg cctaaggatg g                                              21

<210> SEQ ID NO 106
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 106
atctgtcccc tccacccc                                                  18

<210> SEQ ID NO 107
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 107
aaggaggagg cctaaggatg g                                              21

<210> SEQ ID NO 108
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 108
atctgtcccc tccacccc                                                  18

<210> SEQ ID NO 109
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboadenosine
<220> FEATURE:
<221> NAME/KEY: misc_feature
<222> LOCATION: (3)..(3)
<223> OTHER INFORMATION: 2'-O-methoxyethyl modified riboadenosine

<400> SEQUENCE: 109
aaggaggagg cctaaggatg g                                         21

<210> SEQ ID NO 110
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified 5-methyluridine
      (ribothymidine)
<220> FEATURE:
<221> NAME/KEY: misc_feature
<222> LOCATION: (3)..(3)
<223> OTHER INFORMATION: 2'-O-methoxyethyl modified ribocytidine

<400> SEQUENCE: 110
atctgtcccc tccacccc                                             18

<210> SEQ ID NO 111
<211> LENGTH: 18
<212> TYPE: DNA
<213> ORGANISM: Artificial Sequence
<220> FEATURE:
<223> OTHER INFORMATION: Synthetic

<400> SEQUENCE: 111
tgccaagctc tccctccc                                             18

<210> SEQ ID NO 112
<211> LENGTH: 21
<212> TYPE: DNA
<213> ORGANISM: Artificial Sequence
<220> FEATURE:
<223> OTHER INFORMATION: Synthetic

<400> SEQUENCE: 112
agccatctct ctccttgcca g                                         21

<210> SEQ ID NO 113
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
```

<400> SEQUENCE: 113
tgccaagctc tccctccc                                                      18

<210> SEQ ID NO 114
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 114
agccatctct ctccttgcca g                                                  21

<210> SEQ ID NO 115
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 115
tgccaagctc tccctccc                                                      18

<210> SEQ ID NO 116
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 116
agccatctct ctccttgcca g                                                  21

<210> SEQ ID NO 117
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)

<400> SEQUENCE: 117
tgccaagctc tccctccc                                                      18

<210> SEQ ID NO 118
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 2'-O-methoxyethyl modified riboadenosine

<400> SEQUENCE: 118
agccatctct ctccttgcca g                                              21

<210> SEQ ID NO 119
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 119
tgccaagctc tccctccc                                                  18

<210> SEQ ID NO 120
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 120
agccatctct ctccttgcca g                                              21

<210> SEQ ID NO 121
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified ribocytidine

```
<400> SEQUENCE: 121
tgccaagctc tccctccc                                                    18

<210> SEQ ID NO 122
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified ribocytidine

<400> SEQUENCE: 122
agccatctct ctccttgcca g                                                21

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
aggccaatgg ggaggacatc                                                  20

<210> SEQ ID NO 124
<211> LENGTH: 19
<212> TYPE: DNA
<213> ORGANISM: Artificial Sequence
<220> FEATURE:
<223> OTHER INFORMATION: Synthetic

<400> SEQUENCE: 124
aagcagcact ctgccctcg                                                   19

<210> SEQ ID NO 125
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 125
aggccaatgg ggaggacatc                                                  20

<210> SEQ ID NO 126
<211> LENGTH: 19
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 126
aagcagcact ctgccctcg                                               19

<210> SEQ ID NO 127
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 127
aggccaatgg ggaggacatc                                              20

<210> SEQ ID NO 128
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin

<400> SEQUENCE: 128
aagcagcact ctgccctcg                                               19

<210> SEQ ID NO 129
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 129
aggccaatgg ggaggacatc                                              20

<210> SEQ ID NO 130
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 130
aagcagcact ctgccctcg                                               19
```

```
<210> SEQ ID NO 131
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 131
aggccaatgg ggaggacatc                                                 20

<210> SEQ ID NO 132
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage

<400> SEQUENCE: 132
aagcagcact ctgccctcg                                                  19

<210> SEQ ID NO 133
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified riboguanosine

<400> SEQUENCE: 133
aggccaatgg ggaggacatc                                                 20

<210> SEQ ID NO 134
<211> LENGTH: 19
<212> TYPE: DNA
<213> ORGANISM: Artificial Sequence
<220> FEATURE:
<223> OTHER INFORMATION: Synthetic
<220> FEATURE:
```

-continued

```
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboadenosine
<220> FEATURE:
<221> NAME/KEY: misc_feature
<222> LOCATION: (3)..(3)
<223> OTHER INFORMATION: 2'-O-methoxyethyl modified riboguanosine

<400> SEQUENCE: 134
aagcagcact ctgccctcg                                                19

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
aattatgggg attactagga                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
ggggccacta gggacaggat                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
cctctaaggt ttgcttacga                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
gtcacctcca atgactaggg                                               20

<210> SEQ ID NO 139
<211> LENGTH: 53
<212> TYPE: DNA
<213> ORGANISM: Artificial Sequence
<220> FEATURE:
<223> OTHER INFORMATION: Synthetic

<400> SEQUENCE: 139
acactctttc cctacacgac gctcttccga tctcagaact gtccttcagg ttc          53

<210> SEQ ID NO 140
<211> LENGTH: 55
```

-continued

<212> TYPE: DNA
<213> ORGANISM: Artificial Sequence
<220> FEATURE:
<223> OTHER INFORMATION: Synthetic

<400> SEQUENCE: 140
gtgactggag ttcagacgtg tgctcttccg atctcactgt ttcatttcat ccgtg        55

<210> SEQ ID NO 141
<211> LENGTH: 54
<212> TYPE: DNA
<213> ORGANISM: Artificial Sequence
<220> FEATURE:
<223> OTHER INFORMATION: Synthetic

<400> SEQUENCE: 141
acactctttc cctacacgac gctcttccga tctgagagat ggctccagga aatg         54

<210> SEQ ID NO 142
<211> LENGTH: 55
<212> TYPE: DNA
<213> ORGANISM: Artificial Sequence
<220> FEATURE:
<223> OTHER INFORMATION: Synthetic

<400> SEQUENCE: 142
gtgactggag ttcagacgtg tgctcttccg atctcacttc aggacagcat gtttg        55

<210> SEQ ID NO 143
<211> LENGTH: 53
<212> TYPE: DNA
<213> ORGANISM: Artificial Sequence
<220> FEATURE:
<223> OTHER INFORMATION: Synthetic

<400> SEQUENCE: 143
acactctttc cctacacgac gctcttccga tctgatcagt gaaacgcacc aga          53

<210> SEQ ID NO 144
<211> LENGTH: 58
<212> TYPE: DNA
<213> ORGANISM: Artificial Sequence
<220> FEATURE:
<223> OTHER INFORMATION: Synthetic

<400> SEQUENCE: 144
gtgactggag ttcagacgtg tgctcttccg atctcctcct tcctagtctc ctgatatt     58

<210> SEQ ID NO 145
<211> LENGTH: 52
<212> TYPE: DNA
<213> ORGANISM: Artificial Sequence
<220> FEATURE:
<223> OTHER INFORMATION: Synthetic

<400> SEQUENCE: 145
acactctttc cctacacgac gctcttccga tctagaagaa gagggctcc ca            52

<210> SEQ ID NO 146
<211> LENGTH: 51
<212> TYPE: DNA
<213> ORGANISM: Artificial Sequence
<220> FEATURE:
<223> OTHER INFORMATION: Synthetic

<400> SEQUENCE: 146
gtgactggag ttcagacgtg tgctcttccg atctcaggga gtggccagag t        51

<210> SEQ ID NO 147
<211> LENGTH: 502
<212> TYPE: DNA
<213> ORGANISM: Artificial Sequence
<220> FEATURE:
<223> OTHER INFORMATION: Synthetic

<400> SEQUENCE: 147
gattgcctca gatcacacta tctccacttg cccagccctg tggaagatta gcggccatgt        60
attccaatgt gataggaact gtaacctctg gaaaaaggta cgaattcgag ggcagaggca       120
gtctgctgac atgcggtgac gtggaagaga atcccggccc ttctagataa ctgtgccttc       180
tagttgccag ccatctgttg tttgcccctc ccccgtgcct tccttgaccc tggaaggtgc       240
cactcccact gtcctttcct aataaaatga ggaaattgca tcgcattgtc tgagtaggtg       300
tcattctatt ctgggggtg gggtggggca ggacagcaag ggggaggatt gggaagacaa       360
tagcaggcat gctgggatg cggtgggctc tatggcggta ccagggggt gagctttccc         420
cttgcctgcc cctactgggt tttgtgacct ccaaaggact cacaggaatg acctccaaca       480
cctttgagaa gaccaggccc tc                                                502

<210> SEQ ID NO 148
<211> LENGTH: 700
<212> TYPE: DNA
<213> ORGANISM: Artificial Sequence
<220> FEATURE:
<223> OTHER INFORMATION: Synthetic

<400> SEQUENCE: 148
gattgcctca gatcacacta tctccacttg cccagccctg tggaagatta gcggccatgt        60
attccaatgt gataggaact gtaacctctg gaaaaaggta cgaattcgag ggcagaggca       120
gtctgctgac atgcggtgac gtggaagaga atcccggccc ttctagaatg gttagcaagg       180
gcgaggagct gttcaccggg gtggtgccca tcctggtcga gctggacggc gacgtaaacg       240
gccacaagtt cagcgtgtcc ggcgagggcg agggcgatgc cacctacggc aagctgaccc       300
tgaagttcat ctgcaccacc ggcaagctgc ccgtgccctg gcccaccctc gtgaccaccc       360
tgacctaact gtgccttcta gttgccagcc atctgttgtt tgcccctccc ccgtgccttc       420
cttgaccctg gaaggtgcca ctcccactgt cctttcctaa taaaatgagg aaattgcatc       480
gcattgtctg agtaggtgtc attctattct ggggggtgg gtgggcagg acagcaaggg         540
ggaggattgg gaagacaata gcaggcatgc tggggatgcg gtgggctcta tggcggtacc       600
agaggggtga gctttcccct tgcctgcccc tactgggttt tgtgacctcc aaaggactca       660
caggaatgac ctccaacacc tttgagaaga ccaggccctc                              700

<210> SEQ ID NO 149
<211> LENGTH: 1219
<212> TYPE: DNA
<213> ORGANISM: Artificial Sequence
<220> FEATURE:
<223> OTHER INFORMATION: Synthetic

<400> SEQUENCE: 149
gattgcctca gatcacacta tctccacttg cccagccctg tggaagatta gcggccatgt        60
attccaatgt gataggaact gtaacctctg gaaaaaggta cgaattcgag ggcagaggca       120
gtctgctgac atgcggtgac gtggaagaga atcccggccc ttctagaatg gttagcaagg       180

```
gcgaggagct gttcaccggg gtggtgccca tcctggtcga gctggacggc gacgtaaacg    240
gccacaagtt cagcgtgtcc ggcgagggcg agggcgatgc cacctacggc aagctgaccc    300
tgaagttcat ctgcaccacc ggcaagctgc ccgtgccctg gcccaccctc gtgaccaccc    360
tgacctacgg cgtgcagtgc ttcagccgct accccgacca catgaagcag cacgacttct    420
tcaagtccgc catgcccgaa ggctacgtcc aggagcgcac catcttcttc aaggacgacg    480
gcaactacaa gacccgcgcc gaggtgaagt tcgagggcga cacccggtg aaccgcatcg     540 agctgaaggg catcgacttc aaggaggacg gcaacatcct ggggcacaag cttgagtaca    600
actacaacag ccacaacgtc tatatcatgg ccgacaagca gaagaacggc atcaaggtga    660
acttcaagat ccgccacaac atcgaggacg gcagcgtgca gctcgccgac cactaccagc    720
agaacacccc catcggcgac ggccccgtgc tgctgcccga caaccactac ctgagcaccc    780
agtccgccct gagcaaagac cccaacgaga gcgcgatca catggtcctg ctggagttcg     840
tgaccgccgc cgggatcact ctcggcatgg acgagctgta caagtaactg tgccttctag    900
ttgccagcca tctgttgttt gcccctcccc cgtgccttcc ttgaccctgg aaggtgccac    960
tcccactgtc ctttcctaat aaaatgagga aattgcatcg cattgtctga gtaggtgtca    1020
ttctattctg ggggtgggg tggggcagga cagcaagggg gaggattggg aagacaatag    1080
caggcatgct ggggatgcgg tgggctctat ggcggtacca gagggtgag ctttccctt     1140 gcctgcccct actgggtttt gtgacctcca aaggactcac aggaatgacc tccaacacct    1200
ttgagaagac caggccctc                                                 1219
```

<210> SEQ ID NO 150
<211> LENGTH: 502
<212> TYPE: DNA
<213> ORGANISM: Artificial Sequence
<220> FEATURE:
<223> OTHER INFORMATION: Synthetic

<400> SEQUENCE: 150

```
ctccctccct ggcccaggtg aaggtgtggt tccagaaccg gaggacaaag tacaaacggc     60
agaagctgga ggaggaaggg cctgagtccg agcagaagaa cgaattcgag ggcagaggca    120
gtctgctgac atgcggtgac gtggaagaga atcccggccc ttctagataa ctgtgccttc    180
tagttgccag ccatctgttg tttgcgcctc actcgtgcct tcattgaccc tggaaggtgc    240
cactcccact gtcctttcct aataaaatga ggaaattgca tcgcattgtc tgagtaggtg    300
tcattctatt ctggcgtatc gagtggctca ggacagcaag agcgaggatt gggaagacaa    360
tagcaggcat gctggggatg cggtgggctc tatggcggta ccgaagggct cccatcacat    420
caaccggtgg cgcattgcca cgaagcaggc caatggggag acatcgatg tcacctccaa     480 tgactagggt gggcaaccac aa                                             502
```

<210> SEQ ID NO 151
<211> LENGTH: 700
<212> TYPE: DNA
<213> ORGANISM: Artificial Sequence
<220> FEATURE:
<223> OTHER INFORMATION: Synthetic

<400> SEQUENCE: 151

```
ctccctccct ggcccaggtg aaggtgtggt tccagaaccg gaggacaaag tacaaacggc     60
agaagctgga ggaggaaggg cctgagtccg agcagaagaa cgaattcgag ggcagaggca    120
```

```
gtctgctgac atgcggtgac gtggaagaga atcccggccc ttctagaatg gttagcaagg    180
gcgaggagct gttcaccggg gtggtgccca tcctggtcga gctggacggc gacgtaaacg    240
gccacaagtt cagcgtgtcc ggcgagggag agggcgatgc cacctacggc aagctgaccc    300
tgaagttcat ctgcaccacc ggcaagctgc cagtgccctg gcctaccctc gtgaccaccc    360
tgacctaact gtgccttcta gttgccagcc atctgttgtt tgcgcctcac tcgtgccttc    420
attgaccctg gaaggtgcca ctcccactgt cctttcctaa taaaatgagg aaattgcatc    480
gcattgtctg agtaggtgtc attctattct ggcgtatcga gtggctcagg acagcaagag    540
cgaggattgg gaagacaata gcaggcatgc tggggatgcg gtgggctcta tggcggtacc    600
gaagggctcc catcacatca accggtggcg cattgccacg aagcaggcca atggggagga    660
catcgatgtc acctccaatg actagggtgg gcaaccacaa                         700
```

<210> SEQ ID NO 152
<211> LENGTH: 1219
<212> TYPE: DNA
<213> ORGANISM: Artificial Sequence
<220> FEATURE:
<223> OTHER INFORMATION: Synthetic

<400> SEQUENCE: 152

```
ctccctccct ggcccaggtg aaggtgtggt tccagaaccg gaggacaaag tacaaacggc     60
agaagctgga ggaggaaggg cctgagtccg agcagaagaa cgaattcgag ggcagaggca    120
gtctgctgac atgcggtgac gtggaagaga atcccggccc ttctagaatg gttagcaagg    180
gcgaggagct gttcaccggg gtggtgccca tcctggtcga gctggacggc gacgtaaacg    240
gccacaagtt cagcgtgtcc ggcgagggag agggcgatgc cacctacggc aagctgaccc    300
tgaagttcat ctgcaccacc ggcaagctgc cagtgccctg gcctaccctc gtgaccaccc    360
tgacctacgg cgtgcagtgc ttcagccgct accccgacca catgaagcag cacgacttct    420
tcaagtccgc catgcccgaa ggctacgtcc aggagcgcac catcttcttc aaggacgacg    480
gcaactacaa gacccgtgcc gaggtgaagt tcgaaggcga caccctggtg aaccgcatcg    540
agctgaaggg catcgacttc aaggaggacg gcaacatcct ggggcacaag cttgagtaca    600
actacaacag ccacaacgtc tatatcatgg ccgacaagca gaagaacggc atcaaggtga    660
acttcaagat ccgccacaac atcgaggacg gtagcgtgca gctcgctgac cactaccagc    720
agaacactcc tatcggagac ggtcctgtgc tgctgccaga caaccactac ctgagcacac    780
agtccgctct gagcaaagac cctaacgaga gcgcgatca  catggtcctg ctggagttcg    840
tgacagccgc tgggatcact ctcggcatgg acgagctgta caagtaactg tgccttctag    900
ttgccagcca tctgttgttt gcgcctcact cgtgccttca ttgaccctgg aaggtgccac    960
tcccactgtc ctttcctaat aaaatgagga aattgcatcg cattgtctga gtaggtgtca   1020
ttctattctg gcgtatcgag tggctcagga cagcaagagc gaggattggg aagacaatag   1080
caggcatgct ggggatgcgg tgggctctat ggcggtaccg aagggctccc atcacatcaa   1140
ccggtggcgc attgccacga agcaggccaa tggggaggac atcgatgtca cctccaatga   1200
ctagggtggg caaccacaa                                                1219
```

<210> SEQ ID NO 153
<211> LENGTH: 32
<212> TYPE: DNA
<213> ORGANISM: Artificial Sequence
<220> FEATURE:
<223> OTHER INFORMATION: Synthetic

```
<400> SEQUENCE: 153
gattgcctca gatcacacta tctccacttg cc                                    32

<210> SEQ ID NO 154
<211> LENGTH: 27
<212> TYPE: DNA
<213> ORGANISM: Artificial Sequence
<220> FEATURE:
<223> OTHER INFORMATION: Synthetic

<400> SEQUENCE: 154
gagggcctgg tcttctcaaa ggtgttg                                          27

<210> SEQ ID NO 155
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 155
gattgcctca gatcacacta tctccacttg cc                                    32

<210> SEQ ID NO 156
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 156
gagggcctgg tcttctcaaa ggtgttg                                          27

<210> SEQ ID NO 157
<211> LENGTH: 23
<212> TYPE: DNA
<213> ORGANISM: Artificial Sequence
<220> FEATURE:
<223> OTHER INFORMATION: Synthetic

<400> SEQUENCE: 157
ctccctccct ggcccaggtg aag                                              23

<210> SEQ ID NO 158
<211> LENGTH: 27
<212> TYPE: DNA
<213> ORGANISM: Artificial Sequence
<220> FEATURE:
<223> OTHER INFORMATION: Synthetic

<400> SEQUENCE: 158
ttgtggttgc ccaccctagt cattgga                                          27

<210> SEQ ID NO 159
<211> LENGTH: 23
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine

<400> SEQUENCE: 159
ctccctccct ggcccaggtg aag                                         23

<210> SEQ ID NO 160
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)

<400> SEQUENCE: 160
ttgtggttgc ccaccctagt cattgga                                     27

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
gagtccgagc agaagaagaa                                             20

<210> SEQ ID NO 162
<211> LENGTH: 47
<212> TYPE: DNA
<213> ORGANISM: Artificial Sequence
<220> FEATURE:
<223> OTHER INFORMATION: Synthetic

<400> SEQUENCE: 162
tttctgttgg tgctgatatt gcctttatgt gattgctgta tgtctcc               47

<210> SEQ ID NO 163
<211> LENGTH: 42
<212> TYPE: DNA
<213> ORGANISM: Artificial Sequence
<220> FEATURE:
<223> OTHER INFORMATION: Synthetic

<400> SEQUENCE: 163
acttgcctgt cgctctatct tcgaatctgc caggtgctga ta                    42

<210> SEQ ID NO 164
<211> LENGTH: 43
<212> TYPE: DNA
<213> ORGANISM: Artificial Sequence
<220> FEATURE:
<223> OTHER INFORMATION: Synthetic

<400> SEQUENCE: 164
tttctgttgg tgctgatatt gcctgtgctt tacccagttc tct                   43

<210> SEQ ID NO 165
<211> LENGTH: 42
<212> TYPE: DNA
```

```
<213> ORGANISM: Artificial Sequence
<220> FEATURE:
<223> OTHER INFORMATION: Synthetic

<400> SEQUENCE: 165
acttgcctgt cgctctatct tcgctgggtc tctgacatct tt                    42

<210> SEQ ID NO 166
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine
<220> FEATURE:
<221> NAME/KEY: misc_feature
<222> LOCATION: (2)..(2)
<223> OTHER INFORMATION: 2'-O-methoxyethyl modified riboadenosine
<220> FEATURE:
<221> NAME/KEY: misc_feature
<222> LOCATION: (3)..(2)
<223> OTHER INFORMATION: 2'-O-methoxyethyl modified 5-methyluridine
      (ribothymidine)

<400> SEQUENCE: 166
gattgcctca gatcacacta tctccacttg cc                               32

<210> SEQ ID NO 167
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine
<220> FEATURE:
<221> NAME/KEY: misc_feature
<222> LOCATION: (2)..(2)
<223> OTHER INFORMATION: 2'-O-methoxyethyl modified riboadenosine
<220> FEATURE:
<221> NAME/KEY: misc_feature
<222> LOCATION: (3)..(3)
<223> OTHER INFORMATION: 2'-O-methoxyethyl modified riboguanosine

<400> SEQUENCE: 167
gagggcctgg tcttctcaaa ggtgttg                                     27

<210> SEQ ID NO 168
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
```

```
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 168
gattgcctca gatcacacta tctccacttg cc                                    32

<210> SEQ ID NO 169
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 169
gagggcctgg tcttctcaaa ggtgttg                                          27

<210> SEQ ID NO 170
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine
<220> FEATURE:
<221> NAME/KEY: misc_feature
<222> LOCATION: (2)..(2)
<223> OTHER INFORMATION: 2'-O-methoxyethyl modified 5-methyluridine
      (ribothymidine)
<220> FEATURE:
<221> NAME/KEY: misc_feature
<222> LOCATION: (3)..(3)
<223> OTHER INFORMATION: 2'-O-methoxyethyl modified ribocytidine

<400> SEQUENCE: 170
ctccctccct ggcccaggtg aag                                              23

<210> SEQ ID NO 171
<211> LENGTH: 27
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)
<220> FEATURE:
<221> NAME/KEY: misc_feature
<222> LOCATION: (2)..(2)
<223> OTHER INFORMATION: 2'-O-methoxyethyl modified 5-methyluridine
      (ribothymidine)
<220> FEATURE:
<221> NAME/KEY: misc_feature
<222> LOCATION: (3)..(3)
<223> OTHER INFORMATION: 2'-O-methoxyethyl modified riboguanosine

<400> SEQUENCE: 171
ttgtggttgc caccctagt cattgga                                       27

<210> SEQ ID NO 172
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 172
ctccctccct ggcccaggtg aag                                          23

<210> SEQ ID NO 173
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
```

```
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 173
ttgtggttgc ccaccctagt cattgg                                      26

<210> SEQ ID NO 174
<211> LENGTH: 30
<212> TYPE: DNA
<213> ORGANISM: Artificial Sequence
<220> FEATURE:
<223> OTHER INFORMATION: Synthetic

<400> SEQUENCE: 174
gtcgtaccga ctggtagatg acagcaaacc                                  30

<210> SEQ ID NO 175
<211> LENGTH: 29
<212> TYPE: DNA
<213> ORGANISM: Artificial Sequence
<220> FEATURE:
<223> OTHER INFORMATION: Synthetic

<400> SEQUENCE: 175
ggtctcgact atacgcccgt tttcggatc                                   29

<210> SEQ ID NO 176
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 176
gtcgtaccga ctggtagatg acagcaaacc                                  30

<210> SEQ ID NO 177
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 177
ggtctcgact atacgcccgt tttcggatc                                   29

<210> SEQ ID NO 178
<211> LENGTH: 30
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(1)
<223> OTHER INFORMATION: 2'-O-methoxyethyl modified riboguanosine
<220> FEATURE:
<221> NAME/KEY: misc_feature
<222> LOCATION: (2)..(2)
<223> OTHER INFORMATION: 2'-O-methoxyethyl modified 5-methyluridine
      (ribothymidine)
<220> FEATURE:
<221> NAME/KEY: misc_feature
<222> LOCATION: (3)..(3)
<223> OTHER INFORMATION: 2'-O-methoxyethyl modified ribocytidine

<400> SEQUENCE: 178
gtcgtaccga ctggtagatg acagcaaacc                                30

<210> SEQ ID NO 179
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified 5-methyluridine
      (ribothymidine)

<400> SEQUENCE: 179
ggtctcgact atacgcccgt tttcggatc                                 29

<210> SEQ ID NO 180
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 180
gtcgtaccga ctggtagatg acagcaaacc                                30
```

```
<210> SEQ ID NO 181
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 181
ggtctcgact atacgcccgt tttcggatc                                       29

<210> SEQ ID NO 182
<211> LENGTH: 1180
<212> TYPE: DNA
<213> ORGANISM: Artificial Sequence
<220> FEATURE:
<223> OTHER INFORMATION: Synthetic

<400> SEQUENCE: 182
aacgaccact ttgtcaagct catttcctgg tatgtggctg gggccagaga ctggctctta      60
aaaagtgcag ggtctggcgc cctctggtgg ctggctcaga aaagggccc tgacaactct     120 tttcatcttc taggtatgac aacgaatttg gctacagcaa caggtggtg gacctcatgg     180 cccacatggc ctccaaggag ggatctggcg ccaccaattt cagcctgctg aaacaggctg    240
gcgacgtgga agagaaccct ggacctgtga gcaagggcga ggagctgttc accggggtgg    300
tgcccatcct ggtcgagctg gacggcgacg taaacggcca agttcagc gtgtccggcg      360 agggcgaggg cgatgccacc tacggcaagc tgaccctgaa gttcatctgc accaccggca    420
agctgcccgt gccctggccc accctcgtga ccaccctgac ctacggcgtg cagtgcttca    480
gccgctaccc cgaccacatg aagcagcacg acttcttcaa gtccgccatg cccgaaggct    540
acgtccagga gcgcaccatc ttcttcaagg acgacggcaa ctacaagacc cgcgccgagg    600
tgaagttcga gggcgacacc ctggtgaacc gcatcgagct gaagggcatc gacttcaagg    660
aggacggcaa catcctgggg cacaagctgg agtacaacta caacagccac aacgtctata    720
tcatggccga caagcagaag aacggcatca aggtgaactt caagatccgc cacaacatcg    780
aggacggcag cgtgcagctc gccgaccact accagcagaa cacccccatc ggcgacggcc    840
ccgtgctgct gcccgacaac cactacctga gcacccagtc cgccctgagc aaagacccca    900
acgagaagcg cgatcacatg gtcctgctgg agttcgtgac cgccgccggg atcactctcg    960
gcatggacga gctgtacaag taagacccct ggaccaccag ccccagcaag agcacaagag   1020
```

| | |
|---|---|
| gaagagagag accctcactg ctggggagtc cctgccacac tcagtccccc accacactga | 1080 |
| atctcccctc ctcacagttg ccatgtagac cccttgaaga ggggaggggc ctagggagcc | 1140 |
| gcaccttgtc atgtaccatc aataaagtac cctgtgctca | 1180 |

<210> SEQ ID NO 183
<211> LENGTH: 1188
<212> TYPE: DNA
<213> ORGANISM: Artificial Sequence
<220> FEATURE:
<223> OTHER INFORMATION: Synthetic

<400> SEQUENCE: 183

| | |
|---|---|
| gtcgtaccga ctggtagatg acagcaaacc tgttcccttt tcggctctgc aacaccgcct | 60 |
| agaccgaccg gatacacggg tagggcttcc gctttacccg tctccctcct ggcgcttgtc | 120 |
| ctcctctccc agtcggcacc acagcggtgg ctgccgggcg tggtgtcggt gggtcggttg | 180 |
| gttttgtct caccgttggt gtccgtgccg ttcagttgcc cgccatggct ggatctggtg | 240 |
| gtactagtgg aagcaagggt gaggagctgt tcaccggagt ggtgcctatc ctggtcgagc | 300 |
| tggacggcga cgtaaacggt cacaagttca gcgtgcgtgg tgagggcgag ggcgatgcca | 360 |
| ccaacggcaa gctgaccctg aagttcatct gcaccactgg caagctgcct gttccatggc | 420 |
| caaccctcgt gactacactg acctacggcg ttcagtgctt cagccgttac cctgaccata | 480 |
| tgaagcgtca cgacttcttc aagtctgcca tgcctgaagg ctacgtccag gagcgtacca | 540 |
| tcagcttcaa ggacgatggc acctacaaga ctcgtgccga ggtgaagttc gagggtgaca | 600 |
| ccctggtgaa ccgcatcgag ctgaagggta tcgacttcaa ggaggacggc aacatcctgg | 660 |
| gtcacaagct ggagtacaac ttcaacagcc acaacgtcta tatcaccgcc gacaagcaga | 720 |
| agaacggcat caaggccaac ttcaagattc gtcacaacgt ggaggacggt agcgtgcagc | 780 |
| tcgcagacca ctaccagcag aacacgccta tcggcgacgg tccagtgttg ctgccagaca | 840 |
| accactacct gagcacccag tccgtgctga gcaaagaccc gaacgagaag cgcgatcaca | 900 |
| tggtcctgct ggagttcgtg accgcagccg gtatcactgg aaccggtgct ggaagtggtg | 960 |
| agctggatcc gttcggcgcc cctgccggcg ccctggcgg tcccgcgctg gggaacggag | 1020 |
| tggccggcgc cggcgaagaa gaccggctg cggccttctt ggcgcagcaa gagagcgaga | 1080 |
| ttgcgggcat cgagaacgac gaggccttcg ccatcctgga cggcggcgcc cccgggcccc | 1140 |
| agccgcacgg cgagccgccg atccgaaaac gggcgtatag tcgagacc | 1188 |

<210> SEQ ID NO 184
<211> LENGTH: 1129
<212> TYPE: DNA
<213> ORGANISM: Artificial Sequence
<220> FEATURE:
<223> OTHER INFORMATION: Synthetic

<400> SEQUENCE: 184

| | |
|---|---|
| tcagggggcgg ggcgccgccc ccggaagtac ttccccttaa aggctggggc ctgccggaaa | 60 |
| tggcgcagcg gcagggaggg gctcttcacc cagtccggca gttgaagctc ggcgctcggg | 120 |
| ttaccccctgc agcgacgccc cctggtccca cagataccac tgctgctccc gcccttcgc | 180 |
| tcctcggccg cgcaatgggc ggatcgggtg ggactagtgg cagcaagggc gaggagctgt | 240 |
| tcaccggggt ggtgcccatc ctggtcgagc tggacggcga cgtaaacggc cacaagttca | 300 |
| gcgtgcgcgc cgagggcgag ggcgatgcca ccaacggcaa gctgaccctg aagttcatct | 360 |
| gcaccaccgg caagctgccc gtgccctggc ccaccctcgt gaccaccctg acctacggcg | 420 |

```
tgcagtgctt cagccgctac cccgaccaca tgaagcgcca cgacttcttc aagtccgcca    480
tgcccgaagg ctacgtccag gagcgcacca tcagcttcaa ggacgacggc acctacaaga    540
cccgcgccga ggtgaagttc gagggcgaca ccctggtgaa ccgcatcgag ctgaagggca    600
tcgacttcaa ggaggacggc aacatcctgg ggcacaagct ggagtacaac ttcaacagcc    660
acaacgtcta tatcaccgcc gacaagcaga agaacggcat caaggccaac ttcaagatcc    720
gccacaacgt ggaggacggc agcgtgcagc tcgccgacca ctaccagcag aacaccccca    780
tcggcgacgg ccccgtgctg ctgcccgaca accactacct gagcacccag tccgtgctga    840
gcaaagaccc caacgagaag cgcgatcaca tggtcctgct ggagttcgtg accgccgccg    900
ggatcactgg aaccggtgct ggaagtggta cacgcgacga cgagtacgac tacctcttta    960
aaggtgaggc catgggctct cgcactctac acagtcctcg ttcggggacc cgggccactc   1020
ccggtggacc ctcgtgccgg ccacccctgc actgatatag gcctccctca gcccttcctt   1080
tttgtgcggt tccgtctcct acccagctca gcctcttctc ccccgctca                1129
```

<210> SEQ ID NO 185
<211> LENGTH: 20
<212> TYPE: DNA
<213> ORGANISM: Artificial Sequence
<220> FEATURE:
<223> OTHER INFORMATION: Synthetic
<400> SEQUENCE: 185

```
cctccaagga gtaagacccc                                                  20
```

<210> SEQ ID NO 186
<211> LENGTH: 20
<212> TYPE: DNA
<213> ORGANISM: Artificial Sequence
<220> FEATURE:
<223> OTHER INFORMATION: Synthetic
<400> SEQUENCE: 186

```
gaacggatcc agctcagcca                                                  20
```

<210> SEQ ID NO 187
<211> LENGTH: 20
<212> TYPE: DNA
<213> ORGANISM: Artificial Sequence
<220> FEATURE:
<223> OTHER INFORMATION: Synthetic
<400> SEQUENCE: 187

```
ggtagtcgta ctcgtcgtcg                                                  20
```

<210> SEQ ID NO 188
<211> LENGTH: 34
<212> TYPE: DNA
<213> ORGANISM: Artificial Sequence
<220> FEATURE:
<223> OTHER INFORMATION: Synthetic
<400> SEQUENCE: 188

```
acgaagtgtt ggatataagc cagactgtaa gtga                                  34
```

<210> SEQ ID NO 189
<211> LENGTH: 46
<212> TYPE: DNA
<213> ORGANISM: Artificial Sequence
<220> FEATURE:

<223> OTHER INFORMATION: Synthetic

<400> SEQUENCE: 189
tctaagcaat tataagccat ttcacataaa actcttttag gttaaa                46

<210> SEQ ID NO 190
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 190
acgaagtgtt ggatataagc cagactgtaa gtga                             34

<210> SEQ ID NO 191
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)

<400> SEQUENCE: 191
tctaagcaat tataagccat ttcacataaa actcttttag gttaaa                46

<210> SEQ ID NO 192
<211> LENGTH: 41
<212> TYPE: DNA
<213> ORGANISM: Artificial Sequence
<220> FEATURE:
<223> OTHER INFORMATION: Synthetic

<400> SEQUENCE: 192
gccctgtagt ctctctgtat gttatatgtc acattttgta a                     41

<210> SEQ ID NO 193
<211> LENGTH: 40
<212> TYPE: DNA
<213> ORGANISM: Artificial Sequence
<220> FEATURE:
<223> OTHER INFORMATION: Synthetic

<400> SEQUENCE: 193
aagtaattca cttacagtct ggcttatatc caacacttcg                       40

<210> SEQ ID NO 194
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 194
gccctgtagt ctctctgtat gttatatgtc acattttgta a                     41

<210> SEQ ID NO 195
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 195
aagtaattca cttacagtct ggcttatatc caacacttcg                                  40

<210> SEQ ID NO 196
<211> LENGTH: 24
<212> TYPE: DNA
<213> ORGANISM: Artificial Sequence
<220> FEATURE:
<223> OTHER INFORMATION: Synthetic

<400> SEQUENCE: 196
agcttgctgg tgaaaaggac ccca                                                   24

<210> SEQ ID NO 197
<211> LENGTH: 46
<212> TYPE: DNA
<213> ORGANISM: Artificial Sequence
<220> FEATURE:
<223> OTHER INFORMATION: Synthetic

<400> SEQUENCE: 197
aatgtgcctc tctacaaata ttctctaagc aattataagc catttc                           46

<210> SEQ ID NO 198
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 198
agcttgctgg tgaaaaggac ccca                                                   24

<210> SEQ ID NO 199
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 199
aatgtgcctc tctacaaata ttctctaagc aattataagc catttc                           46

<210> SEQ ID NO 200
<211> LENGTH: 34
<212> TYPE: DNA
<213> ORGANISM: Artificial Sequence
<220> FEATURE:
<223> OTHER INFORMATION: Synthetic

```
<400> SEQUENCE: 200
acgtcagtct tctcttttgt aatgccctgt agtc                                    34

<210> SEQ ID NO 201
<211> LENGTH: 45
<212> TYPE: DNA
<213> ORGANISM: Artificial Sequence
<220> FEATURE:
<223> OTHER INFORMATION: Synthetic

<400> SEQUENCE: 201
gatggttaaa tgattgacaa aaaaagtaat tcacttacag tctgg                        45

<210> SEQ ID NO 202
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 202
acgtcagtct tctcttttgt aatgccctgt agtc                                    34

<210> SEQ ID NO 203
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboguanosine

<400> SEQUENCE: 203
gatggttaaa tgattgacaa aaaaagtaat tcacttacag tctgg                        45

<210> SEQ ID NO 204
<211> LENGTH: 46
<212> TYPE: DNA
<213> ORGANISM: Artificial Sequence
<220> FEATURE:
<223> OTHER INFORMATION: Synthetic

<400> SEQUENCE: 204
tgtagtctct ctgtatgtta tatgtcacat tttgtaatta acagct                       46

<210> SEQ ID NO 205
<211> LENGTH: 46
<212> TYPE: DNA
<213> ORGANISM: Artificial Sequence
<220> FEATURE:
<223> OTHER INFORMATION: Synthetic

<400> SEQUENCE: 205
atttagataa agaaaacatc acttttaaat ctaatactgg caaatg                       46

<210> SEQ ID NO 206
<211> LENGTH: 46
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)

<400> SEQUENCE: 206
tgtagtctct ctgtatgtta tatgtcacat tttgtaatta acagct                       46

<210> SEQ ID NO 207
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 207
atttagataa agaaaacatc acttttaaat ctaatactgg caaatg                       46

<210> SEQ ID NO 208
<211> LENGTH: 33
<212> TYPE: DNA
<213> ORGANISM: Artificial Sequence
<220> FEATURE:
<223> OTHER INFORMATION: Synthetic

<400> SEQUENCE: 208
catggtacac tcagcacgga tgaaatgaaa cag                                     33

<210> SEQ ID NO 209
<211> LENGTH: 46
<212> TYPE: DNA
<213> ORGANISM: Artificial Sequence
<220> FEATURE:
<223> OTHER INFORMATION: Synthetic

<400> SEQUENCE: 209
agcaattata agccatttca cataaaactc ttttaggtta aagatg                       46

<210> SEQ ID NO 210
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine

<400> SEQUENCE: 210
catggtacac tcagcacgga tgaaatgaaa cag                                     33

<210> SEQ ID NO 211
<211> LENGTH: 46
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
```

<400> SEQUENCE: 211
agcaattata agccatttca cataaaactc ttttaggtta aagatg        46

<210> SEQ ID NO 212
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)

<400> SEQUENCE: 212
tctcagattc cagtttcagc aaatttgctt gatatgtaca gc            42

<210> SEQ ID NO 213
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified 5-methyluridine
      (ribothymidine)

<400> SEQUENCE: 213
tgaatagagt ggttgcacaa acttacggat catttg                   36

<210> SEQ ID NO 214
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 214
atggtgagca agggcgagga gct                                 23

<210> SEQ ID NO 215
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 215
agagtgatcc cggcggcggt ca                                  22

<210> SEQ ID NO 216
<211> LENGTH: 28
<212> TYPE: DNA
<213> ORGANISM: Artificial Sequence
<220> FEATURE:
<223> OTHER INFORMATION: Synthetic

<400> SEQUENCE: 216

```
cccacaattc gctctcacca aacctgag                                              28

<210> SEQ ID NO 217
<211> LENGTH: 61
<212> TYPE: DNA
<213> ORGANISM: Artificial Sequence
<220> FEATURE:
<223> OTHER INFORMATION: Synthetic

<400> SEQUENCE: 217
agtagtaata gtagtagtat taaataattt gataaataat tttagcaata tagttttttg          60
t                                                                          61

<210> SEQ ID NO 218
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine

<400> SEQUENCE: 218
cccacaattc gctctcacca aacctgag                                              28

<210> SEQ ID NO 219
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 219
agtagtaata gtagtagtat taaataattt gataaataat tttagcaata tagttttttg          60
t                                                                          61

<210> SEQ ID NO 220
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine
<220> FEATURE:
<221> NAME/KEY: misc_feature
<222> LOCATION: (2)..(2)
<223> OTHER INFORMATION: 2'-O-methoxyethyl modified ribocytidine
<220> FEATURE:
<221> NAME/KEY: misc_feature
<222> LOCATION: (3)..(3)
<223> OTHER INFORMATION: 2'-O-methoxyethyl modified ribocytidine

<400> SEQUENCE: 220
cccacaattc gctctcacca aacctgag                                              28

<210> SEQ ID NO 221
<211> LENGTH: 61
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified 5-methyluridine
      (ribothymidine)

<400> SEQUENCE: 221
agtagtaata gtagtagtat taaataattt gataaataat tttagcaata tagttttttg    60
t                                                                    61

<210> SEQ ID NO 222
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin moiety
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 222
cccacaattc gctctcacca aacctgag                                       28

<210> SEQ ID NO 223
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin moiety
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
```

```
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 223
agtagtaata gtagtagtat taaataattt gataaataat tttagcaata tagttttttg    60
t                                                                   61

<210> SEQ ID NO 224
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin moiety
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 224
ggtacaagtg gatttgacta attacgagtg gcttgataa                           39

<210> SEQ ID NO 225
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin moiety
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
```

```
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 225
aaacaatgca ctcacttctt cctagagaag agtacattc                    39

<210> SEQ ID NO 226
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine

<400> SEQUENCE: 226
cctattaaat aaaagaataa gcagtattat taagtagccc tgcatttca         49

<210> SEQ ID NO 227
<211> LENGTH: 34
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine

<400> SEQUENCE: 227
catctgcttt tttcccgtgt cattctctgg actg                         34

<210> SEQ ID NO 228
<211> LENGTH: 28
<212> TYPE: DNA
<213> ORGANISM: Artificial Sequence
<220> FEATURE:
<223> OTHER INFORMATION: Synthetic

<400> SEQUENCE: 228
cccacaattc gctctcacca aacctgag                                28

<210> SEQ ID NO 229
<211> LENGTH: 61
<212> TYPE: DNA
<213> ORGANISM: Artificial Sequence
<220> FEATURE:
<223> OTHER INFORMATION: Synthetic

<400> SEQUENCE: 229
agtagtaata gtagtagtat taaataattt gataaataat tttagcaata tagtttttg   60 t                                                                  61

<210> SEQ ID NO 230
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

<223> OTHER INFORMATION: 2'-O-methoxyethyl modified ribocytidine

<400> SEQUENCE: 230
cccacaattc gctctcacca aacctgag                                28

<210> SEQ ID NO 231
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine

<400> SEQUENCE: 231
agtagtaata gtagtagtat taaataattt gataaataat tttagcaata tagtttttg    60 t                                                                   61

<210> SEQ ID NO 232
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified ribocytidine
<220> FEATURE:
<221> NAME/KEY: misc_feature
<222> LOCATION: (2)..(2)
<223> OTHER INFORMATION: 2'-O-methoxyethyl modified ribocytidine
<220> FEATURE:
<221> NAME/KEY: misc_feature
<222> LOCATION: (3)..(3)
<223> OTHER INFORMATION: 2'-O-methoxyethyl modified ribocytidine

<400> SEQUENCE: 232
cccacaattc gctctcacca aacctgag                                28

<210> SEQ ID NO 233
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methoxyethyl modified riboadenosine
<220> FEATURE:
<221> NAME/KEY: misc_feature
<222> LOCATION: (2)..(2)
<223> OTHER INFORMATION: 2'-O-methoxyethyl modified riboguanosine
<220> FEATURE:
<221> NAME/KEY: misc_feature
<222> LOCATION: (3)..(3)
<223> OTHER INFORMATION: 2'-O-methoxyethyl modified 5-methyluridine
      (ribothymidine)

<400> SEQUENCE: 233
agtagtaata gtagtagtat taaataattt gataaataat tttagcaata tagtttttg    60 t                                                                   61

<210> SEQ ID NO 234
<211> LENGTH: 27
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin moiety
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 234
ccacaattcg ctctcaccaa acctgag                                         27

<210> SEQ ID NO 235
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-biotin moiety
<220> FEATURE:
<221> NAME/KEY: misc_feature
<222> LOCATION: (1)..(2)
<223> OTHER INFORMATION: Phosphorothioate 5'-3' linkage
<220> FEATURE:
<221> NAME/KEY: misc_feature
<222> LOCATION: (2)..(3)
<223> OTHER INFORMATION: Phosphorothioate 5'-3' linkage
<220> FEATURE:
<221> NAME/KEY: misc_feature
<222> LOCATION: (3)..(4)
<223> OTHER INFORMATION: Phosphorothioate 5'-3' linkage
<220> FEATURE:
<221> NAME/KEY: misc_feature
<222> LOCATION: (4)..(5)
<223> OTHER INFORMATION: Phosphorothioate 5'-3' linkage
<220> FEATURE:
<221> NAME/KEY: misc_feature
<222> LOCATION: (5)..(6)
<223> OTHER INFORMATION: Phosphorothioate 5'-3' linkage

<400> SEQUENCE: 235
agtagtaata gtagtagtat taaataattt gataaataat tttagcaata tagtttttg    60 t                                                                    61
```

MODIFIED DOUBLE-STRANDED DONOR TEMPLATES

CROSS-REFERENCE TO RELATED APPLICATIONS

This application claims priority to U.S. Provisional Patent Application No. 62/925,366, filed on Oct. 24, 2019, which is incorporated by reference herein in its entirety.

REFERENCE TO SEQUENCE LISTING

This application is filed with a Computer Readable Form of a Sequence Listing in accordance with 37 C.F.R. § 1.821(c). The text file submitted by EFS, "013670-9060-US02_sequence_listing_18-DEC-2020_ST25.K" was created on Dec. 18, 2020, contains 235 sequences, has a file size of 86.4 Kbytes, and is hereby incorporated by reference in its entirety.

TECHNICAL FIELD

Described herein are compositions and methods for improving homology directed repair (HDR) efficiency and reducing homology-independent integration following introduction of double strand breaks with engineered nucleases. Additionally, modifications to double stranded DNA donors to improve the donor potency and efficiency of homology directed repair following introduction of double stranded breaks with programmable nucleases.

BACKGROUND

Genome editing with programmable nucleases allows the site-specific introduction of DNA into target genomes of interest. A number of systems permit targeted genomic editing and these systems include transcription activator-like effector nucleases (TALENs), zinc fingers (ZFNs), or clustered, regularly interspaced, short palindromic repeat (CRISPR).

The CRISPR-Cas9 system has been widely utilized to perform site-specific genome editing in eukaryotic cells. A sequence specific guide RNA is required to recruit Cas9 protein to the target site, and then the Cas9 endonuclease cleaves both strands of the target DNA creating a double stranded break (DSB). This DSB is corrected by the cell's innate DNA damage repair pathways. Two of the main pathways of DSB repair are the error prone non-homologous end joining (NHEJ) pathway, which can lead to random insertions or deletions (indels) in the target DNA, and the homology directed repair (HDR) pathway, which uses a single or double stranded DNA molecule with homology to either side of the DSB as a repair template to generate a desired mutation in the target DNA [1].

Various forms of DNA can be used as the repair template for HDR experiments such as plasmid DNA, double stranded linear DNA (dsDNA), or single stranded DNA (ssDNA). Both dsDNA and ssDNA donors can induce an innate immune response in mammalian tissue culture cells. For short insertions (generally 120 bp) or mutations, a chemically synthesized oligonucleotide such as an IDT® Ultramer™ ssDNA can be used as the single stranded oligo donors (ssODN) for HDR experiments. The use of synthetic ssDNA allows for chemical modifications to be placed in the molecule to potentially improve HDR efficiency. Templates for larger insertions (generally >120 bp) are limited due to the increased complexity of synthesis. Generation of long ssDNA can be a labor intensive and costly process, while linear dsDNA can be generated quickly and in large quantities. Because, the more prevalent NHEJ repair pathway facilitates the ligation of blunt ends, a linear dsDNA donor has a higher risk for homology-independent integration into any DSB present in the cell (including the on-target Cas9 cleavage site, any Cas9 off-target sites, and any endogenous DSB) [2, 3]. When homology-independent integration occurs at the on-target site, the entire donor is incorporated including the homology arms leading to the duplication of one or both homology arm regions.

It has been reported that the addition of a 5'-biotin modification on a linear dsDNA donor can reduce the formation of concatemers and integration via the NHEJ pathway [4]. Similarly, another group reported that biotin or ssDNA overhangs on the 5'-terminus can reduce blunt insertions [5]. Another group suggested that TEG and 2'-OMe ribonucleotide adapters on the 5'-termini of dsDNA donors could potentially increase HDR rates by limiting access of the NHEJ machinery to the free ends of the donor but did not demonstrate any reduction in blunt integration [6].

There is a need for compositions of modified dsDNA templates for HDR and methods thereof that increase the efficiency of HDR and reduce undesired homology-independent integration (both at the targeted site and potential off-target or endogenous DSBs) that is typically associated with linear dsDNA donors.

SUMMARY

One embodiment described herein is a double stranded DNA homology directed repair (HDR) donor comprising: a first homology arm region, an insert region, and a second homology arm region; wherein the first homology arm region and the second homology arm region comprise modifications to one or more nucleotides at or near the 5'-termini. In one aspect, the modifications comprise: modifications to the 2'-position of one or more nucleotides at or near the 5'-terminus of the first homology arm region and modifications to the 2'-position of one or more nucleotides at or near the 5'-terminus of the second homology arm region. In another aspect, the modifications comprise modifications to the 2'-position of the 5'-terminal nucleotide, the 5'-penulimate nucleotide, the 5'-antepenultimate (third) nucleotide, or a combination of the nucleotides at or near the 5'-terminus of the first homology arm region and the second homology arm region. In another aspect, the modifications at or near the 5'-termini of the double stranded DNA HDR donor comprise one or more of: 2'-O-methyl (2'-OMe), 2'-fluoro (2'-F), or 2'-O-methoxyethyl (2'-MOE). In another aspect, the modifications at or near the 5'-termini of the double stranded DNA HDR donor comprise 2'-MOE. In another aspect, the modification at or near the 5'-termini are non-template mismatches relative to a target DNA. In another aspect, the first homology arm region and the second homology arm region are 40 to 150 nucleotides in length. In another aspect, the first homology arm region and the second homology arm region are at least 100 nucleotides in length. In another aspect, the double stranded DNA HDR donor further comprises universal primer sequences. In another aspect, the insert region is greater than 100 bp. In aspect, the insert region is greater than 0.25 kb, greater than 0.5 kb, greater than 1 kb, greater than 2 kb, greater than 3 kb, greater than 4 kb, greater than 5 kb, greater than 6 kb, greater than 7 kb, greater than 8 kb, greater than 9 kb, or greater than 10 kb. In another aspect, the double stranded HDR donor comprises a hairpin at either the 5'-terminus or the 3'-terminus. In another aspect, the double stranded HDR donor comprises a hairpin at both the 5'-terminus and the 3'-terminus. In another aspect, the double stranded DNA HDR donor improves homology directed repair efficiency and reduces homology-independent integration in a programmable nuclease system.

Another embodiment described herein is a programmable nuclease system comprising: a modified double stranded DNA homology directed repair (HDR) donor, a programmable nuclease enzyme, and a gRNA, wherein the gRNA molecule is capable of targeting the programmable nuclease molecule to a target nucleic acid. In one aspect, the modified double stranded DNA HDR donor comprises a first homology arm region, an insert region, and a second homology arm region; wherein the first homology arm region and the second homology arm region comprises modifications to one or more nucleotides at or near the 5'-termini. In another aspect, the modified double stranded DNA HDR donor comprises modifications to the 2'-position of the 5'-terminal nucleotide, the 5'-penulimate nucleotide, the 5'-antepenultimate (third) nucleotide, or a combination of the nucleotides at or near the 5'-terminus of the first homology arm region and the second homology arm region. In another aspect, the modified double stranded DNA HDR donor comprises at least one 2'-OME, 2'-F, or 2'-MOE modifications one or more nucleotides at or near the 5'-termini. In another aspect, the modified double stranded DNA HDR donor comprises one or more 2'-MOE modifications at or near the 5'-termini. In another aspect, the modified double stranded DNA HDR donor comprises universal primer sequences. In another aspect, the modified double stranded DNA HDR donor improves homology directed repair efficiency and reduces homology-independent integration in a programmable nuclease system. In another aspect, the programmable nuclease system comprises one or more of transcription activator-like effector nucleases (TALENs), zinc fingers (ZFNs), or clustered, regularly interspaced, short palindromic repeat (CRISPR). In another aspect, the programmable nuclease system is CRISPR. In another aspect, the programmable nuclease enzyme is CRISPR associated-9 (Cas9). In another aspect, the programmable nuclease system further comprises one or more HDR enhancers.

Another embodiment described herein is a method for increasing homology directed repair (HDR) rates and reducing homology-independent integration in a programmable nuclease system comprising targeting a candidate editing target site locus with an active programmable nuclease system and a modified double stranded DNA HDR donor. In one aspect, the modified double stranded DNA HDR donor comprises a first homology arm region, an insert region, and a second homology arm region; wherein the first homology arm region and the second homology arm region comprises modifications to one or more nucleotides at or near the 5'-termini. In another aspect, the modified double stranded DNA HDR donor comprises modifications to the 2'-position of the 5'-terminal nucleotide, the 5'-penulimate nucleotide, the 5'-antepenultimate (third) nucleotide, or a combination of the nucleotides at or near the 5'-terminus of the first homology arm region and the second homology arm region. In another aspect, the modified double stranded DNA HDR donor comprises at least one 2'-OME, 2'-F, or 2'-MOE modifications one or more nucleotides at or near the 5'-termini. In another aspect, the modified double stranded DNA HDR donor comprises one or more 2'-MOE modifications at or near the 5'-termini. In another aspect, the modified double stranded DNA HDR donor comprises universal primer sequences. In another aspect, the method further comprises one or more HDR enhancers. In another aspect, the modified double stranded DNA HDR donor improves homology directed repair efficiency and reduces homology-independent integration in a programmable nuclease system.

Another embodiment described herein is the use of modified double stranded DNA HDR donors for increasing homology directed repair (HDR) rates and reducing homology-independent integration in a programmable nuclease system, wherein the modified double stranded DNA HDR donor comprises a first homology arm region, an insert region, a second homology arm region; and optionally, one or more universal priming sequences; wherein the first homology arm region and the second homology arm region comprise modifications to one or more nucleotides at or near the 5'-termini. In one aspect, the modification comprises at least one 2'-OME, 2'-F, or 2'-MOE modifications one or more nucleotides at or near the 5'-termini of the double stranded DNA HDR donor.

Another embodiment described herein is a method for manufacturing a modified double stranded DNA HDR donor, the method comprising synthesizing an oligonucleotide comprising a first homology arm region, an insert region, a second homology arm region; and optionally, one or more universal priming sequences; wherein the first homology arm region and the second homology arm region comprise modifications to one or more nucleotides at or near the 5'-termini. In one aspect, the modification comprises at least one 2'-OME, 2'-F, or 2'-MOE modifications one or more nucleotides at or near the 5'-termini of the double stranded DNA HDR donor.

Another embodiment describe herein is a method for manufacturing a modified double stranded DNA HDR donor, the method comprising amplifying a target nucleic sequence comprising a first homology arm region, an insert region, a second homology arm region with one or more universal primers, wherein the universal priming sequences comprise modification to one or more nucleotides at or near the 5'-termini. In one aspect, the modification comprises at least one 2'-OME, 2'-F, or 2'-MOE modifications at one or more nucleotides at or near the 5'-termini of the universal primer.

BRIEF DESCRIPTION OF THE DRAWINGS

FIG. 1A-B show schematics showing homology-independent and homology-dependent integration events when using a dsDNA HDR donor template for Cas9 directed cleavage (FIG. 1A) or endogenous double started breaks or Cas9 off-target cleavage (FIG. 1B). These homology-independent integration events lead to incorporation or duplication of homology arms at double stranded breaks introduced by programmable nucleases.

FIG. 6A shows that for short HDR inserts, hairpin blocked dsDNA donors can be generated by annealing two chemically synthesized ssDNA oligos containing the 5'-MOE hairpin.

FIG. 6B shows that for longer HDR inserts, hairpin blocked dsDNA donors can be generated through PCR amplification. Primers with 5'-MOE hairpins can be used to amplify a target HDR template. The DNA polymerase should not be able to amplify through the MOE containing hairpin. After several cycles, a final dsDNA product containing MOE hairpins on both 5'-termini should be generated.

DETAILED DESCRIPTION

Figure 2:
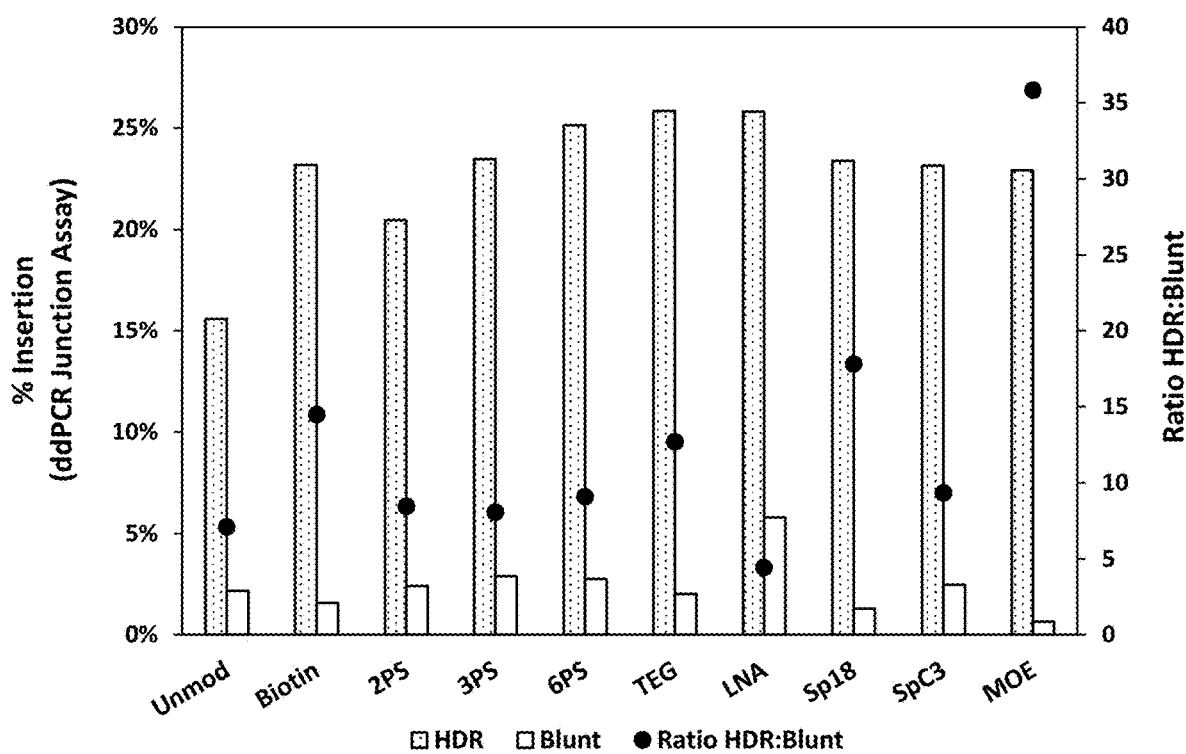
FIG. 2 shows the assessment of dsDNA donor integration via HDR or NHEJ pathways using modified linear dsDNA donors containing a 1 kb insert.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polypeptide," "polynucleotide," and "vector" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or R) are used herein.

As used herein, the terms such as "include," "including," "contain," "containing," "having," and the like mean "comprising." The disclosure also contemplates other embodiments "comprising," "consisting of," and "consisting essentially of," the embodiments, aspects, or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the phrase "an effective amount" of a compound described herein refers to an amount of the compound described herein that will elicit the biological response, for example, reduction or inhibition of an enzyme or a protein activity, or ameliorate symptoms, alleviate conditions, slow or delay disease progression, or prevent a disease, etc.

As used herein, the terms "inhibit," "inhibition," or "inhibiting" refer to the reduction or suppression of a given condition, symptom, or disorder, or disease, or a significant decrease in the baseline activity of a biological activity or process.

As used herein, the term "universal primer" refers to a sequence that does not have a known alignment to a target sequence. Universal primers permit the sequence independent amplification of target sequences.

Disclosed herein are methods and compositions of dsDNA donor templates for improving HDR efficiency and reducing blunt integration events. In various embodiments the disclosed methods and compositions allow for a reduction in homology-independent integration following genomic editing with programmable nucleases. In some embodiments bulky modifications are placed at the 5'-terminus of the linear dsDNA donor. In further embodiments bulky modifications are placed at or near the 5' end of the linear dsDNA donor. Additionally, modifications may be placed at the 2'-position of the DNA (e.g., 2'-MOE, 2'-OME, or 2'-F nucleotides) of a nucleotide at or near the 5'-nucleotide or nucleotides of the dsDNA donor. These modifications demonstrate an improved efficacy at reducing homology-independent integration. Furthermore, this reduction does not seem to be mediated through increased donor stability, as other modifications that have the established ability to block nuclease degradation (PS, etc.) do not also reduce the blunt integration rate to the same extent as other 2'-modifications.

When homology-independent integration occurs at the on-target site, the entire donor is incorporated including the homology arms (FIG. 1) which leads to duplicated homology arms. FIG. 1 is a schematic of homology-independent (duplicated homology arms) and homology-dependent integration events when using a dsDNA HDR donor template. Light grey bars indicate the target genomic DNA sequence while white indicates a non-homologous genomic DNA sequence (either at an endogenous DSB or a Cas9 off-target site). Hashed black indicates DNA sequence that is homologous between the genomic DNA target and the HDR donor (i.e., homology arms). Black indicates the desired insert DNA sequence. FIG. 1A shows insertion of a dsDNA donor through the HDR or NHEJ repair pathways at the on-target Cas9 cleavage site. Insertion through the NHEJ pathway results in duplication of the donor homology arms. FIG. 1B shows insertion of a dsDNA through the NHEJ repair pathway at an endogenous DSB or at an off-target Cas9 cleavage site.

In some embodiments chemical modifications are introduced to the 5'-terminus of linear dsDNA donors. These chemical modifications are used to reduce the risk for NHEJ integration and improve their utility as repair templates in HDR experiments. In some embodiments bulky or large modifications are introduced to the 5'-terminal end of the dsDNA donor. In additional embodiments the modifications may be introduced to the terminal or 5'-DNA nucleotide of the dsDNA oligonucleotide. In some embodiments the modification may be introduced at or near the 5'-terminus of the dsDNA oligonucleotide. In some embodiments the DNA nucleotide or nucleotides at or near the 5'-terminus of the dsDNA oligonucleotide may be modified. In some embodiments, the modifications include biotin, phosphorothioate (PS), triethylene glycol (TEG), Locked Nucleic Acid (LNA, a 2'-oxygen-4'-carbon methylene linkage), hexaethylene glycol (Sp18), 1,3-propanediol (SpC3), 2'-O-methoxyethyl (MOE) ribonucleotides, 2'-O-methyl ribonucleotides (2'-OMe), 2'-fluoro (2'-F) nucleotides, or ribonucleotides. In some embodiments the modification is placed on the 5'-terminal nucleotide, the 5'-penulimate nucleotide, the 5'-antepenultimate (third) nucleotide, or a combination of the nucleotides at or near the 5'-terminus of the dsDNA donor. In additional embodiments the modification is placed at the 2'-position of the 5'-terminal nucleotide, the 5'-penulimate nucleotide, the 5'-antepenultimate (third) nucleotide, or a combination of the nucleotides at or near the 5'-terminus of the dsDNA donor. In yet an additional embodiment the modification is placed at the 2'-position of the 5'-terminal nucleotide, the 5'-penulimate nucleotide, the 5'-antepenultimate (third) nucleotide, or a combination of the nucleotides at or near the 5'-terminus of the dsDNA donor.

The use of 2'-modified ribonucleotides, particularly 2'-O-methoxyethyl (MOE), was found to give the optimal improvement when compared to biotin or other modifications. Additional experiments establishing the use of these modifications with donors mediating large insertions are described herein.

Further improvements to the manufacturing process of the dsDNA donors were evaluated. Universal priming sequences were selected to have no homology to common genomes (human, mouse, rat, zebrafish). Previous work by our group has established the utility of these priming sequences in cloning applications (i.e., highly efficient, reliable amplification). Significant improvements to (1) amplification success with a wide variety of sequences and (2) overall amplification yields can be achieved by incorporating these universal sequences into the donor manufacturing process. Described herein is testing of these universal sequences when placed flanking the complete HDR donor sequence. Due to the lowered risk of homology-independent integration when using the 5'-dsDNA modifications, these sequences do not adversely impact correct HDR rates with modified donors and are only rarely incorporated during blunt integration.

The methods and compositions disclosed herein are of dsDNA donor templates for use in improving HDR efficiency and reducing homology-independent events (blunt integration events or multimerization events). In various embodiments the disclosed methods and compositions allow for a reduction in homology-independent integration or increase in homology-dependent integration following genomic editing with programmable nucleases. In some embodiments bulky nucleotide modifications are placed at the 5'-terminus of the linear dsDNA donor. In additional embodiments modifications placed at the 2'-position of the nucleotide (e.g., 2'-MOE, 2'-OMe) of the 5'-terminal nucleotide or nucleotides near the 5'-terminus of the dsDNA demonstrate an improvement in efficacy at reducing homology-independent integration. Furthermore, this reduction does not seem to be mediated through increased donor stability, as other modifications that have the established ability to inhibit nuclease degradation (PS, etc.) do not also reduce the blunt integration rate to the same extent as other 2'-modifications.

In some embodiments chemical modifications are introduced to the 5'-terminus of linear dsDNA donors. These chemical modifications are used to reduce the risk for NHEJ integration and improve their utility as repair templates in HDR experiments. In some embodiments bulky or large modifications are introduced. In additional embodiments the modifications may be introduced near the 5'-terminus of the dsDNA oligonucleotide donor. In some embodiments the modification may be introduced at or near the 5'-terminus of the dsDNA oligonucleotide donor. In some embodiments the nucleotides at or near the 5'-terminus of the dsDNA oligonucleotide may be modified. In additional embodiments modifications include, but are not limited to: biotin (B); phosphorothioate (PS, *); triethylene glycol (TEG); Locked Nucleic Acid, e.g., a 2'-oxygen-4'-carbon methylene linkage (LNA); hexaethylene glycol (Sp18); 1,3-propanediol (SpC3); 2'-O-methoxyethyl (MOE) ribonucleotides, 2'-O-methyl ribonucleotides (2'-OMe), 2'-fluoro (2'-F) nucleotides, and ribonucleotides.

In further embodiments, the use of hairpin structures on the ends of the dsDNA donor similarly reduces blunt integration.

In one embodiment the end modified dsDNA donor templates would be suitable for use following introduction of double strand breaks by programmable nucleases. In further embodiments the programmable nucleases include transcription activator-like effector nucleases (TALENs), zinc fingers (ZFNs), or clustered, regularly interspaced, short palindromic repeat (CRISPR). In one embodiment, the programmable nuclease system is CRISPR. In one aspect, the programmable nuclease enzyme is CRISPR associated-9 (Cas9).

In one embodiment 5'-terminal modified dsDNA donors are generated by PCR amplification. Primers modified with biotin, phosphorothioate (PS) linkages, TEG, LNA, spacer 18 (SP18), C3 spacers (SpC3), or MOE are used to amplify insert regions and generate end modified dsDNA donors. In some embodiments the insert region is greater than 120 bp. In some embodiments the insert region is at least 1 kb insert regions. In some embodiments the insert region is greater than 1 kb, greater than 2 kb, greater than 3 kb, greater 4 kb, greater than 5 kb, greater than 6 kb, greater than 7 kb, greater than 8 kb, greater than 9 kb, or greater than 10 kb.

In additional embodiments, modifications at or near the 5'-terminus include biotin, phosphorothioate (PS), triethylene glycol (TEG), Locked Nucleic Acid, e.g., a 2'-oxygen-4'-carbon methylene linkage (LNA), hexaethylene glycol (Sp18), 1,3 propanediol (SpC3), 2'-O-methoxyethyl ribonucleotides (MOE), 2'-O-methyl ribonucleotides (2'-OMe), 2'-fluoro (2'-F) nucleotides, and ribonucleotides.

In further embodiments the modification at or near the 5'-terminus includes modifications of the 2'-position of the DNA nucleotide at or near the 5'-terminus of the double stranded DNA donor. In some embodiments the 2'-modification is 2'-MOE, 2'-OMe, or 2'-fluoro and the modification of the nucleotide occurs at or near the 5'-terminus of the double stranded DNA donor. In some embodiments the 5'-terminus modification is on the 5'-terminal nucleotide of the double stranded DNA donor. In additional embodiments the 5'-terminus modification is positioned at the 5'-terminal nucleotide, the 5'-penulimate nucleotide, the 5'-antepenultimate (third) nucleotide, or a combination of the nucleotides at or near the 5'-terminus of the dsDNA donor. In other embodiments the 5'-terminal modification is positioned at 5'-terminus modification is positioned at the 5'-terminal nucleotide, the 5'-penulimate nucleotide, or the 5'-antepenultimate (third) nucleotide. In yet another embodiment the 5'-terminal modification is a 2'-MOE modified ribonucleotide positioned at the terminal 5'-position, the penultimate nucleotide position from the 5'-terminus, the antepenultimate (third) nucleotide position from the 5'-terminus, or a combination thereof. In still a further embodiment the 5'-terminal modification is a 2'-MOE ribonucleotide positioned at the terminal 5'-position, the penultimate nucleotide position from the 5'-terminus, the antepenultimate (third) nucleotide position from the 5'-terminus, or a combination thereof.

In an additional embodiments HDR donors comprise homology arms on either side of an insert. The homology arms are complementary to the sequences flanking the double-stranded break introduced by the programmable nuclease. In some embodiments the homology arms vary in length from at least 20 nucleotides in length to 500 nucleotides in length. In some embodiments the homology arms are at least 40, 50, 60 70, 80, 90, 100, 150, 200, 300, 400, or 500 nucleotides in length. In some embodiments the homology arm length may be greater than 500 nucleotides in length. In additional embodiments the homology arms are preferably at least 40 nucleotides in length and more preferably at least 100 nucleotides in length.

In some embodiments the inserts are placed between homology arms. In some embodiments the inserts are greater than 20 nucleotides in length. In some embodiments the inserts are from at least 1 nucleotide in length to 4 kb in length. In some embodiments the inserts range from 1-2 kb in length. In some embodiments the inserts may be at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb in length. In yet an additional embodiment the insert may be 10 kb or longer in length.

In an additional embodiment HDR donor comprise homology arms on either side of an insert where the insert may include SNPs, MNPs, or deletions. In some embodiments the inserts are from at least 1 nucleotide in length to 4 kb in length. In some embodiments the inserts range from 1-2 kb in length. In some embodiments the inserts may be at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb in length. In yet an additional embodiment the insert may be 10 kb or longer in length.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions, which do not alter the properties and activities of the binding.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% identical to (a) nucleotide sequences, or degenerate, homologous, or codon-optimized variants thereof; or (b) nucleotide sequences capable of hybridizing to the complement of any of the nucleotide sequences in (a).

By a polynucleotide having a nucleotide sequence at least, for example, 90-99% "identical" to a reference nucleotide sequence is intended that the nucleotide sequence of the polynucleotide be identical to the reference sequence except that the polynucleotide sequence can include up to about 10 to 1 point mutations, additions, or deletions per each 100 nucleotides of the reference nucleotide sequence.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

In some embodiments the programmable nucleases (e.g., CRISPR enzyme) or components (e.g. gRNA) can be introduced into the cell using various approaches. Examples include plasmid or viral expression vectors (which lead to endogenous expression of either the enzyme, the gRNA, or both), delivery of the enzyme with separate gRNA/crRNA transfection, or delivery of the enzyme with the gRNA or crRNA as a ribonucleoprotein (RNP) complex.

It will be apparent to one of ordinary skill in the relevant art that suitable modifications and adaptations to the compositions, formulations, methods, processes, apparata, assemblies, and applications described herein can be made without departing from the scope of any embodiments or aspects thereof. The compositions, apparata, assemblies, and methods provided are exemplary and are not intended to limit the scope of any of the disclosed embodiments. All the various embodiments, aspects, and options disclosed herein can be combined in any variations or iterations. The scope of the compositions, formulations, methods, apparata, assemblies, and processes described herein include all actual or potential combinations of embodiments, aspects, options, examples, and preferences described herein. The compositions, formulations, apparata, assemblies, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

REFERENCES

1. Chang et al., "Non-homologous DNA end joining and alternative pathways to double-strand break repair." *Nature Reviews Molecular Cell Biology* 18:495-506 (2017).
2. Roth et al., "Reprogramming human T cell function and specificity with non-viral genome targeting," *Nature* 559 (7714): 405-409 (2018).
3. Li et al., "Design and specificity of long ssDNA donors for CRISPR-based knock-in," *bioRxiv* doi: 10.1101/178905 (2017).
4. Gutierrez-Triann et al., "Efficient single-copy HDR by 5' modified long dsDNA donors," *eLife* 2018; 7:e39468; DOI: 10.7554/eLife.39468 (2018).
5. Canaj et al., "Deep profiling reveals substantial heterogeneity of integration outcomes in CRISPR knock-in experiments," *bioRxiv* doi: 10.1101/841098 (2019).
6. Ghanta et al., "5' Modifications Improve Potency and Efficacy of DNA Donors for Precision Genome Editing," *bioRxiv* doi: 10.1101/354480 (2018).
7. Robinson et al., "Integrative Genomics Viewer," *Nature Biotechnology* 29: 24-26 (2011).

EMBODIMENTS

A1. A double stranded DNA homology directed repair (HDR) donor comprising: a first homology arm region, an insert region, and a second homology arm region; wherein the first homology arm region and the second homology arm region comprise modifications to one or more nucleotides at or near the 5'-termini.

A2. The double stranded DNA HDR donor of A1, wherein the modifications comprise: modifications to the 2'-position of one or more nucleotides at or near the 5'-terminus of the first homology arm region and modifications to the 2'-position of one or more nucleotides at or near the 5'-terminus of the second homology arm region.

A3. The double stranded DNA HDR donor of A1-A2, wherein the modifications comprise modifications to the 2'-position of the 5'-terminal nucleotide, the 5'-penulimate nucleotide, the 5'-antepenultimate (third) nucleotide, or a combination of the nucleotides at or near the 5'-terminus of the first homology arm region and the second homology arm region.

A4. The double stranded DNA HDR donor of A1, wherein the modifications at or near the 5'-termini of the double stranded DNA HDR donor comprise one or more of: 2'-OME, 2'-F, or 2'-MOE.

A5. The double stranded DNA HDR donor of A1-A4, wherein the modifications at or near the 5'-termini of the double stranded DNA HDR donor comprise 2'-MOE.

A6. The double stranded DNA HDR donor of A1-A5, wherein the modification at or near the 5'-termini are non-template mismatches relative to a target DNA.

A7. The double stranded DNA HDR donor of A1-A6, wherein the first homology arm region and the second homology arm region are 40 to 150 nucleotides in length.

A8. The double stranded DNA HDR donor of A1-A7, wherein the first homology arm region and the second homology arm region are at least 100 nucleotides in length.

A9. The double stranded DNA HDR donor of A1-A8, wherein the double stranded DNA HDR donor further comprises universal primer sequences.

A10. The double stranded DNA HDR donor of A1-A9, wherein the insert region is greater than 100 bp.

A11. The double stranded DNA HDR donor of A1-A10, wherein the insert region is greater than 0.25 kb, greater than 0.5 kb, greater than 1 kb, greater than 2 kb, greater than 3 kb, greater 4 kb, greater than 5 kb, greater than 6 kb, greater than 7 kb, greater than 8 kb, greater than 9 kb, or greater than 10 kb.

A12 The double stranded DNA HDR donor of A1-A11, wherein the double stranded HDR donor comprises a hairpin at either the 5'-terminus or the 3'-terminus.

A13. The double stranded DNA HDR donor of A1-A12, wherein the double stranded HDR donor comprises a hairpin at both the 5'-terminus and the 3'-terminus.

A14. The double stranded DNA HDR donor of A1-A13, wherein the double stranded DNA HDR donor improves homology directed repair efficiency and reduces homology-independent integration in a programmable nuclease system.

B1. A programmable nuclease system comprising: a modified double stranded DNA homology directed repair (HDR) donor, a programmable nuclease enzyme, and a gRNA, wherein the gRNA molecule is capable of targeting the programmable nuclease molecule to a target nucleic acid.

B2. The programmable nuclease system of B1, wherein the modified double stranded DNA HDR donor comprises a first homology arm region, an insert region, and a second homology arm region; wherein the first homology arm region and the second homology arm region comprises modifications to one or more nucleotides at or near the 5'-termini.

B3. The programmable nuclease system of B1-B2, wherein the modified double stranded DNA HDR donor comprises modifications to the 2'-position of the 5'-terminal nucleotide, the 5'-penulimate nucleotide, the 5'-antepenultimate (third) nucleotide, or a combination of the nucleotides at or near the 5'-terminus of the first homology arm region and the second homology arm region.

B4. The programmable nuclease system of B1-B3, wherein the modified double stranded DNA HDR donor comprises at least one 2'-OME, 2'-F, or 2'-MOE modifications one or more nucleotides at or near the 5'-termini.

B5. The programmable nuclease system of B1-B4, wherein the modified double stranded DNA HDR donor comprises one or more 2'-MOE modifications at or near the 5'-termini.

B6. The programmable nuclease system of B1-B5, wherein the modified double stranded DNA HDR donor comprises universal primer sequences.

B7. The programmable nuclease system of B1-B6, wherein the modified double stranded DNA HDR donor improves homology directed repair efficiency and reduces homology-independent integration in a programmable nuclease system.

B8. The programmable nuclease system of B1-B7, wherein the programmable nuclease system comprises one or more of transcription activator-like effector nucleases (TALENs), zinc fingers (ZFNs), or clustered, regularly interspaced, short palindromic repeat (CRISPR).

B9. The programmable nuclease system of B1-B8, wherein the programmable nuclease system is CRISPR.

B10. The programmable nuclease system of B1-B9, wherein the programmable nuclease enzyme is CRISPR associated-9 (Cas9).

B11. The programmable nuclease system of B1-B10, wherein the programmable nuclease system further comprises one or more HDR enhancers.

C1. A method for increasing homology directed repair (HDR) rates and reducing homology-independent integration in a programmable nuclease system comprising targeting a candidate editing target site locus with an active programmable nuclease system and a modified double stranded DNA HDR donor.

C1. The method of C1, wherein the modified double stranded DNA HDR donor comprises a first homology arm region, an insert region, and a second homology arm region; wherein the first homology arm region and the second homology arm region comprises modifications to one or more nucleotides at or near the 5'-termini.

C2. The method of C1, wherein the modified double stranded DNA HDR donor comprises modifications to the 2'-position of the 5'-terminal nucleotide, the 5'-penulimate nucleotide, the 5'-antepenultimate (third) nucleotide, or a combination of the nucleotides at or near the 5'-terminus of the first homology arm region and the second homology arm region.

C3. The method of C1-C2, wherein the modified double stranded DNA HDR donor comprises at least one 2'-OME, 2'-F, or 2'-MOE modifications one or more nucleotides at or near the 5'-termini.

C4. The method of C1-C3, wherein the modified double stranded DNA HDR donor comprises one or more 2'-MOE modifications at or near the 5'-termini.

C5. The method of C1-C4, wherein the modified double stranded DNA HDR donor comprises universal primer sequences.

C6. The method of C1-C5, wherein the method further comprises one or more HDR enhancers.

C7. The method of C1-C6, wherein the modified double stranded DNA HDR donor improves homology directed repair efficiency and reduces homology-independent integration in a programmable nuclease system.

D1. A use of modified double stranded DNA HDR donors for increasing homology directed repair (HDR) rates and reducing homology-independent integration in a programmable nuclease system, wherein the modified double stranded DNA HDR donor comprises a first homology arm region, an insert region, a second homology arm region; and optionally, one or more universal priming sequences; wherein the first homology arm region and the second homology arm region comprise modifications to one or more nucleotides at or near the 5'-termini.

D2. The use of D1, wherein the modification comprises at least one 2'-OME, 2'-F, or 2'-MOE modifications one or more nucleotides at or near the 5'-termini of the double stranded DNA HDR donor.

E1. A method for manufacturing a modified double stranded DNA HDR donor, the method comprising synthesizing a first oligonucleotide comprising a first homology arm region, an insert region, a second homology arm region; and optionally, one or more universal priming sequences, synthesizing a second complementary oligonucleotide sequence, and hybridizing the first oligonucleotide and second oligonucleotide sequence; wherein the first homology arm region and the second homology arm region comprise modifications to one or more nucleotides at or near the 5'-termini.

E2. The method of E1, wherein the modification comprises at least one 2'-OME, 2'-F, or 2'-MOE modifications one or more nucleotides at or near the 5'-termini of the double stranded DNA HDR donor.

F1. A method for manufacturing a modified double stranded DNA HDR donor, the method comprising amplifying a target nucleic sequence comprising a first homology arm region, an insert region, a second homology arm region with one or more universal primers, wherein the universal priming sequences comprise modification to one or more nucleotides at or near the 5'-termini.

F2. The method of F1, wherein the modification comprises at least one 2'-OME, 2'-F, or 2'-MOE modifications at one or more nucleotides at or near the 5'-termini of the universal primer.

EXAMPLES

Example 1

HDR Rates are Increased, and NHEJ Insertions are Reduced with Modified dsDNA Donors.

Initial tests were performed to compare the homology-independent (i.e., blunt) integration relative to HDR insertion rates of unmodified linear dsDNA, donors containing 5'-biotin modification, or donors with alternative modifications on or near the 5'-termini. dsDNA donors were generated by PCR amplification of a plasmid containing a 1 kb insert with 100 bp of flanking homology arms targeting the human SERPINC1 gene (100-1000-100; SEQ ID NO: 1; see Table 1 for amplification primer sequences; SEQ ID NO: 2-21). Amplification primers were designed with either unmodified sequence or the indicated modifications. Purified dsDNA donors were delivered at 100 nM (1 µg) in a final volume of 28 µL nucleofection buffer with 2 µM Cas9 V3™ RNP (IDT, Coralville, Iowa) targeting SERPINC1 into 3.5× $10^5$ HEK-293 cells using Lonza nucleofection (Lonza, Basel, Switzerland). The SC1 (SERPINC1) protospacer sequence used can be found in Table 1 (SEQ ID NO: 22). Cells were lysed after 48 hours using QuickExtract™ DNA extraction solution (Lucigen, Madison, WI). HDR and blunt integration rates were assessed by digital-droplet PCR (ddPCR) (Bio-Rad, Hercules, CA) using PCR assays with primers flanking the junction between the target DNA and insert (Table 1; SEQ ID NO: 23-27). Both HDR and blunt junction assays contained one primer external to the homology arm sequence to avoid amplification from non-integrated donor. The HDR assay probe (SEQ ID NO: 25) covered the junction of the target site and insert sequence. The blunt assay probe (SEQ ID NO: 27) covered the junction between the target site and integrated homology arm sequence.

TABLE 1

Sequences of primers, probes, crRNAs, and templates used in Example 1.

| SEQ ID NO. | Name | Sequence |
| --- | --- | --- |
| SEQ ID NO: 1 | SC1 100-1000-100 donor | GATTGCCTCAGATCACACTATCTCCACTTGCCCAGCCCT GTGGAAGATTAGCGGCCATGTATTCCAATGTGATAGGAA CTGTAACCTCTGGAAAAAGGTACGAATTCGAGGGCAGAG GCAGTCTGCTGACATGCGGTGACGTGGAAGAGAATCCCG GCCCTTCTAGAATGGTTAGCAAGGGCGAGGAGCTGTTCA CCGGGGTGGTGCCCATCCTGGTCGAGCTGGACGGCGACG TAAACGGCCACAAGTTCAGCGTGTCCGGCGAGGGCGAGG GCGATGCCACCTACGGCAAGCTGACCCTGAAGTTCATCT GCACCACCGGCAAGCTGCCCGTGCCCTGGCCCACCCTCG TGACCACCCTGACCTACGGCGTGCAGTGCTTCAGCCGCT ACCCCGACCACATGAAGCAGCACGACTTCTTCAAGTCCG CCATGCCCGAAGGCTACGTCCAGGAGCGCACCATCTTCT TCAAGGACGACGGCAACTACAAGACCCGCGCCGAGGTGA AGTTCGAGGGCGACACCCTGGTGAACCGCATCGAGCTGA AGGGCATCGACTTCAAGGAGGACGGCAACATCCTGGGGC ACAAGCTTGAGTACAACTACAACAGCCACAACGTCTATA TCATGGCCGACAAGCAGAAGAACGGCATCAAGGTGAACT TCAAGATCCGCCACAACATCGAGGACGGCAGCGTGCAGC TCGCCGACCACTACCAGCAGAACACCCCCATCGGCGACG GCCCCGTGCTGCTGCCCGACAACCACTACCTGAGCACCC AGTCCGCCCTGAGCAAAGACCCCAACGAGAAGCGCGATC ACATGGTCCTGCTGGAGTTCGTGACCGCCGCCGGGATCA CTCTCGGCATGGACGAGCTGTACAAGTAACTGTGCCTTC |

TABLE 1-continued

Sequences of primers, probes, crRNAs, and templates used in Example 1.

| SEQ ID NO. | Name | Sequence |
|---|---|---|
|  |  | TAGTTGCCAGCCATCTGTTGTTTGCCCCTCCCCCGTGCC TTCCTTGACCCTGGAAGGTGCCACTCCCACTGTCCTTTC CTAATAAAATGAGGAAATTGCATCGCATTGTCTGAGTAG GTGTCATTCTATTCTGGGGGGTGGGGTGGGGCAGGACAG CAAGGGGGAGGATTGGGAAGACAATAGCAGGCATGCTGG GGATGCGGTGGGCTCTATGGCGGTACCAGAGGGGTGAGC TTTCCCCTTGCCTGCCCCTACTGGGTTTTGTGACCTCCA AAGGACTCACAGGAATGACCTCCAACACCTTTGAGAAGA CCAGGCCCTC |
| SEQ ID NO: 2 | SC1 100 Fwd unmod | GATTGCCTCAGATCACACTATCTCC |
| SEQ ID NO: 3 | SC1 100 Rev unmod | GAGGGCCTGGTCTTCTCAAAG |
| SEQ ID NO: 4 | SC1 100 Fwd Biotin | B-GATTGCCTCAGATCACACTATCTCC |
| SEQ ID NO: 5 | SC1 100 Rev Biotin | B-GAGGGCCTGGTCTTCTCAAAG |
| SEQ ID NO: 6 | SC1 100 Fwd 2 x PS | G*A*TTGCCTCAGATCACACTATCTCC |
| SEQ ID NO: 7 | SC1 100 Rev 2 x PS | G*A*GGGCCTGGTCTTCTCAAAG |
| SEQ ID NO: 8 | SC1 100 Fwd 3 x PS | G*A*T*TGCCTCAGATCACACTATCTCC |
| SEQ ID NO: 9 | SC1 100 Rev 3 x PS | G*A*G*GGCCTGGTCTTCTCAAAG |
| SEQ ID NO: 10 | SC1 100 Fwd 6 x PS | G*A*T*T*G*CCTCAGATCACACTATCTCC |
| SEQ ID NO: 11 | SC1 100 Rev 6 x PS | G*A*G*G*G*CTGGTCTTCTCAAAG |
| SEQ ID NO: 12 | SC1 100 Fwd TEG | TEG-GATTGCCTCAGATCACACTATCTCC |
| SEQ ID NO: 13 | SC1 100 Rev TEG | TEG-GAGGGCCTGGTCTTCTCAAAG |
| SEQ ID NO: 14 | SC1 100 Fwd LNA | +GATTGCCTCAGATCACACTATCTCC |
| SEQ ID NO: 15 | SC1 100 Rev LNA | +GAGGGCCTGGTCTTCTCAAAG |
| SEQ ID NO: 16 | SC1 100 Fwd Sp18 | Sp18-GATTGCCTCAGATCACACTATCTCC |
| SEQ ID NO: 17 | SC1 100 Rev Sp18 | Sp18-GAGGGCCTGGTCTTCTCAAAG |
| SEQ ID NO: 18 | SC1 100 Fwd SpC3 | SpC3-GATTGCCTCAGATCACACTATCTCC |
| SEQ ID NO: 19 | SC1 100 Rev SpC3 | SpC3-GAGGGCCTGGTCTTCTCAAAG |
| SEQ ID NO: 20 | SC1 100 Fwd MOE | MGATTGCCTCAGATCACACTATCTCC |
| SEQ ID NO: 21 | SC1 100 Rev MOE SC1-166S guide | MGAGGGCCTGGTCTTCTCAAAG |
| SEQ ID NO: 22 | protospacer | ACCTCTGGAAAAAGGTAAGA |
| SEQ ID NO: 23 | SC1 ddPCR For | AGAACCAGTTTTCAGGCGG |
| SEQ ID NO: 24 | SC1 ddPCR HDR Rev | ACCGCATGTCAGCAGAC |
| SEQ ID NO: 25 | SC1 ddPCR HDR Probe | FAM-TGGAAAAAG-ZEN-GTACGAATTCGAGGGCA-FQ |
| SEQ ID NO: 26 | SC1 ddPCR Blunt Rev | CGCTAATCTTCCACAGGG |
| SEQ ID NO:27 | SC1 ddPCR Blunt Probe | FAM-TCTGGAAAA-ZEN-AGGTAGATTGCCTCAGATCA-FQ |

DNA is uppercase; B- is a 5'-biotin moiety; phosphorothioate (PS) modified linkages are shown with an asterisk (*); triethylene glycol spacer is indicated by an uppercase TEG; 5'-locked ribonucleotides (2'-oxygen-4'-carbon methylene linkage) are shown as a + before the modified ribonucleotide; hexaethylene glycol spacer 18 is shown as Sp18; 1,3-propanediol spacer is shown as SpC3; 2'-O-methoxyethyl modified ribonucleotides are shown with an uppercase M preceeding the modified ribonucleotide; 2'-O-methyl modified ribonucleotides are shown with shown with a lower-case m preceeding the modified ribonucleotide; FAM is 5,6 fluorescein dye; FQ is Iowa Black™ FQ fluorescent quencher; and ZEN is ZEN™ fluorescent quencher. SC1 is SERPINC1. All primers, probes and templates were synthesized by IDT (Coralville, IA).

dsDNA donors containing known nuclease resistant modifications, such as phosphorothioate linkages (2×PS, 3×PS, or 6×PS) or an LNA nucleotide on the 5'-terminus did not improve the HDR:Blunt ratio above unmodified (unmod) donors, as the modifications increased the rates for both HDR and blunt integration (FIG. 2). 5'-modifications (Biotin, TEG, Sp18, and SpC3) on the donor resulted in increased HDR rates with varying degrees of decreased blunt integration. Of these donors, TEG, Biotin, and Sp18 showed increases in the HDR:Blunt ratio (1.8-, 2.0-, and 2.5-fold improvements over unmodified, respectively). See FIG. 2. A donor containing a 2'-O-methoxy-ethyl (2'-MOE) modified ribonucleotide at both of the 5'-termini gave the greatest increase in the HDR:Blunt ratio (5.0-fold improvement over the unmodified donor). See FIG. 2. The HDR rate was similar between the 2'-MOE modification and the other modified donors, suggesting the increased stability alone was not responsible for the increased HDR:Blunt ratio. Furthermore, as stated earlier, the LNA modified donor and the PS-modified donors did not increase the HDR:Blunt rate, indicating that decreased blunt integration is likely not arising from increased nuclease resistance of the template. It also demonstrates that using any 2'-modified ribonucleotide near the 5'-termini of the donor is insufficient to lower blunt integration, and that 2'-MOE modified templates are the most competent for this activity amongst the modifications tested here.

Example 2

5'-Modifications Demonstrate Lower Off-Target Integration when Using Shorter Donor Templates.

Homology-independent integration rates depend on the total donor length, with blunt insertion increasing with decreased donor size. To determine whether 5'-terminal modification would reduce blunt insertion rates with a smaller 42 bp insert (compared with the 1 kb insert tested in Example 1), modified dsDNA donors were generated targeting the SERPINC1 locus described in Example 1 (SC1-166S; SEQ ID NO: 22). Donors consisted of a 42 bp insert containing an EcoRI restriction site with 40 bp homology arms (SC1 40-42-40; SEQ ID NO: 28) and were generated by PCR amplification of a plasmid containing the 42 bp insert with 100 bp of flanking homology arms (see Table 2 for amplification primer sequences; SEQ ID NO: 29-44).

Three modifications (Biotin, Sp18, and MOE) from Example 1 were selected for additional testing, while a 6×PS modification was included as a moderately performing control. Donors with three 2'-MOE ribonucleotides (3×MOE) on the 5'-termini were also included to determine if blunt integration could be further reduced by additional modified residues. A 2'-MOE ribonucleotide was also tested at varying distances from the 5'-termini (Int MOE-3 and -5, with a 2'-MOE positioned 3 or 5 nucleotides from the 5'-terminus; SEQ ID NO: 41-44). Modified and unmodified donors were delivered at 500 nM (1.1 µg) with 2 µM Cas9 V3™ (IDT, Coralville, IA) RNP targeting the SERPINC1 locus into 3.5×10⁵ HEK-293 cells in a 28 µL final volume using Lonza nucleofection (Lonza, Basel Switzerland). DNA was extracted after 48 hours using QuickExtract™ DNA extraction solution (Lucigen, Madison, WI). Integration rates were assessed by RFLP using EcoRI digestion, using a Fragment Analyzer™ machine for band quantification (Advanced Analytical, Ames, IA). HDR and blunt integration events could be distinguished by a 40 bp size difference due to the homology arm duplication.

TABLE 2

Sequences of primers and templates used in Example 2. SEQ ID NO: 22 used for crRNA (Table 1).

| SEQ ID NO. | Name | Sequence |
|---|---|---|
| SEQ ID NO: 28 | SC1 40-42-40 donor | ATTCCAATGTGATAGGAACTGTAACCTCTGGAAAAAGGTAGAATTCTTAGCTCTGTTTACGTCCCAGCGGGCATGAGAGTAAAGAGGGGTGAGCTTTCCCCTTGCCTGCCCCTACTGGGTTT |
| SEQ ID NO: 29 | SC1 40 Fwd unmod | ATTCCAATGTGATAGGAACTGTAACC |
| SEQ ID NO: 30 | SC1 40 Rev unmod | AAACCCAGTAGGGGCAGGC |
| SEQ ID NO: 31 | SC1 40 Fwd 1 × MOE | MATTCCAATGTGATAGGAACTGTAACC |
| SEQ ID NO: 32 | SC1 40 Rev 1 × MOE | MAAACCCAGTAGGGGCAGGC |
| SEQ ID NO: 33 | SC1 40 Fwd 3 × MOE | MAMTMTCCAATGTGATAGGAACTGTAACC |
| SEQ ID NO: 34 | SC1 40 Rev 3 × MOE | MAMAMACCCAGTAGGGGCAGGC |
| SEQ ID NO: 35 | SC1 40 Fwd 6 × PS | A*T*T*C*C*A*ATGTGATAGGAACTGTAACCTCTG |
| SEQ ID NO: 36 | SC1 40 Rev 6 × PS | A*A*A*C*C*C*AGTAGGGGCAGGC |
| SEQ ID NO: 37 | SC1 40 Fwd Biotin | B-ATTCCAATGTGATAGGAACTGTAACC |
| SEQ ID NO: 38 | SC1 40 Rev Biotin | B-AAACCCAGTAGGGGCAGGC |
| SEQ ID NO: 39 | SC1 40 Fwd Sp18 | Sp18-ATTCCAATGTGATAGGAACTGTAACC |
| SEQ ID NO: 40 | SC1 40 Rev Sp18 | Sp18-AAACCCAGTAGGGGCAGGC |
| SEQ ID NO: 41 | SC1 40 Fwd IntMOE(-3) | ATMTCCAATGTGATAGGAACTGTAACCTCTG |
| SEQ ID NO: 42 | SC1 40 Rev IntMOE(-3) | AAMCCCAGTAGGGGCAGGC |
| SEQ ID NO: 43 | SC1 40 Fwd IntMOE(-5) | ATTCMCAATGTGATAGGAACTGTAACCTCTG |
| SEQ ID NO: 44 | SC1 40 Rev IntMOE(-5) | AAACMCCAGTAGGGGCAGGC |
| SEQ ID NO: 45 | SC1 RFLP For | CTTGTCCCTCTTTGCCTTCTCT |

TABLE 2-continued

Sequences of primers and templates used in Example 2. SEQ ID NO: 22 used for crRNA (Table 1).

| SEQ ID NO. | Name | Sequence |
|---|---|---|
| SEQ ID NO: 46 | SC1 RFLP Rev | GGGTGGATCTGAGTGGAAGAAA |

DNA is uppercase; B- is a 5'-biotin moiety; phosphorothioate (PS) modified linkages are shown with an asterisk (*); hexaethylene glycol spacer is shown as Sp18; and 2'-O-methoxyethyl modified ribonucleotides are shown with an uppercase M preceeding the modified ribonucleotide. SC1 is SERPINC1. All primers, guides, and templates were synthesized by IDT (Coralville, IA).

Figure 3:
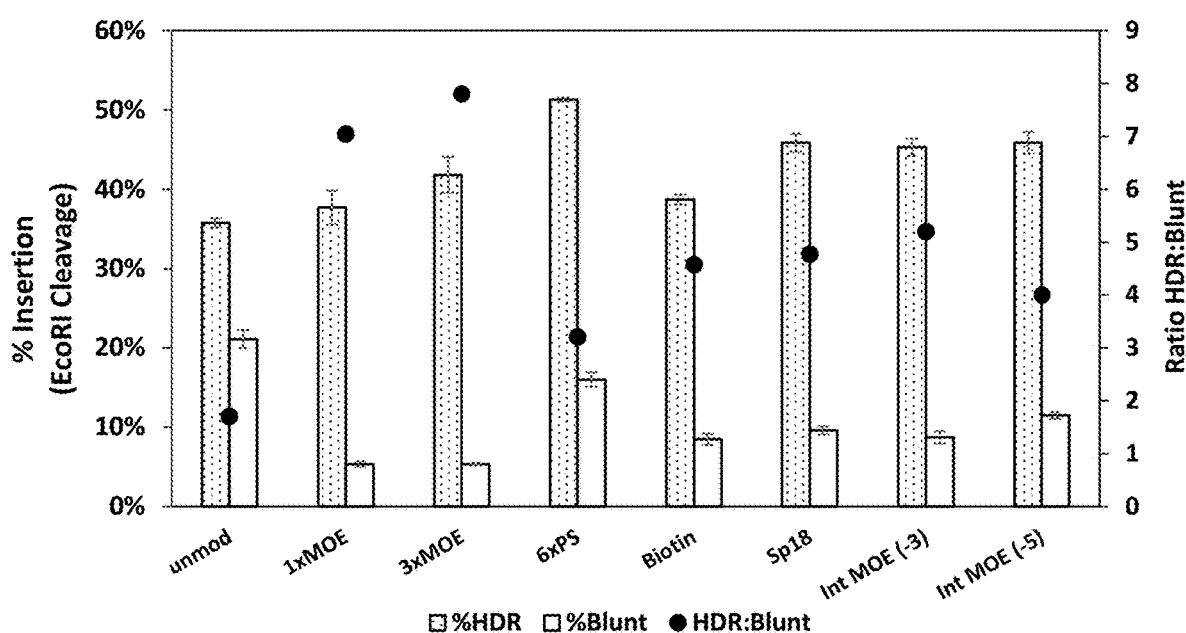
FIG. 3 shows the assessment of dsDNA donor integration via HDR or NHEJ pathways using modified linear dsDNA donors containing a 42 bp insert. Modifications were extended to multiple 2'-MOE ribonucleotides and internally placed 2'-MOE ribonucleotides.

1×MOE and 3×MOE modified donors resulted in the greatest improvement in the HDR:Blunt ratio (4.1- and 4.6-fold improvement over unmod respectively). See FIG. 3. As previously observed, 6×PS, biotin, and Sp18 yielded some improvement (1.9-, 2.7-, and 2.8-fold improvement over unmod respectively) but did not reduce blunt integration to the same extent as the MOE modified donors. See FIG. 3. Interestingly, the position of the 2'-MOE ribonucleotide within the donor did slightly impact its utility for reducing blunt integration. Shifting the MOE ribonucleotide either 3- or 5-nucleotides from the 5'-termini of the donor resulted in only a 3.1- or 2.4-fold improvement in the HDR:Blunt ratio compared to unmodified donor. See FIG. 3. As such, a user skilled in the art would predict that a 2'-MOE ribonucleotide placed within 2-3 nucleotides of the 5'-termini of a donor template would yield a large reduction in NHEJ-mediated insertion.

Example 3

2'-MOE Modifications Lower Integration at Non-Homologous Double Strand Breaks

In addition to blunt integration at the targeted cleavage site, double-strand donors can potentially integrate at any other double-stranded break in the genome, including off-target Cas9 cleavage sites and endogenous breaks in dsDNA. To assess the impact of the 2'-MOE modification on donor integration at potential non-homologous DSBs, dsDNA donors with either unmodified or modified 5'-termini (unmod, 1×MOE, or 6×PS) were generated by PCR amplification (see Table 3 for amplification primer sequences; SEQ ID NO: 48-53) and co-delivered with Cas9 complexed with either the target gRNA (SC1-166S; SEQ ID NO: 22) or a mock "off-target" gRNA with no homology to the donor (AAVS1-670AS; SEQ ID NO: 54; HPRT 38087; SEQ ID NO: 55).

Figure 4:
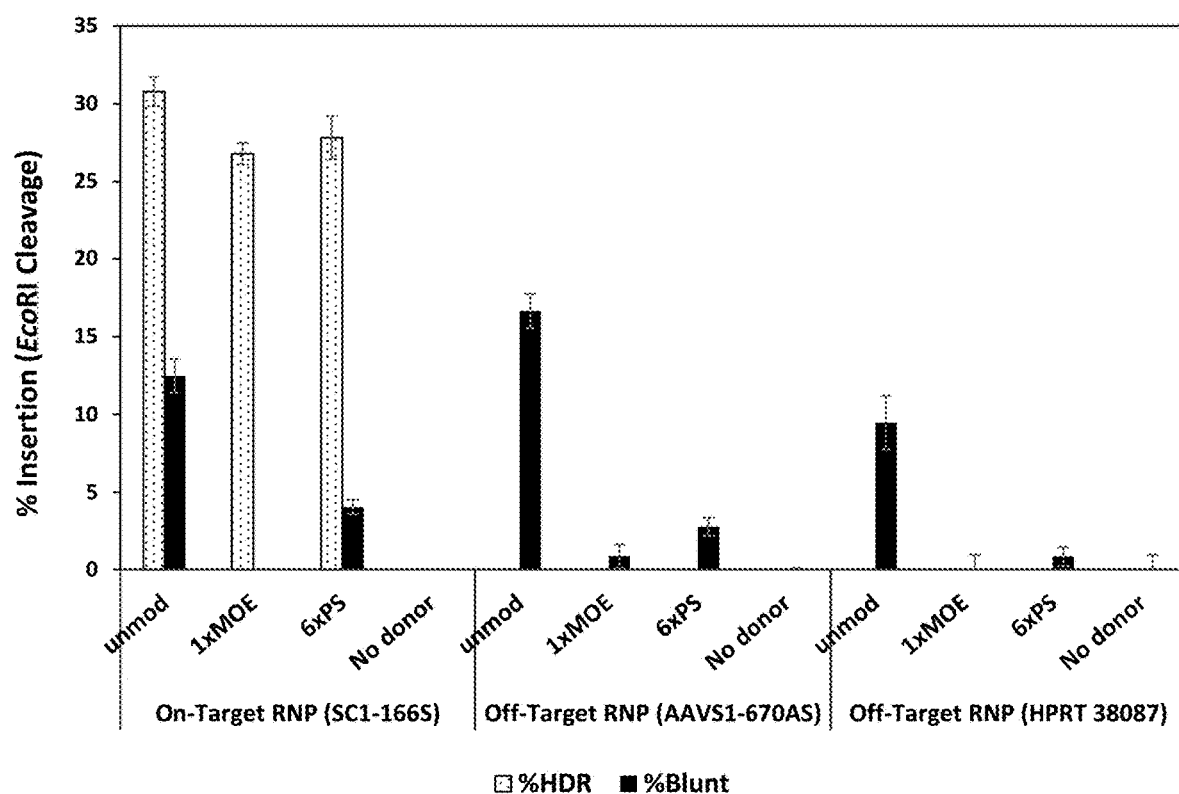
FIG. 4 shows the assessment of dsDNA donor integration via HDR or NHEJ pathways using modified linear dsDNA donors containing a 42 bp insert. Cas9 guides targeting non-homologous sites were used to mimic off-target Cas9 cleavage.

Donors consisted of a 42 bp insert containing an EcoRI restriction site and 50 bp homology arms targeting the SERPINC1 locus (SC1 50-42-50; SEQ ID NO: 47). Donors were delivered at a 100 nM dose (0.3 μg) with 2 μM Cas9 V3™ RNP (IDT, Coralville, IA) and 2 μM Alt-R™ Cas9 Electroporation Enhancer™ into 3×10⁵ K562 cells in a final 28 μL volume by Lonza nucleofection (Lonza, Basel Switzerland). DNA was extracted after 48 hrs using QuickExtract™ DNA extraction solution (Lucigen, Madison, WI). Integration rates were assessed by RFLP using EcoRI digestion, with each band quantified on a Fragment Analyzer™ machine (Advanced Analytical, Ames, IA). HDR and blunt integration events could be distinguished by a 50 bp size difference due to the homology arm duplication (FIG. 4).

TABLE 3

Sequences of primers, crRNA guides, and templates used in Example 3.

| SEQ ID NO. | Name | Sequence |
|---|---|---|
| SEQ ID NO: 47 | SC2 50-42-50 donor | GCGGCCATGTATTCCAATGTGATAGGAACTGTAACCTCTGGAAAAAGGTAGAATTCTTAGCTCTGTTTACGTCCCAGCGGGCATGAGAGTAAAGAGGGGTGAGCTTTCCCCTTGCCTGCCCCTACTGGGTTTTGTGACCTCC |
| SEQ ID NO: 48 | SC1 50 Fwd unmod | GCGGCCATGTATTCCAATGTG |
| SEQ ID NO: 49 | SC1 50 Rev unmod | GGAGGTCACAAAACCCAGTAGG |
| SEQ ID NO: 50 | SC1 50 Fwd 1 × MOE | MGCGGCCATGTATTCCAATGTG |
| SEQ ID NO: 51 | SC1 50 Rev 1 × MOE | MGGAGGTCACAAAACCCAGTAGG |
| SEQ ID NO: 52 | SC1 50 Fwd 6 × PS | G*C*G*G*C*C*ATGTATTCCAATGTG |
| SEQ ID NO: 53 | SC1 50 Rev 6 × PS | G*G*A*G*G*T*CACAAAACCCAGTAGG |
| SEQ ID NO: 54 | AAVS1-670A5 guide protospacer | CCTCTAAGGTTTGCTTACGA |
| SEQ ID NO: 55 | HPRT 38087 guide protospacer | AATTATGGGGATTACTAGGA |
| SEQ ID NO: 56 | AAVS1 RFLP Fwd | GCCAAGGACTCAAACCCAGA |
| SEQ ID NO: 57 | AAVS1 RFLP Rev | CCCCGTTCTCCTGTGGATTC |
| SEQ ID NO: 58 | HPRT RFLP Fwd | AAGAATGTTGTGATAAAAGGTGATGCT |
| SEQ ID NO: 59 | HPRT RFLP Rev | ACACATCCATGGGACTTCTGCCTC |

DNA is uppercase; phosphorothioate (PS) modified linkages are shown with an asterisk (*); hexaethylene glycol spacer is shown as Sp18; and 2'-O-methoxyethyl modified ribonucleotides are shown with an uppercase M preceeding the modified ribonucleotide. SC1 is SERPINC1. All primers, guides, and templates were synthesized by IDT (Coralville, IA).

Blunt integration rates >9% were observed for unmodified dsDNA at the on-target Cas9 site and both "off-target" Cas9 sites. See FIG. 4. Reduced blunt integration (<1%) was observed with the 2'-MOE modified donor, demonstrating that 2'-MOE modifications can also reduce NHEJ-mediated insertions at non-homologous DSBs. See FIG. 4. As previously observed, a 6×PS modification resulted in moderate decrease in blunt integration.

Example 4

Reduction of Off-Target Integration is not the Result of Increased Nuclease Protection, and Specific 2'-Modifications are Required for Efficient Reduction To determine whether the ability of 2'-MOE modification to reduce blunt integration was specific or a general function of modifications at the 2'-position of the 5'-most nucleotides, additional 2'-modifications were tested (RNA, LNA, 2'-OMe, or 2'-F), as well as a non-template 2'-MOE ribonucleotide (SEQ ID NO: 70-71) on the 5'-termini. (Non-template ribonucleotide defined as non-homologous to the target DNA sequence.) Donors consisted of the sequence previously described in Example 2 (SC1 40-42-40; SEQ ID NO: 28), a 42 bp insert containing an EcoRI restriction site and with 40 bp homology arms targeting the SerpinC1 locus. Donors were generated by PCR amplification as previously described (primer sequences unique to Example 4 listed in Table 4; SEQ ID NO: 60-71).

TABLE 4

Sequences of primers, probes, crRNAs, and templates used in Example 4.

| SEQ ID NO. | Name | Sequence |
|---|---|---|
| SEQ ID NO: 60 | SC1 40 Fwd 1 × MOE 2 × PS | MA*T*TCCAATGTGA TAGGAACTGTAACC |
| SEQ ID NO: 61 | SC1 40 Rev 1 × MOE 2 × PS | MA*A*ACCCAGTAG GGGCAGGC |
| SEQ ID NO: 62 | SC1 40 Fwd 5'-RNA | aTTCCAATGTGATA GGAACTGTAACC |
| SEQ ID NO: 63 | SC1 40 Rev 5'-RNA | aAACCCAGTAGGG GCAGGC |
| SEQ ID NO: 64 | SC1 40 Fwd LNA | +ATTCCAATGTGATAG GAACTGTAACC |
| SEQ ID NO: 65 | SC1 40 Rev LNA | +AAACCCAGTAGGG GCAGGC |
| SEQ ID NO: 66 | SC1 40 Fwd 2'-OMe | mATTCCAATGTGATAG GAACTGTAACC |
| SEQ ID NO: 67 | SC1 40 Rev 2'-OMe | mAAACCCAGTAGGGGC AGGC |
| SEQ ID NO: 68 | SC1 40 Fwd 2'-F | fATTCCAATGTGATAG GAACTGTAACC |
| SEQ ID NO: 69 | SC1 40 Rev 2'-F | fAAACCCAGTAGGGGC AGGC |
| SEQ ID NO: 70 | SC1 40 Fwd Non-template 2'-MOE | MGATTCCAATGTGATA GGAACTGTAACC |
| SEQ ID NO: 71 | SC1 40 Rev Non-template 2'-MOE | MGAAACCCAGTAGGGG CAGGC |
| SEQ ID NO: 72 | TNPO3 gRNA protospacer | TGCCCTGGTAAC GGCCAAAG |
| SEQ ID NO: 73 | TNPO3 RFLP Fwd | TCGGACAGAAAGG CATTCACA |
| SEQ ID NO: 74 | TNPO3 RFLP Rev | CAACGGCAAAGGG AGAACTTAAAC |

DNA is uppercase; RNA is lowercase; locked nucleic acids are shown as a + preceeding the modified nucleotide; 2'-O-methoxyethyl modified ribonucleotides are shown with an uppercase M preceeding the modified ribonucleotide; 2'-O-methyl modified ribonucleotides are shown with a lower-case m preceeding the modified ribonucleotide; 2'-fluoro modified ribonucleotides are shown with a lowercase f preceeding the modified ribonucleotide; and non-templated 2'-MOE modified ribonucleotides are shown underlined. SC1 is SERPINC1. All primers and templates were synthesized by IDT (Coralville, IA).

dsDNA donors were co-delivered with Cas9 complexed with either the target gRNA (SC1-166S; SEQ ID NO: 22) or a gRNA with no homology to the donor (TNPO3; SEQ ID NO: 72). Donors were delivered at a 250 nM dose (0.6 μg) with 2 μM Cas9 V3 RNP into HEK-293 cells in a final 28 μL volume by Lonza nucleofection (Lonza, Basel Switzerland). DNA was extracted after 48 hrs using QuickExtract™ DNA extraction solution (Lucigen, Madison, WI). Integration rates were assessed by RFLP using EcoRI, with each band quantified on a Fragment Analyzer™ machine (Advanced Analytical, Ames, IA).

Figure 5:
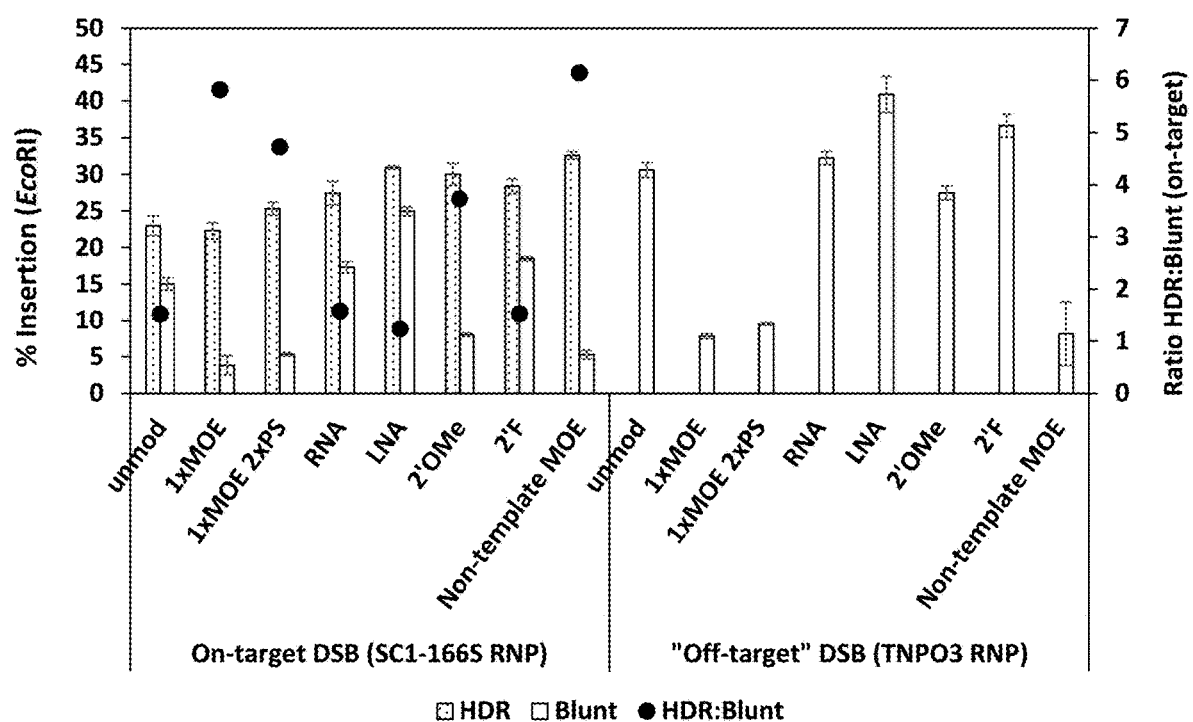
FIG. 5 shows the assessment of dsDNA donor integration via HDR or NHEJ pathways using modified linear dsDNA donors containing a 42 bp insert. Modifications were extended to include additional 2'-modification. Cas9 guides targeting non-homologous sites were used to mimic off-target Cas9 cleavage.

While HDR was either not impacted or slightly boosted by the various modifications, blunt integration was decreased at both the on-target and off-target DSBs whenever a 2'-MOE modification was present (FIG. 5). In contrast, most of the additional 2'-modifications either did not impact or increased the blunt integration rate. The 2'-OMe modification did reduce the blunt integration rate at the on-target DSB, but not to the same extent as the 2'-MOE modifications. See FIG. 5. The 2'-OMe modification did not significantly decrease the blunt integration rate at the off-target DSB.

Taken together, these data suggest that the ability of 2'-MOE modifications to reduce homology-independent integration is (a) not a function of increased stability by promoting nuclease resistance as other stabilizing modifications do not result in a similar outcome and (b) not a generalized function of 2'-modifications on the 5'-most ribonucleotide as other 2'-modifications do not result in a similar outcome.

Example 5

Use of Hairpins as Blocking Groups to Reduce Homology-Independent Integration.

Figures 6A, 6B:
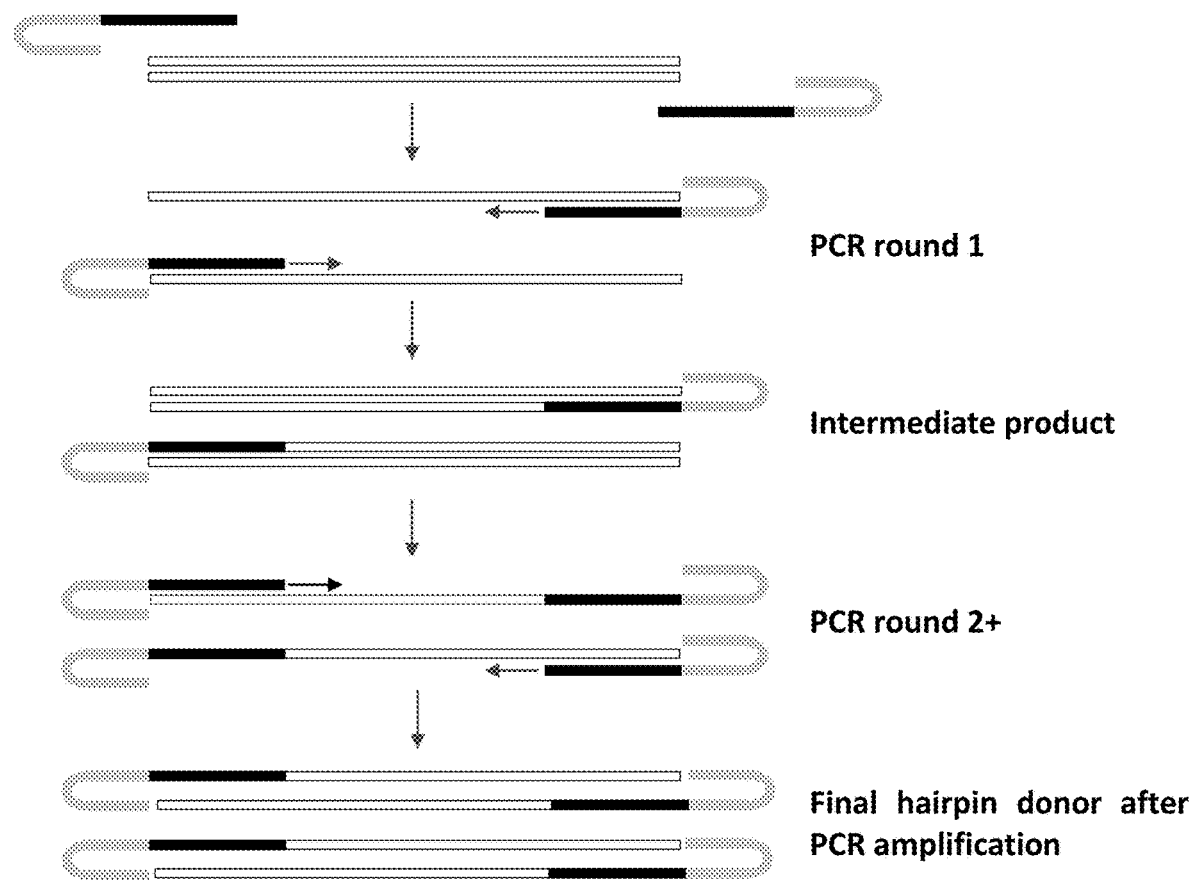
FIG. 6A-B shows synthesis methods for hairpin blocked dsDNA HDR templates. Grey indicates a DNA hairpin composed of 2'-MOE ribonucleotides. Black indicates chemically synthesized unmodified DNA. White indicates a DNA template sequence with available primer binding sites.

In addition to chemical modifications, the use of DNA hairpins at the ends of dsDNA donors can be used to reduce homology-independent integration. Generation of these hairpin-blocked donors is achieved in several methods (FIG. 6A-B). In the case of small HDR events (generally 120 bp insert with 40 bp homology arms), both DNA strands were chemically synthesized with a 5'-MOE hairpin sequence. These MOE adapters contain complementary sequences allowing for the formation of a hairpin structure. The DNA strands were annealed to form a dsDNA HDR donor. In the case of larger HDR events, DNA primers containing a similar 5'-MOE hairpin were chemically synthesized and used for amplification of the desired HDR donor. Use of MOE ribonucleotides within the hairpin structure prevents the procession of the DNA polymerase through the hairpin. For both synthesis methods, hairpin-blocked donors can be used as a nicked HDR template or ligated to generate a fully closed molecule.

Figure 7:
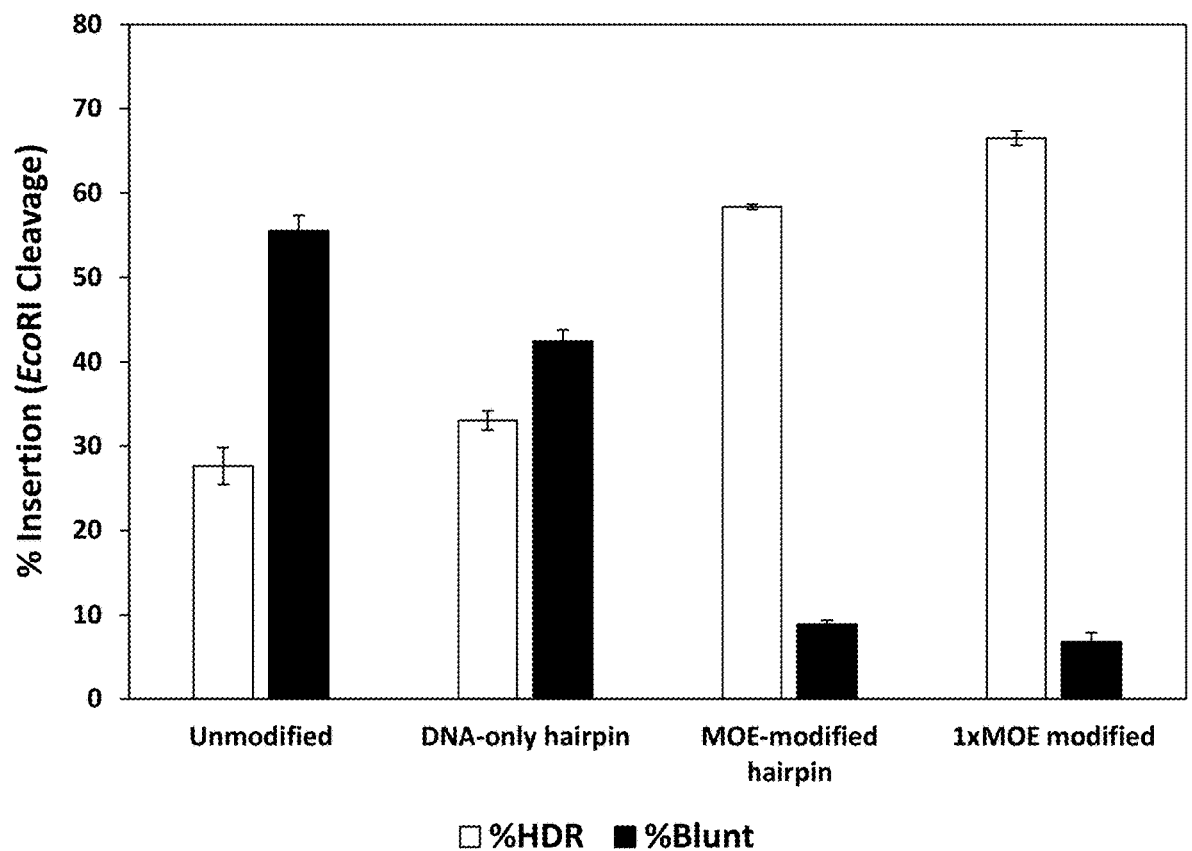
FIG. 7 shows an assessment of dsDNA donor integration via HDR or NHEJ pathways using donors with either a hairpin or a 1xMOE modified base at the 5'-termini. Donors contained 30 bp homology arms and mediated a 6 bp insert to introduce an EcoRI restriction site into the SERPCIN1 locus. Hairpins were composed of a 3 bp stem with a "TTTT" loop and contained either unmodified DNA bases (DNA-only) or 2'-MOE modified bases (MOE-modified). Hairpins were unligated for initial testing.

The use of hairpins on chemically synthesized short oligos was functionally tested in cells. A 66-nt sequence was designed to mediate a 6 base GAATTC insertion in the SERPINC1 locus. This sequence and its reverse complement were synthesized as ssODNs that were either fully unmodified (Table 5; SEQ ID NO: 75-76), contained an unmodified hairpin at the 5'-termini (SEQ ID NO: 77-78), contained a MOE-modified hairpin at the 5' end (SEQ ID NO: 79-80), or contained a non-template MOE-modified base at the 5'-termini (SEQ ID NO: 81-82). Paired ssODNs were diluted to 100 μM and then mixed at a 1:1 ratio to generate a 50 μM final duplex. The oligo mixtures were heated at 95° C. for 1 min and then slow cooled to room temperature to allow the strands to anneal. Duplexed dsDNA donors were co-delivered with Cas9 complexed with the target gRNA (SEQ ID NO: 22). Donors were delivered at a 2 μM concentration e with 2 μM Cas9 V3 RNP and 2 μM Alt-R® Cas9 Electroporation Enhancer into HEK-293 cells in a final 28 μL volume by Lonza nucleofection (Lonza, Basel Switzerland). DNA was extracted after 48 hrs using QuickExtract™ DNA extraction solution (Lucigen, Madison, WI). Integration rates were assessed by RFLP using EcoRI, with each band quantified on a Fragment Analyzer™ machine (Advanced Analytical, Ames, IA) (FIG. 7).

TABLE 5

Sequences of primers and templates used in Example 5.

| SEQ ID NO. | Name | Sequence |
|---|---|---|
| SEQ ID NO: 75 | Top Unmod | GATAGGAACTGTAACCT CTGGAAAAAGGTAGA ATTCAGAGGGGTGAGC TTTCCCCTTGCCTGCC CC |
| SEQ ID NO: 76 | Bottom Unmod | GGGGCAGGCAAGGGGA AAGCTCACCCCTCTGA ATTCTACCTTTTTCCA GAGGTTACAGTTCCTA TC |
| SEQ ID NO: 77 | Top 3DNA HP | pTCGTTTTCGAGATAG GAACTGTAACCTCTGG AAAAAGGTAGAATTCA GAGGGGTGAGCTTTCC CCTTGCCTGCCCC |
| SEQ ID NO: 78 | Bottom 3DNA HP | pTCGTTTTCGAGGGGC AGGCAAGGGGAAAGCT CACCCCTCTGAATTCT ACCTTTTTCCAGAGGT TACAGTTCCTATC |
| SEQ ID NO: 79 | Top 3MOE HP | pMTMCMGMTMTMTMTM CMGMAGATAGGAACTG TAACCTCTGGAAAAAG GTAGAATTCAGAGGGG TGAGCTTTCCCCTTGC CTGCCCC |

TABLE 5-continued

Sequences of primers and templates used in Example 5.

| SEQ ID NO. | Name | Sequence |
|---|---|---|
| SEQ ID NO: 80 | Bottom 3MOE HP | pMTMCMGMTMTMTMTM CMGMAGGGGCAGGCAA GGGGAAAGCTCACCCC TCTGAATTCTACCTTT TTCCAGAGGTTACAGT TCCTATC |
| SEQ ID NO: 81 | Top 1 × MOE | MAGATAGGAACTGTAA CCTCTGGAAAAAGGTA GAATTCAGAGGGGTVG AGCTTTCCCCTTGCCT GCCCC |
| SEQ ID NO: 82 | Bottom 1 × MOE | MAGGGGCAGGCAAGGG GAAAGCTCACCCCTCT GAATTCTACCTTTTTC CAGAGGTTACAGTTCC TATC |

DNA is uppercase; p indicates at 5'-phosphate modification; 2'-O-methoxyethyl modified ribonucleotides are shown with an uppercase M preceeding the modified ribonucleotide; non-templated 2'-MOE modified ribonucleotides are shown underlined. Hairpin structures are indicated with italics. All primers and templates were synthesized by IDT (Coralville, IA).

Use of the shorter 66 bp unmodified dsDNA donor resulted in efficient integration through the NHEJ pathway relative to the HDR pathway (55.5% Blunt vs. 27.6% HDR). Introduction of the DNA-only hairpin to the ends of the donor provided an improvement in the repair profile (42.4% Blunt vs. 33.0% HDR). Inclusion of MOE modifications within the hairpin significantly improved this function to similar levels observed with the single 1×MOE on the 5'-termini (58.4% HDR vs. 8.9% Blunt for MOE-modified hairpin; 66.5% HDR vs. 6.9% Blunt for 1×MOE). Additional optimization to the modified hairpins (i.e., ligation, stem-loop length optimization, etc) could be implemented to further improve this function.

Example 6

2'-MOE Modifications Improve Desired Repair Outcomes at Multiple Sites and in Multiple Cell Lines.

In the following experiments, all guides were tested as Alt-R™ crRNA:tracrRNA complexed to Alt-R™ S. pyogenes Cas9 nuclease. RNP complexes and dsDNA donors were delivered to cells of interest using Lonza nucleofection following recommended protocols.

Figure 8A:
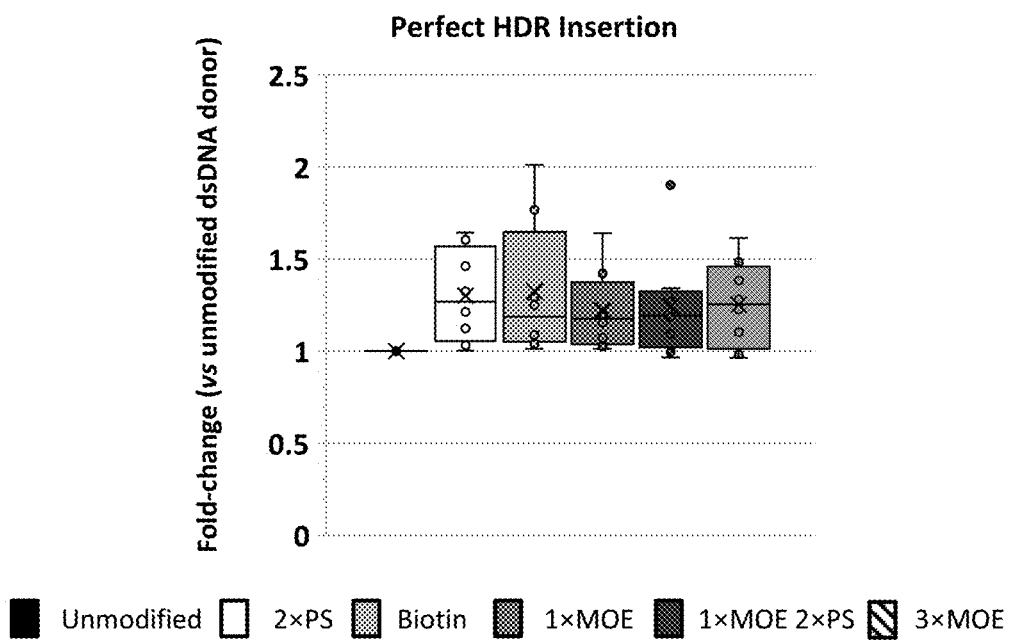
FIG. 8A-C show an assessment of dsDNA donor integration via HDR (FIG. 8A) or NHEJ (FIG. 8B) pathways using modified linear dsDNA donors. The ratio of HDR vs. blunt integration is shown in FIG. 8C. Donors were designed to mediate a 42 bp insertion at 4 genomic loci and were tested in 2 cell lines (n=8 per modification). Results are reported as the fold-change over the unmodified dsDNA donor for each site and cell line.
Figure 8B:
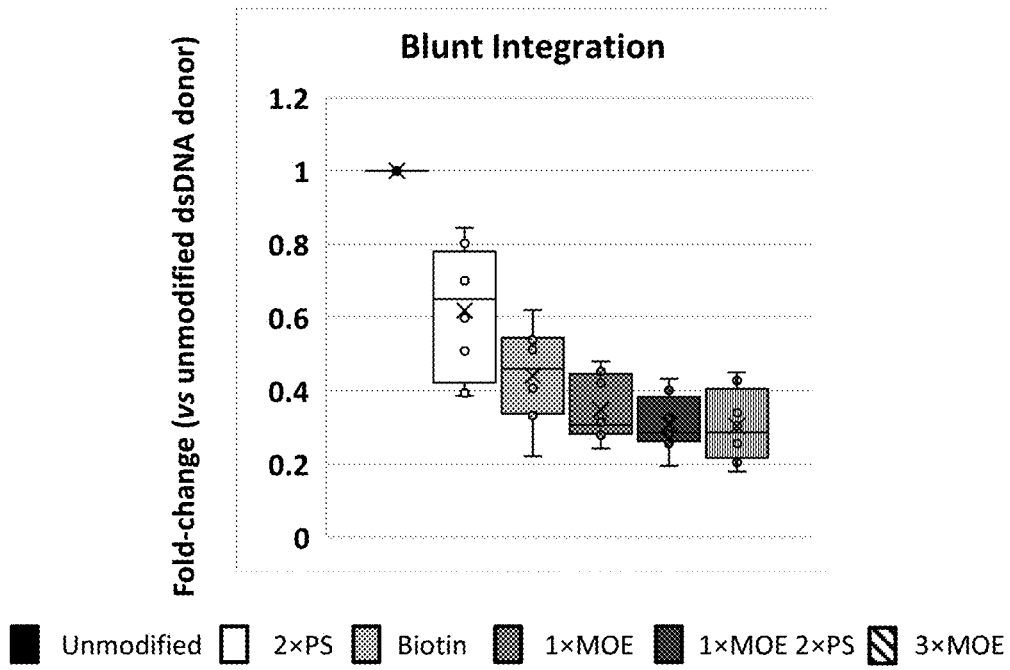
Figure 8C:
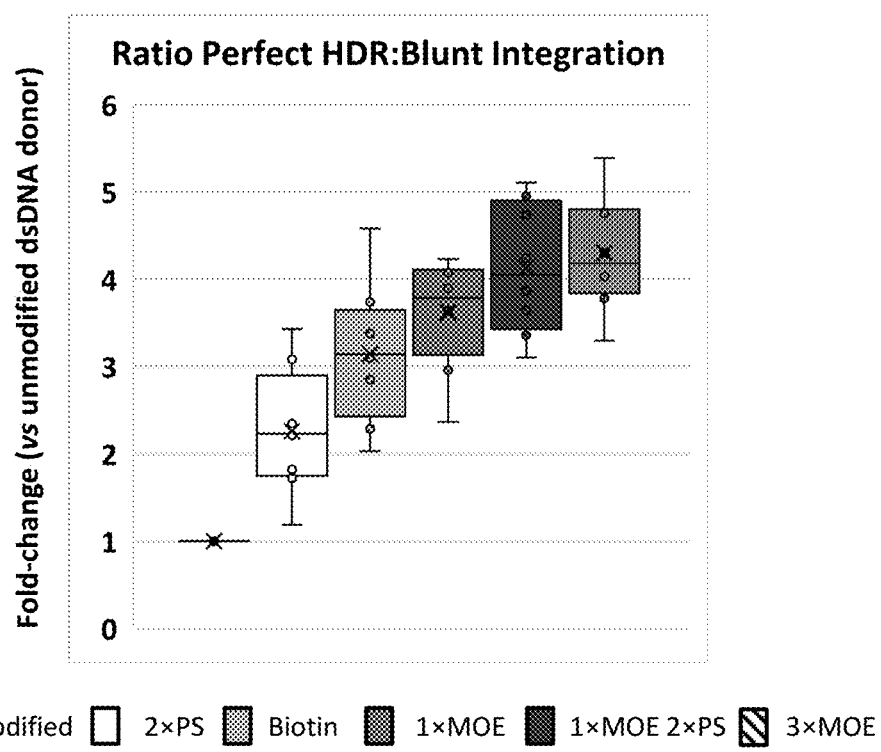

To further validate the ability of the 2'-MOE modification to drive correct repair through higher HDR rates and reduced blunt integration, unmodified and 1×MOE modified dsDNA donors were tested at 4 additional genomic loci (HPRT, AAVS1 670, AAVS1 T2, EMX1) in 2 cell lines (HEK293, K562). Donors were designed to mediate a 42 bp insert and had 40 bp homology arms (SEQ ID NO: 83-86). Donors were generated by PCR amplification as previously described (primer sequences unique to Example 6 listed in Table 6, SEQ ID NO: 95-142). Donors were delivered at 250 nM in a final volume of 28 μL nucleofection buffer with 2 μM Cas9 V3™ RNP (IDT, Coralville, Iowa) and 2 μM Alt-R™ Cas9 Electroporation Enhancer™ into the indicated cell lines using recommended protocols for Lonza nucleofection (Lonza, Basel, Switzerland). The protospacer sequences used can be found in Table 6 (SEQ ID NO:

135-138). Cells were lysed after 48 hours using QuickExtract™ DNA extraction solution (Lucigen, Madison, WI). Repair events were quantified by NGS amplicon sequencing (rhAmpSeq™) on the Illumina MiSeq platform (locus specific sequencing primers listed in Table 6, SEQ ID NO: 139-146) and data analysis was performed using IDT's in-house data analysis pipeline (CRISPAltRations), described in U.S. patent application Ser. No. 16/919,577, which is incorporated herein by reference for such teachings (FIG. 8).

TABLE 6

Sequences of primers, crRNAs, and templates used in Example 6.

| SEQ ID NO. | Name | Sequence |
|---|---|---|
| SEQ ID NO: 83 | HPRT 40-42-40 donor | AGTGCCTTGTCTGTAGTGTCAACTCATTGCTGCCCCT TCCGAATTCTTAGCTCTGTTTACGTCCCAGCGGGCAT GAGAGTAATAGTAATCCCCATAATTTAGCTCTCCATT TCATAGTCTTT |
| SEQ ID NO: 84 | AAVS1 site1 40-42-40 donor | AAGGAGGAGGCCTAAGGATGGGGCTTTTCTGTCACCA ATCGAATTCTTAGCTCTGTTTACGTCCCAGCGGGCAT GAGAGTAACTGTCCCTAGTGGCCCCACTGTGGGGTGG AGGGGACAGAT |
| SEQ ID NO: 85 | AAVS1 site2 40-42-40 donor | TGCCAAGCTCTCCCTCCCAGGATCCTCTCTGGCTCCA TCGGAATTCTTAGCTCTGTTTACGTCCCAGCGGGCAT GAGAGTAATAAGCAAACCTTAGAGGTTCTGGCAAGGA GAGAGATGGCT |
| SEQ ID NO: 86 | EMX1 site 40-42-40 donor | AGGCCAATGGGGAGGACATCGATGTCACCTCCAATGA CTAGAATTCTTAGCTCTGTTTACGTCCCAGCGGGCAT GAGAGTAAGGGTGGGCAACCACAAACCCACGAGGGCA GAGTGCTGCTT |
| SEQ ID NO: 87 | HPRT For Unmod | AGTGCCTTGTCTGTAGTGTCA |
| SEQ ID NO: 88 | HPRT Rev Unmod | AAAGACTATGAAATGGAGAGCTAAATTATG |
| SEQ ID NO: 89 | HPRT For 2 x PS | A*G*TGCCTTGTCTGTAGTGTCA |
| SEQ ID NO: 90 | HPRT Rev 2 x PS | A*A*AGACTATGAAATGGAGAGCTAAATTATG |
| SEQ ID NO: 91 | HPRT For Biotin | B-AGTGCCTTGTCTGTAGTGTCA |
| SEQ ID NO: 92 | HPRT Rev Biotin | B-AAAGACTATGAAATGGAGAGCTAAATTATG |
| SEQ ID NO: 93 | HPRT For 1 x MOE | MAGTGCCTTGTCTGTAGTGTCA |
| SEQ ID NO: 94 | HPRT Rev 1 x MOE | MAAAGACTATGAAATGGAGAGCTAAATTATG |
| SEQ ID NO: 95 | HPRT For 1 x MOE 2 x PS | MA*G*TGCCTTGTCTGTAGTGTCA |
| SEQ ID NO: 96 | HPRT Rev 1 x MOE 2 x PS | MA*A*AGACTATGAAATGGAGAGCTAAATTATG |
| SEQ ID NO: 97 | HPRT For 3 x MOE | MAMGMTGCCTTGTCTGTAGTGTCA |
| SEQ ID NO: 98 | HPRT Rev 3 x MOE | MAMAMAGACTATGAAATGGAGAGCTAAATTATG |
| SEQ ID NO: 99 | AAVS1 T2 For Unmod | AAGGAGGAGGCCTAAGGATGG |
| SEQ ID NO: 100 | AAVS1 T2 Rev Unmod | ATCTGTCCCCTCCACCCC |
| SEQ ID NO: 101 | AAVS1 T2 For 2 x PS | A*A*GGAGGAGGCCTAAGGATGG |
| SEQ ID NO: 102 | AAVS1 T2 Rev 2 x PS | A*T*CTGTCCCCTCCACCCC |
| SEQ ID NO: 103 | AAVS1 T2 For Biotin | B-AAGGAGGAGGCCTAAGGATGG |
| SEQ ID NO: 104 | AAVS1 T2 Rev Biotin | B-ATCTGTCCCCTCCACCCC |
| SEQ ID NO: 105 | AAVS1 T2 For 1 x MOE | MAAGGAGGAGGCCTAAGGATGG |
| SEQ ID NO: 106 | AAVS1 T2 Rev 1 x MOE | MATCTGTCCCCTCCACCCC |
| SEQ ID NO: 107 | AAVS1 T2 For 1 x MOE 2 x PS | MA*A*GGAGGAGGCCTAAGGATGG |
| SEQ ID NO: 108 | AAVS1 T2 Rev 1 x MOE 2 x PS | MA*T*CTGTCCCCTCCACCCC |
| SEQ ID NO: 109 | AAVS1 T2 For 3 x MOE | MAMAMGGAGGAGGCCTAAGGATGG |

TABLE 6-continued

Sequences of primers, crRNAs, and templates used in Example 6.

| SEQ ID NO. | Name | Sequence |
|---|---|---|
| SEQ ID NO: 110 | AAVS1 T2 Rev 3 x MOE | MAMTMCTGTCCCCTCCACCCC |
| SEQ ID NO: 111 | AAVS1 670 For Unmod | TGCCAAGCTCTCCCTCCC |
| SEQ ID NO: 112 | AAVS1 670 Rev Unmod | AGCCATCTCTCTCCTTGCCAG |
| SEQ ID NO: 113 | AAVS1 670 For 2 x PS | T*G*CCAAGCTCTCCCTCCC |
| SEQ ID NO: 114 | AAVS1 670 Rev 2 x PS | A*G*CCATCTCTCTCCTTGCCAG |
| SEQ ID NO: 115 | AAVS1 670 For Biotin | B-TGCCAAGCTCTCCCTCCC |
| SEQ ID NO: 116 | AAVS1 670 Rev Biotin | B-AGCCATCTCTCTCCTTGCCAG |
| SEQ ID NO: 117 | AAVS1 670 For 1 x MOE | MTGCCAAGCTCTCCCTCCC |
| SEQ ID NO: 118 | AAVS1 670 Rev 1 x MOE | MAGCCATCTCTCTCCTTGCCAG |
| SEQ ID NO: 119 | AAVS1 670 For 1 x MOE 2 x PS | MT*G*CCAAGCTCTCCCTCCC |
| SEQ ID NO: 120 | AAVS1 670 Rev 1 x MOE 2 x PS | MA*G*CCATCTCTCTCCTTGCCAG |
| SEQ ID NO: 121 | AAVS1 670 For 3 x MOE | MTMGMCCAAGCTCTCCCTCCC |
| SEQ ID NO: 122 | AAVS1 670 Rev 3 x MOE | MAMGMCCATCTCTCTCCTTGCCAG |
| SEQ ID NO: 123 | EMX1 For Unmod | AGGCCAATGGGGAGGACATC |
| SEQ ID NO: 124 | EMX1 Rev Unmod | AAGCAGCACTCTGCCCTCG |
| SEQ ID NO: 125 | EMX1 For 2 x PS | A*G*GCCAATGGGGAGGACATC |
| SEQ ID NO: 126 | EMX1 Rev 2 x PS | A*A*GCAGCACTCTGCCCTCG |
| SEQ ID NO: 127 | EMX1 For Biotin | B-AGGCCAATGGGGAGGACATC |
| SEQ ID NO: 128 | EMX1 Rev Biotin | B-AAGCAGCACTCTGCCCTCG |
| SEQ ID NO: 129 | EMX1 For 1 x MOE | MAGGCCAATGGGGAGGACATC |
| SEQ ID NO: 130 | EMX1 Rev 1 x MOE | MAAGCAGCACTCTGCCCTCG |
| SEQ ID NO: 131 | EMX1 For 1 x MOE 2 x PS | MA*G*GCCAATGGGGAGGACATC |
| SEQ ID NO: 132 | EMX1 Rev 1 x MOE 2 x PS | MA*A*GCAGCACTCTGCCCTCG |
| SEQ ID NO: 133 | EMX1 For 3 x MOE | MAMGMGCCAATGGGGAGGACATC |
| SEQ ID NO: 134 | EMX1 Rev 3 x MOE | MAMAMGCAGCACTCTGCCCTCG |
| SEQ ID NO: 135 | HPRT gRNA protospacer | AATTATGGGGATTACTAGGA |
| SEQ ID NO: 136 | AAVS1 T2 gRNA protospacer | GGGGCCACTAGGGACAGGAT |
| SEQ ID NO: 137 | AAVS1 670 gRNA protospacer | CCTCTAAGGTTTGCTTACGA |
| SEQ ID NO: 138 | EMX1 gRNA protospacer | GTCACCTCCAATGACTAGGG |
| SEQ ID NO: 139 | HPRT NGS For | ACACTCTTTCCCTACACGACGCTCTTCCGATCTCAGAACTGTCCTTCAGGTTC |
| SEQ ID NO: 140 | HPRT NGS Rev | GTGACTGGAGTTCAGACGTGTGCTCTTCCGTATCTCACGTTTCATTTCATCCGTG |
| SEQ ID NO: 141 | AAVS1 T2 NGS For | ACACTCTTTCCCTACACGACGCTCTTCCGATCTGAGAGATGGCTCCAGGAAATG |
| SEQ ID NO: 142 | AAVS1 T2 NGS Rev | GTGACTGGAGTTCAGACGTGTGCTCTTCCGATCTCACTTCAGGACAGCATGTTTG |
| SEQ ID NO: 143 | AAVS1 670 NGS For | ACACTCTTTCCCTACACGACGCTCTTCCGATCTGATCAGTGAAACGCACCAGA |
| SEQ ID NO: 144 | AAVS1 670 NGS Rev | GTGACTGGAGTTCAGACGTGTGCTCTTCCGATCTCCTCCTTCCTAGTCTCCTGATATT |

TABLE 6-continued

Sequences of primers, crRNAs, and templates used in Example 6.

| SEQ ID NO. | Name | Sequence |
| --- | --- | --- |
| SEQ ID NO: 145 | EMX1 NGS For | ACACTCTTTCCCTACACGACGCTCTTCCGA<br>TCTAGAAGAAGAAGGGCTCCCA |
| SEQ ID NO: 146 | EMX1 NGS Rev | GTGACTGGAGTTCAGACGTGTGCTCTTCCG<br>ATCTCAGGGAGTGGCCAGAGT |

DNA is uppercase; RNA is lowercase; B- is a 5'-biotin moiety; phosphorothioate (PS) modified linkages are shown with an asterisk (*); and 2'-O-methoxyethyl modified ribonucleotides are shown with an uppercase M preceeding the modified ribonucleotide. All primers and templates were synthesized by IDT (Coralville, IA).

As previously observed, the 5'-modifications all improved HDR rates over unmodified dsDNA donors (A). While the fold-improvement in HDR over an unmodified dsDNA varied across sites and cell lines, the average improvement in HDR rates were relatively similar for all modifications tested (ranging from a 1.2 to 1.3-fold improvement). In contrast, MOE modified donors displayed a greater reduction in blunt integration compared to the 2×PS and Biotin donors (B). On average, the fold reductions in blunt integration relative to unmodified dsDNA were 1.6 (2×PS), 2.3 (Biotin), 2.9 (1×MOE), 3.2 (1×MOE, 2×PS), and 3.3 (3×MOE). When the improvements in HDR and blunt integration were assessed together for each site (C, reported as the ratio of HDR:Blunt repair events), MOE modified dsDNA donors outperformed other modifications. The average fold change over unmodified dsDNA were 2.3 (2×PS), 3.1 (Biotin), 3.6 (1×MOE), 4.1 (1×MOE 2×PS), and 4.3 (3×MOE). Taken together, these results demonstrate that MOE modifications are the most efficient at driving the correct repair event following CRISPR editing.

Example 7

HDR Rates are Increased, and NHEJ Insertions are Reduced with Modified dsDNA Donors Mediating Large Insertions.

As a follow-up to the work with short insertions, experiments were performed to compare the HDR and blunt integration rates when using dsDNA donors mediating 300 bp, 500 bp, or 1000 bp insertions at two genomic loci (SERPINC1 and EMX1; see Table 7 for donor sequences and amplification primers, SEQ ID NO: 147-154). Donors were generated by PCR amplification of plasmids containing the desired inserts with 100 bp of flanking homology arms. Amplification primers were designed with either unmodified sequence or the indicated modifications. Long ssDNA (Megamers™) were ordered for comparison at the SERPINC1 locus. Donors were delivered at 100 nM in a final volume of 28 µL nucleofection buffer with 2 µM Cas9 V3™ RNP (IDT, Coralville, Iowa) targeting SERPINC1 or EMX1 into $3.5 \times 10^5$ HEK-293 cells using Lonza nucleofection (Lonza, Basel, Switzerland). Cells were treated with the IDT Alt-R™ HDR Enhancer V2 (1 µM) for 24 hrs post-transfection. The protospacer sequences used is shown in Table 1 (SEQ ID NO: 22) and Table 7 (SEQ ID NO: 161).

Figure 9A:
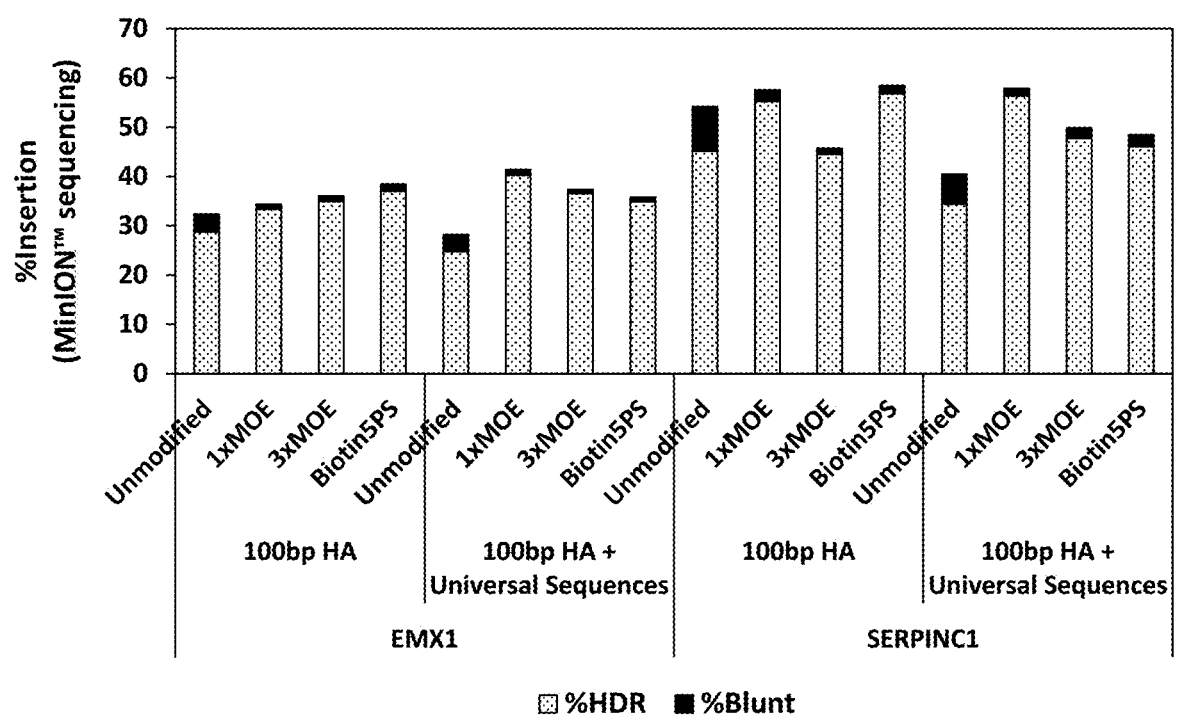
FIG. 9A shows an assessment of dsDNA donor integration via HDR or NHEJ pathways using modified linear dsDNA donors mediating a 300 bp, 500 bp, or 1 kb insert at two genomic loci. A long ssDNA donor targeting the SERPINC1 locus was provided for comparison.
Figure 9B:
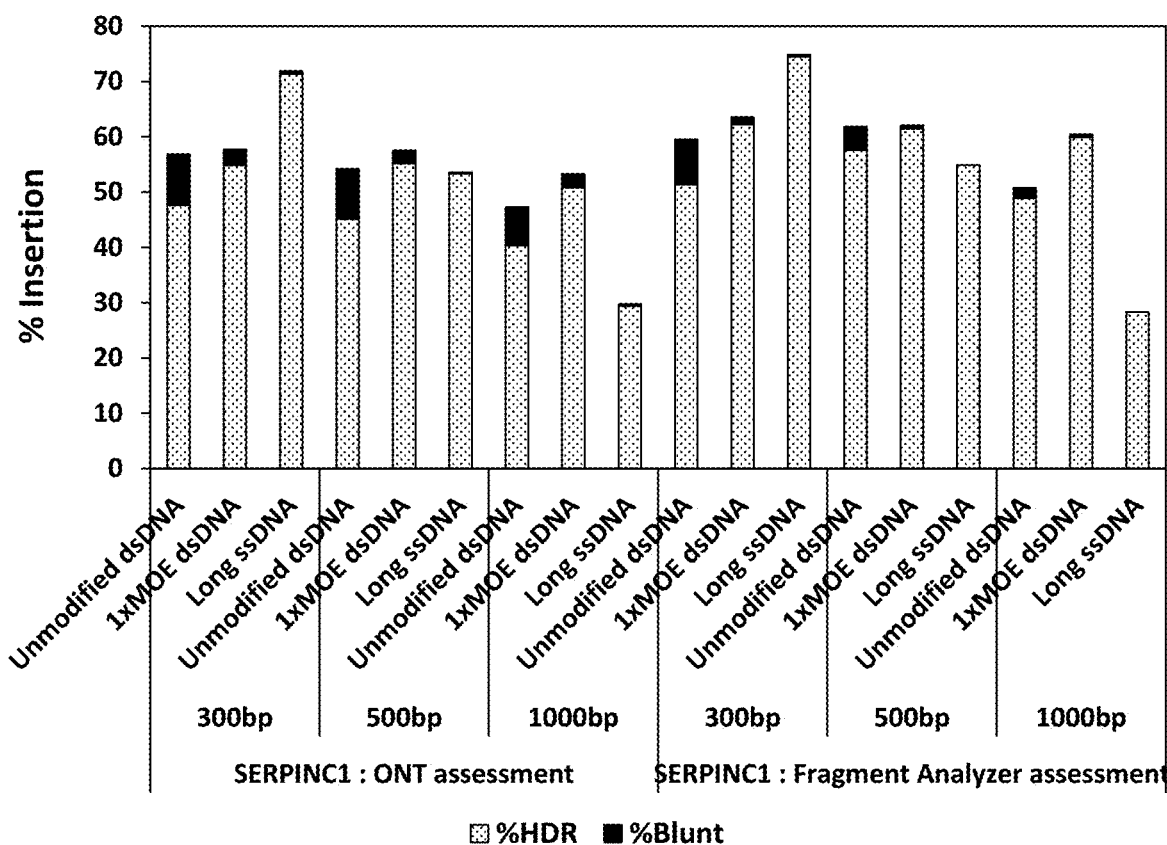
FIG. 9B shows comparison orthogonal analysis methods for assessment of insertion at the SERPINC1 locus. Long-read sequencing using the MinION™ system from Oxford Nanopore Technologies (ONT) was compared to amplicon length analysis where PCR amplicons from genomic DNA samples were run and quantified on a Fragment Analyzer.

Cells were lysed after 48 hours using QuickExtract™ DNA extraction solution (Lucigen, Madison, WI). HDR and blunt integration rates were assessed by long-read sequencing using the MinION™ platform (Oxford Nanopore Technologies, Oxford, UK). Locus specific amplification primers used are listed (Table 7, SEQ ID NO: 162-165). Final sequencing libraries were prepared with the PCR Barcoding Expansion and Ligation Sequencing Kit following the manufacturer's recommended protocols. Final data analysis was performed using IDT's in-house data analysis pipeline (CRISPAltRations) (FIG. 9A). Insertion rates were independently assessed by amplicon length analysis for the SERPINC1 samples. Isolated gDNA was PCR amplified using the SERPINC1 RFLP primers (SEQ ID NO: 45-46). Amplicons were run on a Fragment Analyzer™ machine for band quantification. Insertion events were identified based on expected amplicon sizes for integration events (FIG. 9B).

TABLE 7

Sequences of Primers and Templates used in Example 7. SEQ ID NO: 22 used for SERPINC1 crRNA (Table 1).

| SEQ ID NO. | Name | Sequence |
| --- | --- | --- |
| SEQ ID NO: 147 | SC1 100-300-100 donor | GATTGCCTCAGATCACACTATCTCCACTTGCCCAGCCCTGT<br>GGAAGATTAGCGGCCATGTATTCCAATGTGATAGGAACTGT<br>AACCTCTGGAAAAAGGTACGAATTCGAGGGCAGAGGCAGTC<br>TGCTGACATGCGGTGACGTGGAAGAGAATCCCGGCCCTTCT<br>AGATAACTGTGCCTTCTAGTTGCCAGCCATCTGTTGTTTGC<br>CCCTCCCCCGTGCCTTCCTTGACCCTGGAAGGTGCCACTCC<br>CACTGTCCTTTCCTAATAAAATGAGGAAATTGCATCGCATT<br>GTCTGAGTAGGTGTCATTCTATTCTGGGGGGTGGGGTGGGG<br>CAGGACAGCAAGGGGGAGGATTGGGAAGACAATAGCAGGCA<br>TGCTGGGGATGCGGTGGGCTCTATGCGGTACCAGAGGGGT<br>GAGCTTTCCCCTTGCCTGCCCCTACTGGGTTTTGTGACCTC<br>CAAAGGACTCACAGGAATGACCTCCAACACCTTTGAGAAGA<br>CCAGGCCCTC |
| SEQ ID NO: 148 | SC1 100-500-100 donor | GATTGCCTCAGATCACACTATCTCCACTTGCCCAGCCCTGT<br>GGAAGATTAGCGGCCATGTATTCCAATGTGATAGGAACTGT |

TABLE 7-continued

Sequences of Primers and Templates used in Example 7. SEQ ID NO: 22 used for SERPINC1 crRNA (Table 1).

| SEQ ID NO. | Name | Sequence |
|---|---|---|
| | | AACCTCTGGAAAAAGGTACGAATTCGAGGGCAGAGGCAGTC<br>TGCTGACATGCGGTGACGTGGAAGAGAATCCCGGCCCTTCT<br>AGAATGGTTAGCAAGGGCGAGGAGCTGTTCACCGGGGTGGT<br>GCCCATCCTGGTCGAGCTGGACGGCGACGTAAACGGCCACA<br>AGTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTAAC<br>TGTGCCTTCTAGTTGCCAGCCATCTGTTGTTTGCCCCTCCC<br>CCGTGCCTTCCTTGACCCTGGAAGGTGCCACTCCCACTGTC<br>CTTTCCTAATAAAATGAGGAAATTGCATCGCATTGTCTGAG<br>TAGGTGTCATTCTATTCTGGGGGGTGGGTGGGGCAGGACA<br>GCAAGGGGGAGGATTGGGAAGACAATAGCAGGCATGCTGGG<br>GATGCGGTGGGCTCTATGGCGGTACCAGAGGGGTGAGCTTT<br>CCCCTTGCCTGCCCCTACTGGGTTTTGTGACCTCCAAAGGA<br>CTCACAGGAATGACCTCCAACACCTTTGAGAAGACCAGGCC<br>CTC |
| SEQ ID NO: 1<br>SEQ ID NO: 149 | SC1 100-1000-100<br>donor2 | GATTGCCTCAGATCACACTATCTCCACTTGCCCAGCCCTGT<br>GGAAGATTAGCGGCCATGTATTCCAATGTGATAGGAACTGT<br>AACCTCTGGAAAAAGGTACGAATTCGAGGGCAGAGGCAGTC<br>TGCTGACATGCGGTGACGTGGAAGAGAATCCCGGCCCTTCT<br>AGAATGGTTAGCAAGGGCGAGGAGCTGTTCACCGGGGTGGT<br>GCCCATCCTGGTCGAGCTGGACGGCGACGTAAACGGCCACA<br>AGTTCAGCGTGTCCGGCGAGGGCGAGGGCGATGCCACCTAC<br>GGCAAGCTGACCCTGAAGTTCATCTGCACCACCGGCAAGCT<br>GCCCGTGCCCTGGCCCACCCTCGTGACCACCCTGACCTACG<br>GCGTGCAGTGCTTCAGCCGCTACCCCGACCACATGAAGCAG<br>CACGACTTCTTCAAGTCCGCCATGCCCGAAGGCTACGTCCA<br>GGAGCGCACCATCTTCTTCAAGGACGACGGCAACTACAAGA<br>CCCGCGCCGAGGTGAAGTTCGAGGGCGACACCCTGGTGAAC<br>CGCATCGAGCTGAAGGGCATCGACTTCAAGGAGGACGGCAA<br>CATCCTGGGGCACAAGCTTGAGTACAACTACAACAGCCACA<br>ACGTCTATATCATGGCCGACAAGCAGAAGAACGGCATCAAG<br>GTGAACTTCAAGATCCGCCACAACATCGAGGACGGCAGCGT<br>GCAGCTCGCCGACCACTACCAGCAGAACACCCCCATCGGCG<br>ACGGCCCCGTGCTGCTGCCCGACAACCACTACCTGAGCACC<br>CAGTCCGCCCTGAGCAAAGACCCCAACGAGAAGCGCGATCA<br>CATGGTCCTGCTGGAGTTCGTGACCGCCGCCGGGATCACTC<br>TCGGCATGGACGAGCTGTACAAGTAACTGTGCCTTCTAGTT<br>GCCAGCCATCTGTTGTTTGCCCCTCCCCCGTGCCTTCCTTG<br>ACCCTGGAAGGTGCCACTCCCACTGTCCTTTCCTAATAAAA<br>TGAGGAAATTGCATCGCATTGTCTGAGTAGGTGTCATTCTA<br>TTCTGGGGGGTGGGTGGGGCAGGACAGCAAGGGGGAGGAT<br>TGGGAAGACAATAGCAGGCATGCTGGGGATGCGGTGGGCTC<br>TATGGCGGTACCAGAGGGGTGAGCTTTCCCCTTGCCTGCCC<br>CTACTGGGTTTTGTGACCTCCAAAGGACTCACAGGAATGAC<br>CTCCAACACCTTTGAGAAGACCAGGCCCTC |
| SEQ ID NO: 150 | EMX 1 100-300-100<br>donor | CTCCCTCCCTGGCCCAGGTGAAGGTGTGGTTCCAGAACCGG<br>AGGACAAAGTACAAACGGCAGAAGCTGGAGGAGGAAGGGCC<br>TGAGTCCGAGCAGAAGAACGAATTCGAGGGCAGAGGCAGTC<br>TGCTGACATGCGGTGACGTGGAAGAGAATCCCGGCCCTTCT<br>AGATAACTGTGCCTTCTAGTTGCCAGCCATCTGTTGTTTGC<br>GCCTCACTCGTGCCTTCATTGACCCTGGAAGGTGCCACTCC<br>CACTGTCCTTTCCTAATAAAATGAGGAAATTGCATCGCATT<br>GTCTGAGTAGGTGTCATTCTATTCTGGCGTATCGAGTGGCT<br>CAGGACAGCAAGAGCGAGGATTGGGAAGACAATAGCAGGCA<br>TGCTGGGGATGCGGTGGGCTCTATGGCGGTACCGAAGGGCT<br>CCCATCACATCAACCGGTGGCGCATTGCCACGAAGCAGGCC<br>AATGGGGAGGACATCGATGTCACCTCCAATGACTAGGGTGG<br>GCAACCACAA |
| SEQ ID NO: 151 | EMX1 100-500-100<br>donor | CTCCCTCCCTGGCCCAGGTGAAGGTGTGGTTCCAGAACCGG<br>AGGACAAAGTACAAACGGCAGAAGCTGGAGGAGGAAGGGCC<br>TGAGTCCGAGCAGAAGAACGAATTCGAGGGCAGAGGCAGTC<br>TGCTGACATGCGGTGACGTGGAAGAGAATCCCGGCCCTTCT<br>AGAATGGTTAGCAAGGGCGAGGAGCTGTTCACCGGGGTGGT<br>GCCCATCCTGGTCGAGCTGGACGGCGACGTAAACGGCCACA<br>AGTTCAGCGTGTCCGGCGAGGGAGAGGGCGATGCCACCTAC<br>GGCAAGCTGACCCTGAAGTTCATCTGCACCACCGGCAAGCT<br>GCCAGTGCCCTGGCCTACCCTCGTGACCACCCTGACCTAAC<br>TGTGCCTTCTAGTTGCCAGCCATCTGTTGTTTGCGCCTCAC<br>TCGTGCCTTCATTGACCCTGGAAGGTGCCACTCCCACTGTC<br>CTTTCCTAATAAAATGAGGAAATTGCATCGCATTGTCTGAG<br>TAGGTGTCATTCTATTCTGGCGTATCGAGTGGCTCAGGACA |

TABLE 7-continued

Sequences of Primers and Templates used in Example 7. SEQ ID NO: 22 used for SERPINC1 crRNA (Table 1).

| SEQ ID NO. | Name | Sequence |
|---|---|---|
| | | GCAAGAGCGAGGATTGGGAAGACAATAGCAGGCATGCTGGG GATGCGGTGGGCTCTATGGCGGTACCGAAGGGCTCCCATCA CATCAACCGGTGGCGCATTGCCACGAAGCAGGCCAATGGGG AGGACATCGATGTCACCTCCAATGACTAGGGTGGGCAACCA CAA |
| SEQ ID NO: 152 | EMX1 100-1000-100 donor | CTCCCTCCCTGGCCCAGGTGAAGGTGTGGTTCCAGAACCGG AGGACAAAGTACAAACGGCAGAAGCTGGAGGAGGAAGGGCC TGAGTCCGAGCAGAAGAACGAATTCGAGGGCAGAGGCAGTC TGCTGACATGCGGTGACGTGGAAGAGAATCCCGGCCCTTCT AGAATGGTTAGCAAGGGCGAGGAGCTGTTCACCGGGGTGGT GCCCATCCTGGTCGAGCTGGACGGCGACGTAAACGGCCACA AGTTCAGCGTGTCCGGCGAGGGAGAGGGCGATGCCACCTAC GGCAAGCTGACCCTGAAGTTCATCTGCACCACCGGCAAGCT GCCAGTGCCCTGGCCTACCCTCGTGACCACCCTGACCTACG GCGTGCAGTGCTTCAGCCGCTACCCCGACCACATGAAGCAG CACGACTTCTTCAAGTCCGCCATGCCCGAAGGCTACGTCCA GGAGCGCACCATCTTCTTCAAGGACGACGGCAACTACAAGA CCCGTGCCGAGGTGAAGTTCGAAGGCGACACCCTGGTGAAC CGCATCGAGCTGAAGGGCATCGACTTCAAGGAGGACGGCAA CATCCTGGGGCACAAGCTTGAGTACAACTACAACAGCCACA ACGTCTATATCATGGCCGACAAGCAGAAGAACGGCATCAAG GTGAACTTCAAGATCCGCCACAACATCGAGGACGGTAGCGT GCAGCTCGCTGACCACTACCAGCAGAACACTCCTATCGGAG ACGGTCCTGTGCTGCTGCCAGACAACCACTACCTGAGCACA CAGTCCGCTCTGAGCAAAGACCCTAACGAGAAGCGCGATCA CATGGTCCTGCTGGAGTTCGTGACAGCCGCTGGGATCACTC TCGGCATGGACGAGCTGTACAAGTAACTGTGCCTTCTAGTT GCCAGCCATCTGTTGTTTGCGCCTCACTCGTGCCTTCATTG ACCCTGGAAGGTGCCACTCCCACTGTCCTTTCCTAATAAAA TGAGGAAATTGCATCGCATTGTCTGAGTAGGTGTCATTCTA TTCTGGCGTATCGAGTGGCTCAGGACAGCAAGAGCGAGGAT TGGGAAGACAATAGCAGGCATGCTGGGGATGCGGTGGGCTC TATGGCGGTACCGAAGGGCTCCCATCACATCAACCGGTGGC GCATTGCCACGAAGCAGGCCAATGGGGAGGACATCGATGTC ACCTCCAATGACTAGGGTGGGCAACCACAA |
| SEQ ID NO: 2 SEQ ID NO: 153 | SC1 100 Fwd unmod2 | GATTGCCTCAGATCACACTATCTCCACTTGCC |
| SEQ ID NO: 3 SEQ ID NO: 154 | SC1 100 Rev unmod2 | GAGGGCCTGGTCTTCTCAAAGGTGTTG |
| SEQ ID NO: 20 SEQ ID NO: 155 | SC1 100 Fwd MOE2 | MGATTGCCTCAGATCACACTATCTCCACTTGCC |
| SEQ ID NO: 21 SEQ ID NO: 156 | SC1 100 Rev MOE2 | MGAGGGCCTGGTCTTCTCAAAGGTGTTG |
| SEQ ID NO: 157 | EMX1 100 Fwd unmod | CTCCCTCCCTGGCCCAGGTGAAG |
| SEQ ID NO: 158 | EMX1 100 Rev unmod | TTGTGGTTGCCCACCCTAGTCATTGGA |
| SEQ ID NO: 159 | EMX1 100 Fwd MOE | MCTCCCTCCCTGGCCCAGGTGAAG |
| SEQ ID NO: 160 | EMX1 100 Rev MOE | MTTGTGGTTGCCCACCCTAGTCATTGGA |
| SEQ ID NO: 161 | EMX1 guide protospacer | GAGTCCGAGCAGAAGAAGAA |
| SEQ ID NO: 162 | SC1 ONT For | TTTCTGTTGGTGCTGATATTGCCTTTATGTGATTGCTGTAT GTCTCC |
| SEQ ID NO: 163 | SC1 ONT Rev | ACTTGCCTGTCGCTCTATCTTCGAATCTGCCAGGTGCTGAT A |
| SEQ ID NO: 164 | EMX1 ONT For | TTTCTGTTGGTGCTGATATTGCCTGTGCTTTACCCAGTTCT CT |
| SEQ ID NO: 165 | EMX1 ONT Rev | ACTTGCCTGTCGCTCTATCTTCGCTGGGTCTCTGACATCTT T |

DNA is uppercase; and 2'-O-methoxyethyl modified ribonucleotides are shown with an uppercase M preceeding the modified ribonucleotide. SC1 is SERPINC1. All primers and templates were synthesized by IDT (Coralville, IA).

1xMOE modified donors resulted in higher HDR rates (on average from 28.6% to 30.9% at EMX1 and 44.4% to 53.6% at SERPINC1) and lower blunt integration rates (on average from 3.2% to 1.1% at EMX1 and 8.4% to 2.5% at SERPINC1) when compared to unmodified dsDNA donors mediating large insertions at both genomic loci. Long ssDNA donors mediating the same insertions at the SERPINC1 locus resulted in extremely low blunt integration rates (<1%). The long ssDNA donor mediated the highest rates of HDR for the 300 bp insert (71.3% vs. 54.9% with a modified dsDNA donor). However, the modified dsDNA donor performed as well or better than the long ssDNA for HDR with the larger insertions (55.2% vs. 53.3% for a 500 bp insert, 50.8% vs. 29.4% for a 1000 bp insert). Similar trends were observed for the SERPINC1 samples when an orthologous method of assessment was used (FIG. 9B).

Example 8

Utilization of Universal Priming Sequences for Manufacturing Modified dsDNA Donors does not Adversely Affect HDR Repair.

Figure 10:
FIG. 10 shows a schematic of dsDNA HDR donor template design comprising universal priming sequences. Hashed black indicates DNA sequence that is homologous between the genomic DNA target and the HDR donor (i.e., homology arms). Black indicates the desired insert DNA sequence. White indicates DNA sequence homologous to the universal priming sequences.
Figure 11:
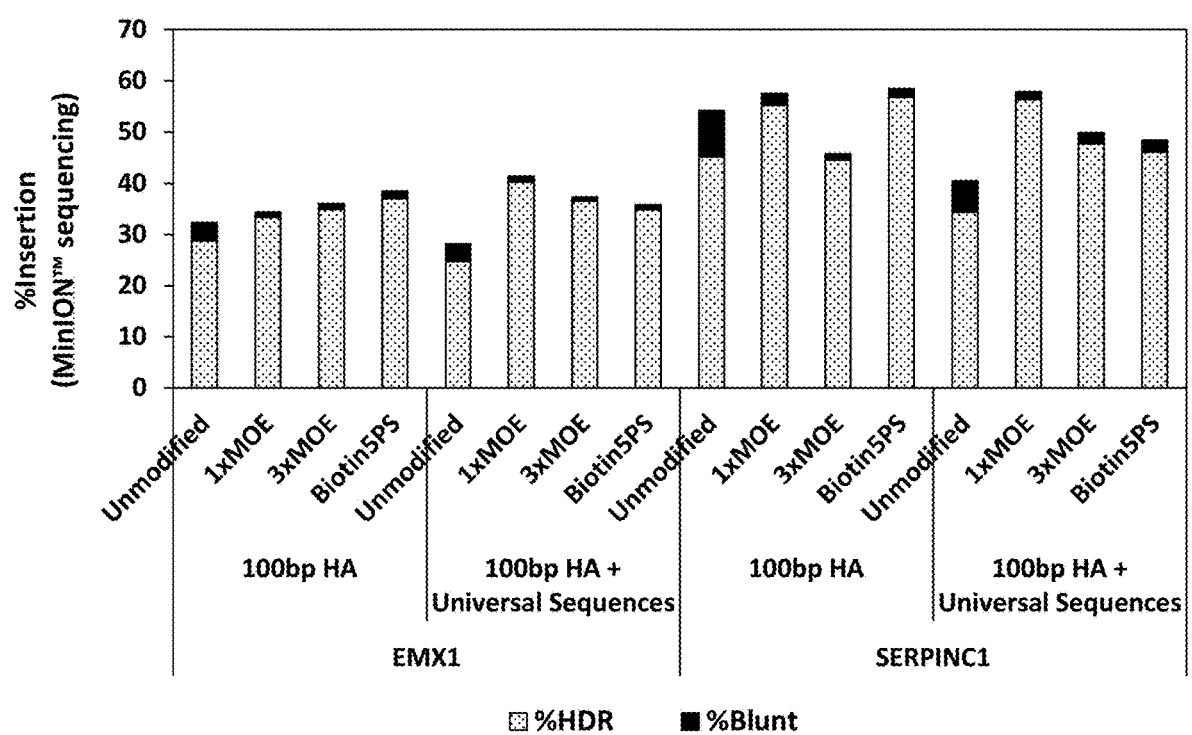
FIG. 11 shows an assessment of dsDNA donor integration via HDR or NHEJ pathways using modified linear dsDNA donors composed of a 500 bp insert flanked by 100 bp homology arms. Donors were synthesized with or without terminal universal priming sequences.

To assess the impact of incorporating universal priming sequences into the donor template, dsDNA donors mediating a 500 bp insert at EMX1 and SERPINC1 (see Table 7, SEQ ID NO: 148 and 151) were prepared with either locus specific primers or with universal primers (Table 7 SEQ ID NO: 153-160; Table 8 SEQ ID NO: 166-181). Placement of the universal priming sequences relative to the donor is shown in FIG. 10. Modifications tested included 1xMOE, 3xMOE, and Biotin with phosphorothioate modifications (Biotin5xPS, as described in [5]). Donors were delivered at 100 nM in a final volume of 28 μL nucleofection buffer with 2 μM Cas9 V3™ RNP (IDT, Coralville, Iowa) targeting SERPINC1 or EMX1 into 3.5×10⁵ HEK-293 cells using Lonza nucleofection (Lonza, Basel, Switzerland). Cells were treated with the IDT Alt-R™ HDR Enhancer V2 (1 μM) for 24 hrs post-transfection. Cells were lysed after 48 hours using QuickExtract™ DNA extraction solution (Lucigen, Madison, WI). HDR and blunt integration rates were assessed by long-read sequencing using the MinION™ platform (Oxford Nanopore Technologies, Oxford, UK) and analyzed as previously described (FIG. 11).

TABLE 8

Sequences of Primers for dsDNA Donor Synthesis in Example 8

| SEQ ID NO. | Name | Sequence |
|---|---|---|
| SEQ ID NO: 166 | SC1 100 Fwd 3 x MOE | MGMAMTTGCC TCAGATCACA CTATCTCCAC TTGCC |
| SEQ ID NO: 167 | SC1 100 Rev 3 x MOE | MGMAMGGGCC TGGTCTTCTC AAAGGTGTTG |
| SEQ ID NO: 168 | SC1 100 Fwd Biotin5PS | B-G*A*T*T* G*CCTCAGAT CACACTATCT CCACTTGCC |
| SEQ ID NO: 169 | SC1 100 Rev Biotin5 x PS | B-G*A*G*G* G*CCTGGTCT TCTCAAAGGT GTTG |
| SEQ ID NO: 170 | EMX1 100 Fwd 3 x MOE | MCMTMCCCTC CCTGGCCCAG GTGAAG |
| SEQ ID NO: 171 | EMX1 100 Rev 3 x MOE | MTMTMGTGGT TGCCCACCCT AGTCATTGGA |
| SEQ ID NO: 172 | EMX1 100 Fwd Biotin5 x PS | B-C*T*C*C* C*TCCCTGGC CCAGGTGAAG |
| SEQ ID NO: 173 | EMX1 100 Rev Biotin5 x PS | B-T*T*G*T* G*GTTGCCCA CCCTAGTCAT TGGA |
| SEQ ID NO: 174 | Universal For unmod | GTCGTACCGA CTGGTAGATG ACAGCAAACC |
| SEQ ID NO: 175 | Universal Rev unmod | GGTCTCGACT ATACGCCCGT TTTCGGATC |
| SEQ ID NO: 176 | Universal For 1 x MOE | MGTCGTACCG ACTGGTAGAT GACAGCAAAC C |
| SEQ ID NO: 177 | Universal Rev 1 x MOE | MGGTCTCGAC TATACGCCCG TTTTCGGATC |
| SEQ ID NO: 178 | Universal For 3 x MOE | MGMTMCGTAC CGACTGGTAG ATGACAGCAA ACC |
| SEQ ID NO: 179 | Universal Rev 3 x MOE | MGMGMTCTCG ACTATACGCC CGTTTTCGGA TC |
| SEQ ID NO: 180 | Universal For Biotin5 x PS | B-G*T*C*G* T*ACCGACTG GTAGATGACA GCAAACC |
| SEQ ID NO: 181 | Universal Rev Biotin5 x PS | B-G*G*T*C* T*CGACTATA CGCCCGTTTT CGGATC |

DNA is uppercase; 2'-O-methoxyethyl modified ribonucleotides are shown with an uppercase M preceeding the modified ribonucleotide; B- is a 5'-biotin moiety; and phosphorothioate (PS) modified linkages are shown with an asterisk (*). SC1 is SERPINC1. All primers and templates were synthesized by IDT (Coralville, IA).

HDR and blunt integration rates were relatively similar for dsDNA donors generated with or without the universal priming sequences. For donors without universal priming sequences, the improvement to HDR and reduction in blunt rates were similar across the various modifications. The major exception to this trend was the 3×MOE modification for the SERPINC1 site, where blunt insertion was still reduced relative to an unmodified dsDNA but HDR was not improved to the same extent as 1×MOE or Biotin5×PS (unmod: 45.1% HDR, 9.0% Blunt; 1×MOE: 55.2% HDR, 2.3% Blunt, 3×MOE: 44.5% HDR, 1.2% Blunt). In contrast, a much larger difference in performance was observed with the modified donors manufactured with the universal priming sequences. Interestingly, the unmodified dsDNA donors for both sites had lower integration rates when universal priming sites were included in the donor sequence (EMX1: 28.8% vs 24.8% HDR, SERPINC1: 45.2% vs 34.4% HDR). For both sites, the 1×MOE modification offered the greatest improvement to the HDR rate when incorporated into donors containing the universal sequences.

Figure 12A:
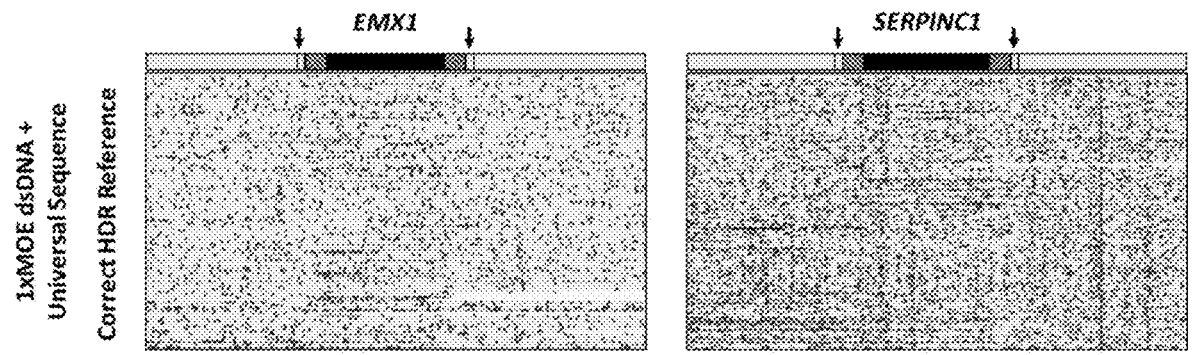
FIG. 12A-C show a visual assessment of HDR reads from 1xMOE donors using IGV. HDR reads from the EMX1 and SERPINC1 1xMOE dsDNA donors manufactured with the universal priming sequences were aligned against a reference containing either the correct HDR sequence (FIG. 12A) or the HDR sequence with the universal sequences (i.e., incorrect HDR) (FIG. 12B). For comparison, HDR reads from the 1xMOE dsDNA donors lacking universal sequences were aligned against the correct HDR reference (FIG. 12C). Within the IGV plots, individual reads are represented as thin horizontal lines. Individual nucleotides that do not correctly align to the reference (i.e., insertions, gaps, or mutations) are marked in black. The background error rate from the MinION™ sequencing can be assessed in FIG. 12C. A representation of the HDR reference is shown above each IGV panel. Solid black represents the desired 500 bp insert. Dashed areas represent sequence homologous to the 100 bp donor homology arms. Dotted areas represent the 30 bp universal priming sequences. Areas of interest are indicated by arrows. Misalignments against the incorrect HDR reference (FIG. 12B) are evident in every HDR read, indicating a lack of the 30 bp universal sequences after the repair. Panels for EMX1 donors represent approximately 500 reads. Panels for SERPINC1 donors represent approximately 3700 reads.
Figure 12B:
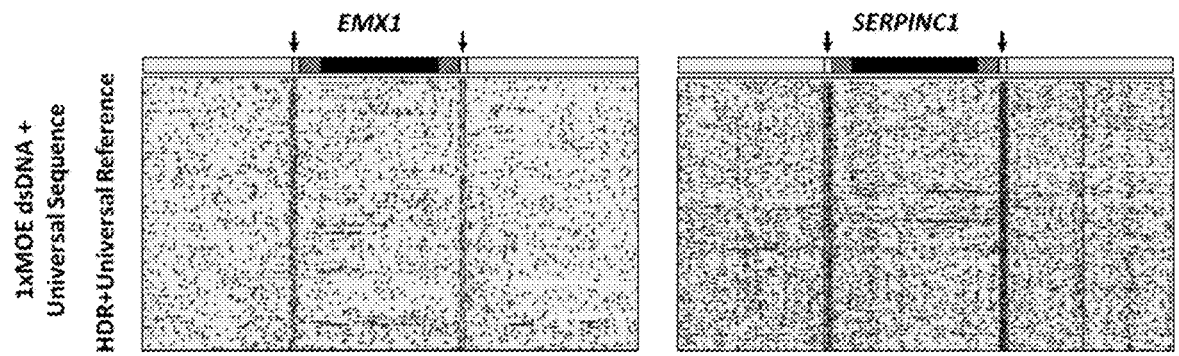

Further analysis of the HDR reads from the 1×MOE modified donors was conducted in the Integrative Genomics Viewer [7] (IGV, Broad Institute, Cambridge, MA). When HDR reads were aligned against either a reference amplicon containing the correct HDR sequence (FIG. 12A) or a reference amplicon containing both the desired insert and the universal priming sequences (FIG. 12B), no evidence of universal sequence incorporation was observed in the HDR reads. Thus, the universal sequences can be incorporated into the manufacturing process of modified dsDNA donors without adversely impacting functional performance.

Example 9

Use of Modified dsDNA Donors Manufactured with Universal Priming Sequences to Generate GFP Fusions in Human Cell Lines.

Figure 12C:
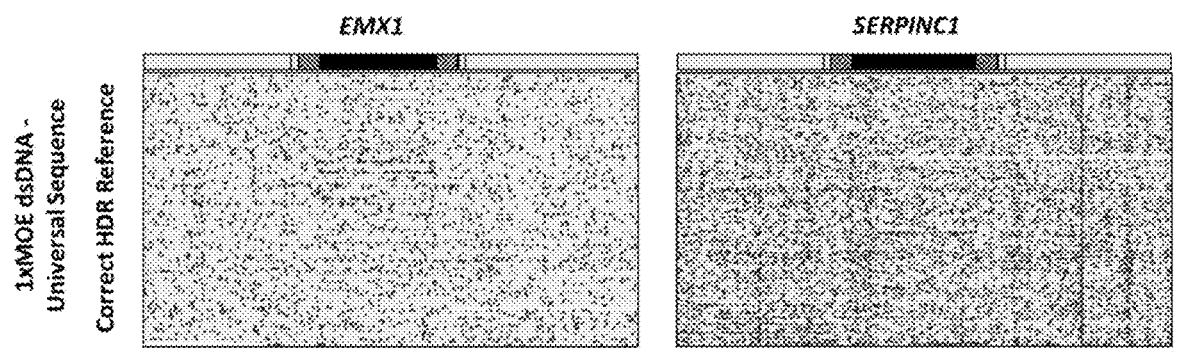
Figure 13:
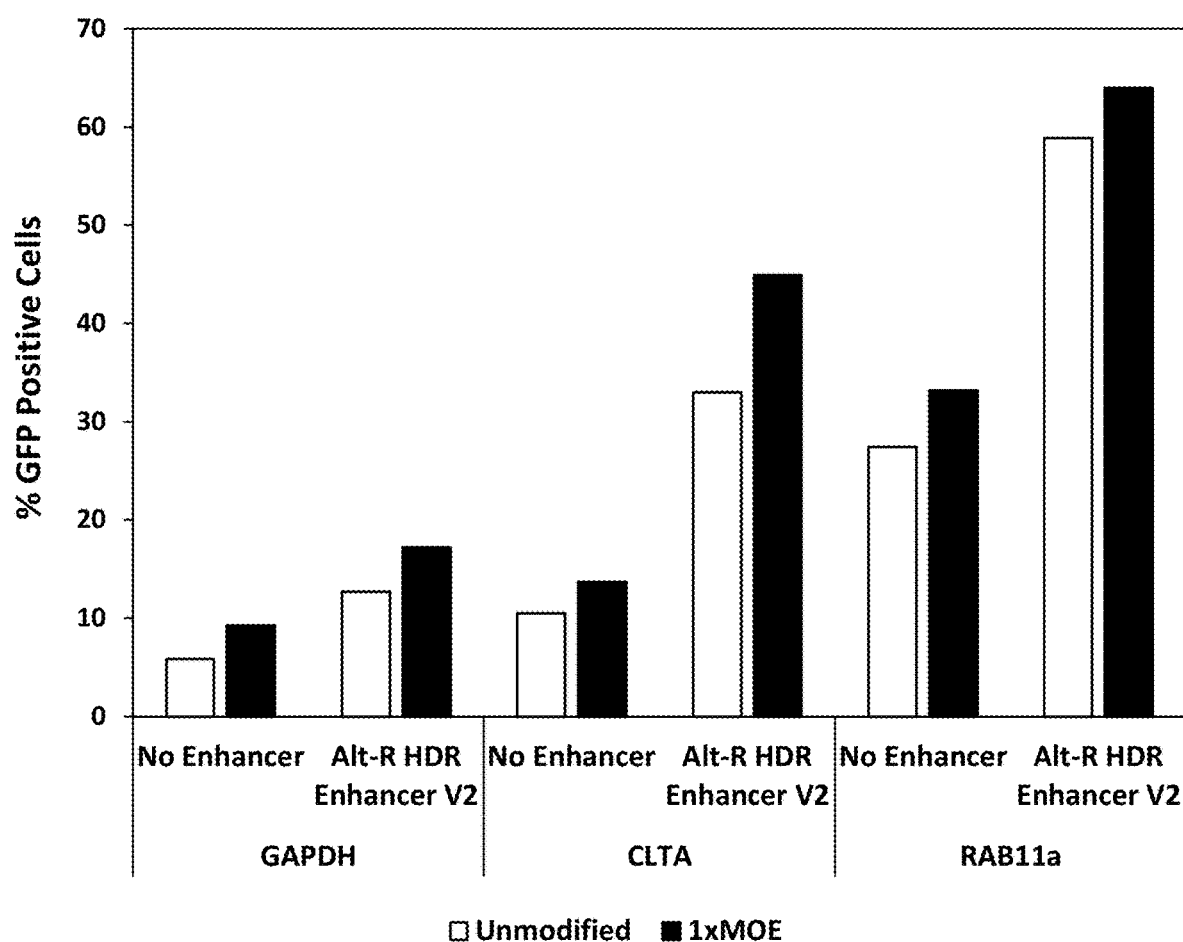
FIG. 13 shows an assessment of HDR rates when using either unmodified or 1xMOE modified dsDNA donor templates. Donors were designed to insert GFP at the N- or C-terminus of the target genes and contained 200 bp homology arms. Donors were generated with universal priming sequences. HDR rates were assessed by flow cytometry (reported as % GFP positive cells).

To assess the functional performance of modified dsDNA donor templates in applications such as protein tagging, donors were designed to generate GFP tagged GAPDH (C-terminal fusion), CLTA (N-terminal fusion), and RAB11a (N-terminal fusion). Donors were manufactured with universal priming sequences as previously described, using either unmodified or 1×MOE modified primers. Guide and donor sequences used are listed in Table 9. Donors were delivered at 50 nM in a final volume of 28 µL nucleofection buffer with 2 µM Cas9 V3™ RNP (IDT, Coralville, Iowa) targeting GAPDH, CLTA, or RAB11a into $3.5 \times 10^5$ K562 cells using Lonza nucleofection (Lonza, Basel, Switzerland). Following the transfection, cells were plated in duplicate wells. For one set of wells, cells were treated with the IDT Alt-R™ HDR Enhancer V2 (1 µM) for 24 hrs post-transfection. Cells were passaged for 7 days, at which point HDR rates were assessed by flow cytometry. Briefly, cells were washed in PBS and then resuspended at $1-2 \times 10^6$ cells/mL. Hoechst 33258 was added to the cell suspension at a final concentration of 4 µg/ml shortly before analysis for viability staining. Cells were analyzed on a Becton Dickinson LSR II cytometer (BD Bioscience, San Jose, CA) to assess GFP expression levels (FIG. 12).

TABLE 9

Sequences of Primers for dsDNA Donor Synthesis in Example 9

| SEQ ID NO. | Name | Sequence |
| --- | --- | --- |
| SEQ ID NO: 182 | GAPDH C-term GFP donor | AACGACCACTTTGTCAAGCTCATTTCCTGGTATGTGGCTGGGGC CAGAGACTGGCTCTTAAAAAGTGCAGGGTCTGGCGCCCTCTGGT GGCTGGCTCAGAAAAAGGGCCCTGACAACTCTTTTCATCTTCTA GGTATGACAACGAATTTGGCTACAGCAACAGGGTGGTGGACCTC ATGGCCCACATGGCCTCCAAGGAGGGATCTGGCGCCACCAATTT CAGCCTGCTGAAACAGGCTGGCGACGTGGAAGAGAACCCTGGAC CTGTGAGCAAGGGCGAGGAGCTGTTCACCGGGGTGGTGCCCATC CTGGTCGAGCTGGACGGCGACGTAAACGGCCACAAGTTCAGCGT GTCCGGCGAGGGCGAGGGCGATGCCACCTACGGCAAGCTGACCC TGAAGTTCATCTGCACCACCGGCAAGCTGCCCGTGCCCTGGCCC ACCCTCGTGACCACCCTGACCTACGGCGTGCAGTGCTTCAGCCG CTACCCCGACCACATGAAGCAGCACGACTTCTTCAAGTCCGCCA TGCCCGAAGGCTACGTCCAGGAGCGCACCATCTTCTTCAAGGAC GACGGCAACTACAAGACCCGCGCCGAGGTGAAGTTCGAGGGCGA CACCCTGGTGAACCGCATCGAGCTGAAGGGCATCGACTTCAAGG AGGACGGCAACATCCTGGGGCACAAGCTGGAGTACAACTACAAC AGCCACAACGTCTATATCATGGCCGACAAGCAGAAGAACGGCAT CAAGGTGAACTTCAAGATCCGCCACAACATCGAGGACGGCAGCG TGCAGCTCGCCGACCACTACCAGCAGAACACCCCCATCGGCGAC GGCCCCGTGCTGCTGCCCGACAACCACTACCTGAGCACCCAGTC CGCCCTGAGCAAAGACCCCAACGAGAAGCGCGATCACATGGTCC TGCTGGAGTTCGTGACCGCCGCCGGGATCACTCTCGGCATGGAC GAGCTGTACAAGTAAGACCCCTGGACCACCAGCCCCAGCAAGAG CACAAGAGGAAGAGAGAGACCCTCACTGCTGGGGAGTCCCTGCC ACACTCAGTCCCCCACCACACTGAATCTCCCCTCCTCACAGTTG CCATGTAGACCCCTTGAAGAGGGGAGGGGCCTAGGGAGCCGCAC CTTGTCATGTACCATCAATAAAGTACCCTGTGCTCA |
| SEQ ID NO: 183 | CLTA N-term GFP donor | GTCGTACCGACTGGTAGATGACAGCAAACCTGTTCCCTTTTCGG CTCTGCAACACCGCCTAGACCGACCGGATACACGGGTAGGGCTT CCGCTTTACCCGTCTCCCTCCTGGCGCTTGTCCTCCTCTCCCAG TCGGCACCACAGCGGTGGCTGCCGGGCGTGGTGTCGGTGGGTCG GTTGGTTTTTGTCTCACCGTTGGTGTCCGTGCCGTTCAGTTGCC CGCCATGGCTGGATCTGGTGGTACTAGTGGAAGCAAGGGTGAGG AGCTGTTCACCGGAGTGGTGCCTATCCTGGTCGAGCTGGACGGC GACGTAAACGGTCACAAGTTCAGCGTGCGTGGTGAGGGCGAGGG CGATGCCACCAACGGCAAGCTGACCCTGAAGTTCATCTGCACCA |

TABLE 9-continued

Sequences of Primers for dsDNA Donor Synthesis in Example 9

| SEQ ID NO. | Name | Sequence |
|---|---|---|
| | | CTGGCAAGCTGCCTGTTCCATGGCCAACCCTCGTGACTACACTG<br>ACCTACGGCGTTCAGTGCTTCAGCCGTTACCCTGACCATATGAA<br>GCGTCACGACTTCTTCAAGTCTGCCATGCCTGAAGGCTACGTCC<br>AGGAGCGTACCATCAGCTTCAAGGACGATGGCACCTACAAGACT<br>CGTGCCGAGGTGAAGTTCGAGGGTGACACCCTGGTGAACCGCAT<br>CGAGCTGAAGGGTATCGACTTCAAGGAGGACGGCAACATCCTGG<br>GTCACAAGCTGGAGTACAACTTCAACAGCCACAACGTCTATATC<br>ACCGCCGACAAGCAGAAGAACGGCATCAAGGCCAACTTCAAGAT<br>TCGTCACAACGTGGAGGACGGTAGCGTGCAGCTCGCAGACCACT<br>ACCAGCAGAACACGCCTATCGGCGACGGTCCAGTGTTGCTGCCA<br>GACAACCACTACCTGAGCACCCAGTCCGTGCTGAGCAAAGACCC<br>GAACGAGAAGCGCGATCACATGGTCCTGCTGGAGTTCGTGACCG<br>CAGCCGGTATCACTGGAACCGGTGCTGGAAGTGGTGAGCTGGAT<br>CCGTTCGGCGCCCCTGCCGGCGCCCCTGGCGGTCCCGCGCTGGG<br>GAACGGAGTGGCCGGCGCCGGCGAAGAAGACCCGGCTGCGGCCT<br>TCTTGGCGCAGCAAGAGAGCGAGATTGCGGGCATCGAGAACGAC<br>GAGGCCTTCGCCATCCTGGACGGCGGCGCCCCCGGGCCCCAGCC<br>GCACGGCGAGCCGCCGATCCGAAAACGGGCGTATAGTCGAGACC |
| SEQ ID NO: 184 | RAB11a N-term GFP donor | TCAGGGGCGGGGCGCCGCCCCCGGAAGTACTTCCCCTTAAAGGC<br>TGGGGCCTGCCGGAAATGGCGCAGCGGCAGGGAGGGGCTCTTCA<br>CCCAGTCCGGCAGTTGAAGCTCGGCGCTCGGGTTACCCCTGCAG<br>CGACGCCCCTGGTCCCACAGATACCACTGCTGCTCCCGCCCTT<br>TCGCTCCTCGGCCGCGCAATGGGCGGATCGGGTGGGACTAGTGG<br>CAGCAAGGGCGAGGAGCTGTTCACCGGGGTGGTGCCCATCCTGG<br>TCGAGCTGGACGGCGACGTAAACGGCCACAAGTTCAGCGTGCGC<br>GGCGAGGGCGAGGGCGATGCCACCAACGGCAAGCTGACCCTGAA<br>GTTCATCTGCACCACCGGCAAGCTGCCCGTGCCCTGGCCCACCC<br>TCGTGACCACCCTGACCTACGGCGTGCAGTGCTTCAGCCGCTAC<br>CCCGACCACATGAAGCGCCACGACTTCTTCAAGTCCGCCATGCC<br>CGAAGGCTACGTCCAGGAGCGCACCATCAGCTTCAAGGACGACG<br>GCACCTACAAGACCCGCGCCGAGGTGAAGTTCGAGGGCGACACC<br>CTGGTGAACCGCATCGAGCTGAAGGGCATCGACTTCAAGGAGGA<br>CGGCAACATCCTGGGGCACAAGCTGGAGTACAACTTCAACAGCC<br>ACAACGTCTATATCACCGCCGACAAGCAGAAGAACGGCATCAAG<br>GCCAACTTCAAGATCCGCCACAACGTGGAGGACGGCAGCGTGCA<br>GCTCGCCGACCACTACCAGCAGAACACCCCCATCGGCGACGGCC<br>CCGTGCTGCTGCCCGACAACCACTACCTGAGCACCCAGTCCGTG<br>CTGAGCAAAGACCCCAACGAGAAGCGCGATCACATGGTCCTGCT<br>GGAGTTCGTGACCGCCGCCGGGATCACTGGAACCGGTGCTGGAA<br>GTGGTACACGCGACGACGAGTACGACTACCTCTTTAAAGGTGAG<br>GCCATGGGCTCTCGCACTCTACACAGTCCTCGTTCGGGGACCCG<br>GGCCACTCCCGGTGGACCCTCGTGCCGGCCACCCCTGCACTGAT<br>ATAGGCCTCCCTCAGCCCTTCCTTTTTGTGCGGTTCCGTCTCCT<br>ACCCAGCTCAGCCTCTTCTCCCCCGCTCA |
| SEQ ID NO: 185 | GAPDH guide protospacer | CCTCCAAGGAGTAAGACCCC |
| SEQ ID NO: 186 | CLTA guide protospacer | GAACGGATCCAGCTCAGCCA |
| SEQ ID NO: 187 | RAB11a guide protospacer | GGTAGTCGTACTCGTCGTCG |

DNA is uppercase. All primers and templates were synthesized by IDT (Coralville, IA).

Overall HDR rates varied across the sites tested, with maximum GFP positive rates of 17.2% (GAPDH), 44.9% (CLTA), and 64% (RAB11a) achieved under optimal conditions. No GFP signal was observed in cells that received a dsDNA donor without RNP (data not shown). HDR rates were increased with modified dsDNA donor templates in both untreated conditions (1.6, 1.3, and 1.2-fold improvement over unmodified dsDNA for GAPDH, CLTA, and RAB11a respectively) and in HDR Enhancer treated conditions (1.4, 1.4, and 1.1-fold improvements over unmodified dsDNA respectively). On average, use of 1×MOE modified dsDNA donors increased HDR rates 1.3-fold over unmodified dsDNA donors across all conditions. In comparison, use of the Alt-R HDR Enhancer V2 increased HDR rates on average 2.4-fold across all sites and conditions. The combined use of modified donors and HDR Enhancer boosted HDR rates 3.2-fold on average across all sites. Taken together, this demonstrates the combined utility of using optimal reagents (i.e. modified donors and small molecule enhancers) in HDR experiments.

Example 10

Figure 14A:
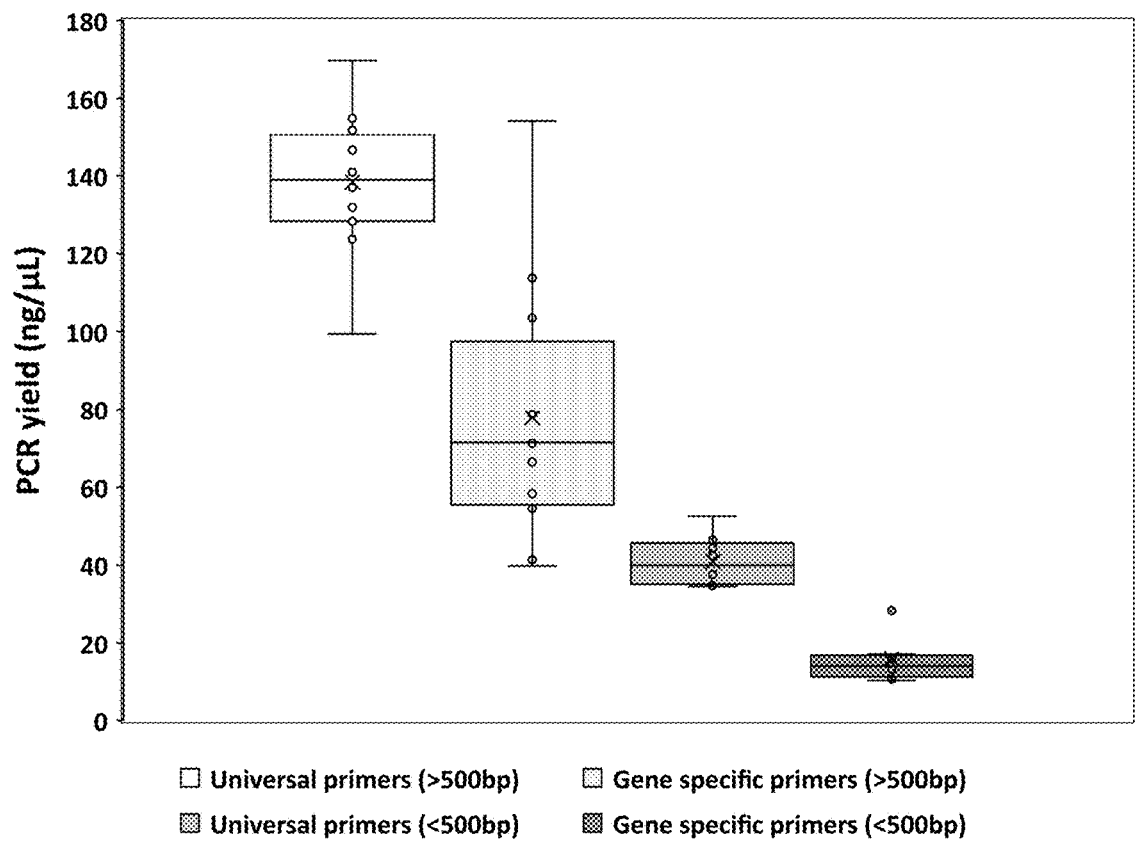
FIG. 14A-B show an assessment of yields when dsDNA HDR templates are manufactured with either universal primers or gene specific primers. Twelve sequences >500 bp and twelve sequences <500 bp were manufactured and PCR yields were assessed. Overall yields for each group are shown in FIG. 14A, while comparisons between templates with or without universal primers for each sequence are shown in FIG. 14B.

Use of Universal Priming Sequences Enables Greater Consistency and Improved Yields when Manufacturing dsDNA HDR Templates In order to assess the impact of universal priming sequences on the manufacturing process of dsDNA HDR templates, 24 sequences were generated using either universal priming sequences (Table 8, SEQ ID NO: 172-181) or gene specific primers (Table 10, SEQ ID NO: 188-235) with varying modifications. As previously described, all donors were produced by amplification from a plasmid (pUCIDT Amp or pUCIDT Kan vectors) containing the sequence of interest. PCR amplifications were conducted using KOD Hot Start DNA Polymerase (EMD) according to the manufacturer's recommendations, with 200 nM primers and 10 ng plasmid DNA in a 50 µL final reaction volume. Thermocycling was conducted using a Bio-Rad S1000 thermal cycler with the following cycling conditions: a 3 min incubation at 95° C., followed by 36 amplification cycles (95° C. for 20 sec; 65° C. for 10 sec; 70° C. for 20-30 sec/kb). Annealing temperatures were adjusted according to the gene specific primer melting temperatures. Following a SPRI bead cleanup, all products were analyzed using Fragment Analyzer (Agilent) and sequence verified by NGS using the Illumina-Nextera DNA Library Preparation Kit. Overall amplification efficiencies from universal primers or gene specific primers were assessed by measuring final yields, reported as ng/µL (FIG. 14A).

TABLE 10

Sequences of Primers for dsDNA Donor Synthesis in Example 10.

| SEQ ID NO. | Name | Sequence | Amplicon Length (bp) |
|---|---|---|---|
| SEQ ID NO: 188 | Gene specific F1 | ACGAAGTGTTGGATATAAGCCAGACTGTAAGTGA | 152 |
| SEQ ID NO: 189 | Gene specific R1 | TCTAAGCAATTATAAGCCATTTCACATAAAACTCTTTTAGGTTAAA | 152 |
| SEQ ID NO: 190 | Gene specific F2 | MACGAAGTGTTGGATATAAGCCAGACTGTAAGTGA | 152 |
| SEQ ID NO: 191 | Gene specific R2 | MTCTAAGCAATTATAAGCCATTTCACATAAAACTCTTTTAGGTTAAA | 152 |
| SEQ ID NO: 192 | Gene specific F3 | GCCCTGTAGTCTCTCTGTATGTTATATGTCACATTTTGTAA | 198 |
| SEQ ID NO: 193 | Gene specific R3 | AAGTAATTCACTTACAGTCTGGCTTATATCCAACACTTCG | 198 |
| SEQ ID NO: 194 | Gene specific F4 | MGCCCTGTAGTCTCTCTGTATGTTATATGTCACATTTTGTAA | 198 |
| SEQ ID NO: 195 | Gene specific R4 | MAAGTAATTCACTTACAGTCTGGCTTATATCCAACACTTCG | 198 |
| SEQ ID NO: 196 | Gene specific F5 | AGCTTGCTGGTGAAAAGGACCCCA | 282 |
| SEQ ID NO: 197 | Gene specific R5 | AATGTGCCTCTCTACAAATATTCTCTAAGCAATTATAAGCCATTTC | 282 |
| SEQ ID NO: 198 | Gene specific F6 | MAGCTTGCTGGTGAAAAGGACCCCA | 282 |
| SEQ ID NO: 199 | Gene specific R6 | MAATGTGCCTCTCTACAAATATTCTCTAAGCAATTATAAGCCATTTC | 282 |
| SEQ ID NO: 200 | Gene specific F7 | ACGTCAGTCTTCTCTTTTGTAATGCCCTGTAGTC | 951 |
| SEQ ID NO: 201 | Gene specific R7 | GATGGTTAAATGATTGACAAAAAAAGTAATTCACTTACAGTCTGG | 1456 |
| SEQ ID NO: 202 | Gene specific F8 | MACGTCAGTCTTCTCTTTTGTAATGCCCTGTAGTC | 2170 |
| SEQ ID NO: 203 | Gene specific R8 | MGATGGTTAAATGATTGACAAAAAAAGTAATTCACTTACAGTCTGG | 2170 |

TABLE 10-continued

Sequences of Primers for dsDNA Donor Synthesis in Example 10.

| SEQ ID NO. | Name | Sequence | Amplicon Length (bp) |
|---|---|---|---|
| SEQ ID NO: 204 | Gene specific F9 | TGTAGTCTCTCTGTATGT TATATGTCACATTTTGTA ATTAACAGCT | 2170 |
| SEQ ID NO: 205 | Gene specific R9 | ATTTAGATAAAGAAAACA TCACTTTTAAATCTAATA CTGGCAAATG | 2170 |
| SEQ ID NO: 206 | Gene specific F10 | MTGTAGTCTCTCTGTATG TTATATGTCACATTTTGT AATTAACAGCT | 2567 |
| SEQ ID NO: 207 | Gene specific R10 | MATTTAGATAAAGAAAAC ATCACTTTTAAATCTAAT ACTGGCAAATG | 2814 |
| SEQ ID NO: 208 | Gene specific F11 | CATGGTACACTCAGCACG GATGAAATGAAACAG | 2955 |
| SEQ ID NO: 209 | Gene specific R11 | AGCAATTATAAGCCATTT CACATAAAACTCTTTTAG GTTAAAGATG | 2955 |
| SEQ ID NO: 210 | Gene specific F12 | MCATGGTACACTCAGCA CGGATGAAATGAAACAG | 2955 |
| SEQ ID NO: 211 | Gene specific R12 | MAGCAATTATAAGCCATT TCACATAAAACTCTTTTA GGTTAAAGATG | 2955 |
| SEQ ID NO: 212 | Gene specific F13 | MTCTCAGATTCCAGTTTC AGCAAATTTGCTTGATAT GTACAGC | 152 |
| SEQ ID NO: 213 | Gene specific R13 | MTGAATAGAGTGGTTGCA CAAACTTACGGATCATTT G | 152 |
| SEQ ID NO: 214 | Gene specific F14 | MATGGTGAGCAAGGGCGA GGAGCT | 152 |
| SEQ ID NO: 215 | Gene specific R14 | MAGAGTGATCCCGGCGGC GGTCA | 152 |
| SEQ ID NO: 216 | Gene specific F15 | CCCACAATTCGCTCTCAC CAAACCTGAG | 198 |
| SEQ ID NO: 217 | Gene specific R15 | AGTAGTAATAGTAGTAGT ATTAAATAATTTGATAAA TAATTTTAGCAATATAGT TTTTGT | 198 |
| SEQ ID NO: 218 | Gene specific F16 | MCCCACAATTCGCTCTC ACCAAACCTGAG | 198 |
| SEQ ID NO: 219 | Gene specific R16 | MAGTAGTAATAGTAGTAG TATTAAATAATTTGATAA ATAATTTTAGCAATATAG TTTTTGT | 198 |
| SEQ ID NO: 220 | Gene specific F17 | MCMCMCACAATTCGCTCT CACCAAACCTGAG | 282 |
| SEQ ID NO: 221 | Gene specific R17 | MAMGMTAGTAATAGTAGT AGTATTAAATAATTTGAT AAATAATTTTAGCAATAT AGTTTTTGT | 282 |
| SEQ ID NO: 222 | Gene specific F18 | B-C*C*C*A*C*AATTC GCTCTCACCAAACCTGAG | 282 |

TABLE 10-continued

Sequences of Primers for dsDNA Donor Synthesis in Example 10.

| SEQ ID NO. | Name | Sequence | Amplicon Length (bp) |
|---|---|---|---|
| SEQ ID NO: 223 | Gene specific R18 | B-A*G*T*A*G*TAATAG TAGTAGTATTAAATAATT TGATAAATAATTTTAGCA ATATAGTTTTTGT | 282 |
| SEQ ID NO: 224 | Gene specific F19 | B-G*G*T*A*C*AAGTGG ATTTGACTAATTACGAGT GGCTTGATAA | 951 |
| SEQ ID NO: 225 | Gene specific R19 | B-A*A*A*C*A*ATGCAC TCACTTCTTCCTAGAGAA GAGTACATTC | 1456 |
| SEQ ID NO: 226 | Gene specific F20 | MCCTATTAAATAAAAGAA TAAGCAGTATTATTAAGT AGCCCTGCATTTCA | 2170 |
| SEQ ID NO: 227 | Gene specific R20 | MCATCTGCTTTTTTCCCG TGTCATTCTCTGGACTG | 2170 |
| SEQ ID NO: 228 | Gene specific F21 | CCCACAATTCGCTCTCA CCAAACCTGAG | 2170 |
| SEQ ID NO: 229 | Gene specific R21 | AGTAGTAATAGTAGTAGT ATTAAATAATTTGATAAA TAATTTTAGCAATATAGT TTTTGT | 2170 |
| SEQ ID NO: 230 | Gene specific F22 | MCCCACAATTCGCTCTC ACCAAACCTGAG | 2567 |
| SEQ ID NO: 231 | Gene specific R22 | MAGTAGTAATAGTAGTA GTATTAAATAATTTGAT AAATAATTTTAGCAATA TAGTTTTTGT | 2814 |
| SEQ ID NO: 232 | Gene specific F23 | MCMCMCACAATTCGCTC TCACCAAACCTGAG | 2955 |
| SEQ ID NO: 233 | Gene specific R23 | MAMGMTAGTAATAGTAG TAGTATTAAATAATTTG ATAAATAATTTTAGCAA TATAGTTTTTGT | 2955 |
| SEQ ID NO: 234 | Gene specific F24 | B-C*C*C*A*C*AATTCG CTCTCACCAAACCTGAG | 2955 |
| SEQ ID NO: 235 | Gene specific R24 | B-A*G*T*A*G*TAATAG TAGTAGTATTAAATAATT TGATAAATAATTTTAGCA ATATAGTTTTTGT | 2955 |

DNA is uppercase; 2'-O-methoxyethyl modified ribonucleotides are shown with an uppercase M preceeding the modified ribonucleotide; B- is a 5'-biotin moiety; and phosphorothioate (PS) modified linkages are shown with an asterisk (*). All primers and templates were synthesized by IDT (Coralville, IA).

Figure 14B:
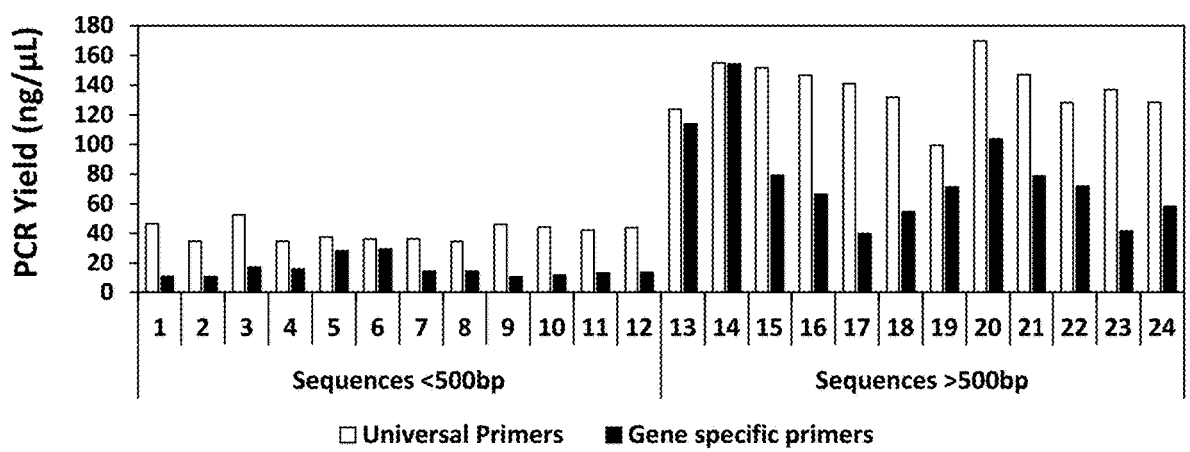

Owing to differences in the yields for short (<500 bp) and long (>500 bp) amplicons, overall yields following amplification with either universal or gene specific primers were assessed separately for 12 short and 12 long HDR templates (FIG. 14A). Overall, yields were significantly higher with the use of universal primers for both short and long amplicons. For long amplicons, use of universal primers resulted in an average concentration of 138.3 ng/µL (±18.0 SD) following cleanup while use of gene specific primers resulted in an average concentration of 77.8 ng/µL (±32.6 SD). For short amplicons, use of universal primers resulted in an average concentration of 40.9 ng/µL (±5.9 SD) following cleanup while use of gene specific primers resulted in an average concentration of 15.9 ng/µL (±6.4 SD). Direct comparisons between each sequence amplified with universal or gene specific primers (FIG. 14B) reveals large variation in the yields when using gene specific primers. In contrast, use of universal primers results in both higher yields (2.9- and 2.0-fold improvements on average for short and long amplicons, respectively) and greater consistency in the yields across sequences of similar length. Owing to the higher yields and greater consistency, the use of universal primers will better support the development of high-throughput manufacturing processes.

What is claimed is:

1. A double stranded DNA homology directed repair (HDR) donor comprising:
   a first homology arm region,
   an insert region,
   a second homology arm region; and
   universal primer sequences terminally flanking the first homology arm region and the second homology arm region;
   wherein:
      the first homology arm region and the second homology arm region comprise one or more 2'-OME, 2'-MOE, 2'-F, or 2'-oxygen-4'-carbon methylene (Locked Nucleic Acid) modifications of the 5'-terminal nucleotide, the 5'-penulimate nucleotide, the 5'-antepenultimate (third) nucleotide, or a combination of the nucleotides at or near the 5'-terminus of the first homology arm region and the second homology arm region;
      the 2'-OME and 2'-MOE modifications improve homology directed repair efficiency and reduce homology-independent integration; and
      the Locked Nucleic Acid and 2'-F modifications improve homology directed repair efficiency and increase homology-independent integration.

2. The double stranded DNA HDR donor of claim 1, wherein the modifications at or near the 5'-termini of the double stranded DNA HDR donor comprise 2'-MOE.

3. The double stranded DNA HDR donor of claim 1, wherein the modification at or near the 5'-termini are non-template mismatches relative to a target DNA.

4. The double stranded DNA HDR donor of claim 1, wherein the first homology arm region and the second homology arm region are 40 to 150 nucleotides in length.

5. The double stranded DNA HDR donor of claim 1, wherein the first homology arm region and the second homology arm region are at least 100 nucleotides in length.

6. The double stranded DNA HDR donor of claim 1, wherein the insert region is greater than 100 bp.

7. The double stranded DNA HDR donor of claim 1, wherein the insert region is greater than 0.25 kb, greater than 0.5 kb, greater than 1 kb, greater than 2 kb, greater than 3 kb, greater 4 kb, greater than 5 kb, greater than 6 kb, greater than 7 kb, greater than 8 kb, greater than 9 kb, or greater than 10 kb.

* * * * *